(12) United States Patent
Liu et al.

(10) Patent No.: US 10,961,318 B2
(45) Date of Patent: Mar. 30, 2021

(54) ANTI-SIRP-α ANTIBODIES AND RELATED METHODS

(71) Applicant: Forty Seven, Inc., Foster City, CA (US)

(72) Inventors: Jie Liu, Palo Alto, CA (US); Jens-Peter Volkmer, Menlo Park, CA (US)

(73) Assignee: Forty Seven, Inc., Foster City, CA (US)

( * ) Notice: Subject to any disclaimer, the term of this patent is extended or adjusted under 35 U.S.C. 154(b) by 0 days.

(21) Appl. No.: 16/045,312

(22) Filed: Jul. 25, 2018

(65) Prior Publication Data

US 2019/0119396 A1 Apr. 25, 2019

Related U.S. Application Data

(60) Provisional application No. 62/537,207, filed on Jul. 26, 2017.

(51) Int. Cl.
*C07K 16/28* (2006.01)
*A61K 39/395* (2006.01)

(52) U.S. Cl.
CPC ...... *C07K 16/2896* (2013.01); *A61K 39/3955* (2013.01); *C07K 16/2803* (2013.01); *C07K 2317/21* (2013.01); *C07K 2317/24* (2013.01); *C07K 2317/33* (2013.01); *C07K 2317/51* (2013.01); *C07K 2317/515* (2013.01); *C07K 2317/52* (2013.01); *C07K 2317/56* (2013.01); *C07K 2317/565* (2013.01); *C07K 2317/71* (2013.01); *C07K 2317/73* (2013.01); *C07K 2317/76* (2013.01); *C07K 2317/92* (2013.01)

(58) Field of Classification Search
CPC combination set(s) only.
See application file for complete search history.

(56) References Cited

U.S. PATENT DOCUMENTS

| | | | |
|---|---|---|---|
| 10,081,680 | B2 | 9/2018 | Weiskopf et al. |
| 10,611,842 | B2 | 4/2020 | Liu et al. |
| 2002/0155511 | A1 | 10/2002 | Horrocks et al. |
| 2014/0242095 | A1 | 8/2014 | Wang et al. |
| 2018/0037652 | A1* | 2/2018 | Liu .............. A61K 39/0011 |
| 2019/0023784 | A1 | 1/2019 | Chalons-Cottavoz et al. |
| 2019/0127477 | A1* | 5/2019 | Poirier ............ C07K 16/2896 |

FOREIGN PATENT DOCUMENTS

| | | |
|---|---|---|
| CN | 103665165 B | 2/2016 |
| EP | 2282772 B1 | 1/2014 |
| WO | WO-97/48723 A2 | 12/1997 |
| WO | WO-99/40940 A1 | 8/1999 |
| WO | WO-00/24869 A2 | 5/2000 |
| WO | WO-00/66159 A1 | 11/2000 |
| WO | WO-01/40307 A1 | 6/2001 |
| WO | WO-01/48020 A1 | 7/2001 |
| WO | WO-02/18938 A1 | 3/2002 |
| WO | WO-03/031650 A2 | 4/2003 |
| WO | WO-2004/024097 A2 | 3/2004 |
| WO | WO-2004/096133 A2 | 11/2004 |
| WO | WO-2004/108923 A1 | 12/2004 |
| WO | WO-2009/046541 A1 | 4/2009 |
| WO | WO-2009/091547 A1 | 7/2009 |
| WO | WO-2009/091601 A1 | 7/2009 |
| WO | WO-2009/131453 A1 | 10/2009 |
| WO | WO-2010/070047 A1 | 6/2010 |
| WO | WO-2010/130053 A1 | 11/2010 |
| WO | WO 2011/066501 A1 | 6/2011 |
| WO | WO-2011/076781 A1 | 6/2011 |
| WO | WO-2012/024782 A1 | 3/2012 |
| WO | WO-2012/162741 A1 | 12/2012 |
| WO | WO-2013/032948 A1 | 3/2013 |
| WO | WO-2013/056352 A1 | 4/2013 |
| WO | WO-2014/124028 A1 | 8/2014 |
| WO | WO-2014/179132 A1 | 11/2014 |
| WO | WO-2015/041987 A1 | 3/2015 |
| WO | WO 2015/138600 A2 | 9/2015 |
| WO | WO-2015/172037 A1 | 11/2015 |
| WO | WO-2016/005548 A1 | 1/2016 |
| WO | WO-2016/205042 A1 | 12/2016 |
| WO | WO 2017/068164 A1 | 4/2017 |
| WO | WO-2018/026600 A1 | 2/2018 |
| WO | WO-2019/023347 A1 | 1/2019 |

OTHER PUBLICATIONS

Yanagita et al (JCI Insight, published online Jan. 2017, 2:e89140).*
Weiskopf (European J Cancer, May 2017, 76:100-109).*
Ayi, K. et al., "CD47-SIRPα Interactions Regulate Macrophage Uptake of Plasmodium falciparum-Infected Erythrocytes and Clearance of Malaria In Vivo," Infection and Immunity, vol. 84, No. 7, Jul. 1, 2016, pp. 2002-2011.
Hezareh, M. et al., "Effector Function Activities of a Panel of Mutants of a Broadly Neutralizing Antibody against Human Immunodeficiency Virus Type 1," Jounral of Virology, vol. 75, No. 24, Dec. 2001, pp. 12161-12168.
OSE Immunotherapeutics, "Selective anti-SIRPα antibodies: Next generation checkpoint inhibitor: Targeting pro-tumors and suppressive myeloids cells," Sep. 2017, 35 pages.
PCT International Search Report and Written Opinion, PCT Application No. PCT/US2018/043699, Nov. 29, 2018, 18 pages.
Seiffert, M. et al., "Human Signal-Regulatory Protein is Expressed on Normal, but not on Subsets of Leukemic Myeloid Cells and Mediates Cullular Adhesion involving its Counterreceptor CD47," Blood, vol. 94, No. 11, Dec. 1, 1999, pp. 3633-3643.
Strohl, W., "Optimization of Fc-mediated effector functions of monoclonal antibodies," Current Opinion in Biotechnology, vol. 20, No. 6, Dec. 1, 2009, pp. 685-691.

(Continued)

*Primary Examiner* — Laura B Goddard

(74) *Attorney, Agent, or Firm* — Choate, Hall & Stewart LLP; Rolando Medina; Melissa M. Adams

(57) ABSTRACT

Anti-SIRPα antibodies, including multi-specific anti-SIRPα antibodies, are provided, as are related compositions and methods. The antibodies of the disclosure bind to SIRPα and can block the interaction of CD47 on one cell with SIRPα on a phagocytic cell.

33 Claims, 15 Drawing Sheets

Specification includes a Sequence Listing.

(56) References Cited

OTHER PUBLICATIONS

Takenaka, K. et al., "Polymorphism in Sirpa modulates engraftment of human hematopoietic stem cells," Nature Immunology vol. 8, 2007, pp. 1313-1323.
Yanagita, T. et al., "Anti-SIRPα antibodies as a potential new tool for cancel immunotherapy," JCI Insight, vol. 2, No. 1, Jan. 12, 2017, 15 pages.
Zhao, X. et al., "CD47-signal regulatory protein-α (SIRPα) interactions form a barrier for antibody-mediated tumor cell destruction," Proceedings of the National Academy of Sciences of the United States of America, vol. 108, No. 45, pp. 18342-18347.
Cameron, et al., "Myxoma virus M128L is expressed as a cell surface CD-47-like virulence factor that contributes to the downregulation of macrophage activation in vivo," Virology. Jun. 20, 2005; vol. 337, Issue 1: pp. 55-67.
Chao, et al., "Therapeutic antibody targeting of CD47 synergizes with rituximab to completely eradicate human B-cell lymphoma xenografts", Blood, Nov. 2009, vol. 114, No. 22: pp. 1063-1064 (abstract only).
Hatherley et al., "Paired Receptor Specificity Explained by Structures of Signal Regulatory Proteins Alone and Complexed with CD47," Jul. 25, 2008, Mollecular Cell, vol. 31, Issue 2: pp. 266-277.
Hatherley et al., "The Structure of the Macrophage Signal Regulatory Protein α (SIRPα) Inhibitory Receptor Reveals a Binding Face Reminiscent of That Usedby T Cell Receptors," The Journal of Biological Chemistry, May 11, 2007, vol. 282, Issue 19: pp. 14567-14575.
Jaiswal, et al., "CD47 is Upregulated on Circulating Hematopoietic Stem Cells and Leukemia Cells to Avoid Phagocytosis", Cell, Jul. 2009, vol. 138, No. 2: pp. 271-285.
Lee et al., "Novel Structural Determinants on SIRPα that Mediate Binding to CD47," The Journal of Immunology, 2007, vol. 179: pp. 7741-7750.
Lee et al., "The Role of cis Dimerization of Signal Regulatory Protein α (SIRP α) in Binding to CD47," The Journal of Biological Chemistry, Dec. 3, 2010, vol. 285, Issue 49: pp. 37953-37963.
Liu, J., et al. "Pre-Clinical Development of a Humanized Anti-CD47 Antibody with Anti-Cancer Therapeutic Potential", PloS ONE, Sep. 21, 2015, vol. 10, Issue 9: pp. 1-23.
Majeti, et al., "CD47 is an Adverse Prognostic Factor and Therapeutic Antibody Target on Human Acute Myeloid Leukemia Stem Cells", Cell, Jul. 2009, vol. 138, No. 2: pp. 286-299.
Manna and Frazier, "CD47 Mediates Killing of Breast Tumor Cells via Gi-Dependent Inhibition of Protein Kinase A," Cancer Research, Feb. 1, 2004, vol. 64: pp. 1026-1036.
Oldenborg, et al., "Role of CD47 as a marker of self on red blood cells", Science, 2000; vol. 288: pp. 2051-2054.
PCT International Search Report and Written Opinion, PCT Application No. PCT/US2015/019954, dated Oct. 15, 2015, 12 pages.
Sehn, et al., "Introduction of Combined CHOP Plus Rituximab Therapy Dramatically Improved Outcome of Diffuse Large B-Cell Lymphoma in British Comlumbia," J. Clin. Oncol., Aug. 1, 2005, vol. 23, Issue 22: pp. 5027-5033.
Topalian SL, Taube JM, Anders RA, and Pardoll DM. Mechanism-driven biomarkers to guide immune checkpoint blockade in cancer therapy. Nat Rev Cancer. 2016;16(5):275- 87.
Sharpe AH. Introduction to checkpoint inhibitors and cancer immunotherapy. Immunol Rev.2017;276(1):5-8.
Lee L, Gupta M, and Sahasranaman S. Immune Checkpoint inhibitors: An introduction to the next-generation cancer immunotherapy. J Clin Pharmacol. 2016;56(2)157-69.
Tarhini A. Immune-mediated adverse events associated with ipilimumab ctla-4 blockade therapy: the underlying mechanisms and clinical management. Scientifica (Cairo). 2013;2013:857519.
Seidel JA, Otsuka A, and Kabashima K. Anti-PD-1 and Anti-CTLA-4 Therapies in Cancer: Mechanisms of Action, Efficacy, and Limitations. Front Oncol. 2018;8:86.

Rotte A, Jin JY, and Lemaire V. Mechanistic overview of immune checkpoints to support the rational design of their combinations in cancer immunotherapy. Ann Oncol. 2018;29(1):71-83.
Michot JM, Bigenwald C, Champiat S, Collins M, Carbonnel F, Postel-Vinay S, et al. Immune-related adverse events with immune checkpoint blockade: a comprehensive review. Eur J Cancer. 2016;54:139-48.
Boutros C, Tarhini A, Routier E, Lambotte O, Ladurie FL, Carbonnel F, et al. Safety profiles of anti-CTLA-4 and anti-PD-1 antibodies alone and in combination. Nat Rev Clin Oncol. 2016;13(8):473-86.
Willingham SB, Volkmer JP, Gentles AJ, Sahoo D, Dalerba P, Mitra SS, et al. The CD47-signal regulatory protein alpha (SIRPa) interaction is a therapeutic target for human solid tumors. Proc Natl Acad Sci U S A. 2012;109(17):6662-7.
Liu J, Wang L, Zhao F, Tseng S, Narayanan C, Shura L, et al. Pre-Clinical Development of a Humanized Anti-CD47 Antibody with Anti-Cancer Therapeutic Potential. PLoS One. 2015;10(9):e0137345.
Chao MP, Alizadeh AA, Tang C, Myklebust JH, Varghese B, Gill S, et al. Anti-CD47 antibody synergizes with rituximab to promote phagocytosis and eradicate non-Hodgkin lymphoma. Cell. 2010;142(5):699-713.
Kim D, Wang J, Willingham SB, Martin R, Wernig G, and Weissman IL. Anti-CD47 antibodies promote phagocytosis and inhibit the growth of human myeloma cells. Leukemia. 2012;26(12):2538-45.
Tsai RK, and Discher DE. Inhibition of "self" engulfment through deactivation of myosin-II at the phagocytic synapse between human cells. J Cell Biol. 2008;180(5):989-1003.
Timms JF, Carlberg K, Gu H, Chen H, Kamatkar S, Nadler MJ, et al. Identification of major binding proteins and substrates for the SH2-containing protein tyrosine phosphatase SHP-1 in macrophages. Mol Cell Biol. 1998;18(7):3838-50.
Kharitonenkov A, Chen Z, Sures I, Wang H, Schilling J, and Ullrich A. A family of proteins that inhibit. signalling through tyrosine kinase receptors. Nature. 1997;386(6621):181-6.
Fujioka Y, Matozaki T, Noguchi T, Iwamatsu A, Yamao T, Takahashi N, et al. A novel membrane glycoprotein, SHPS-1, that binds the SH2-domain-containing protein tyrosine phosphatase SHP-2 in response to mitogens and cell adhesion. Mol Cell Biol. 1996;16(12):6887-99.
Adams S, van der Laan LJ, Vernon-Wilson E, Renardel de Lavalette C, Dopp EA, Dijkstra CD, et al. Signal-regulatory protein is selectively expressed by myeloid and neuronal cells. J Immunol. 1998;161(4):1853-9.
Queen C, Schneider WP, Selick HE, Payne PW, Landolfi NF, Duncan JF, et al. A humanized antibody that binds to the interleukin 2 receptor. Proc Natl Acad Sci U S A. 1989;86(24)1 0029-33.
Carter PJ. Potent antibody therapeutics by design. Nat Rev Immunol. 2006;6(5):343-57.
Ring NG, Herndler-Brandstetter D, Weiskopf K, Shan L, Volkmer JP, George BM, et al. Anti-SIRPalpha antibody immunotherapy enhances neutrophil and macrophage antitumor activity. Proc Natl Acad Sci U S A. 2017;114(49):E10578-E85.
Sim J, Sockolosky JT, Sangalang E, lzquierdo S, Pedersen D, Harriman W, et al. Discovery of high affinity, pan-allelic, and pan-mammalian reactive antibodies against the myeloid checkpoint receptor SIRPalpha. MAbs. 2019;11(6):1036-52.
Barclay AN, and Brown MH. The SIRP family of receptors and immune regulation. Nat Rev Immunol. 2006;6(6):457-64.
Piccio L, Vermi W, Boles KS, Fuchs A, Strader CA, Facchetti F, et al. Adhesion of human T cells to antigen-presenting cells through SIRPbeta2-CD47 interaction costimulates Tcell proliferation. Blood. 2005;105(6):2421-7.
Brooke G, Holbrook JD, Brown MH, and Barclay AN. Human lymphocytes interact directly with CD47 through a novel member of the signal regulatory protein (SIRP) family. J Immunol. 2004;173(4):2562-70.
Sikic Bi, Lakhani N, Patnaik A, Shah SA, Chandana SR, Rasco D, et al. First-in-Human, First-in-Class Phase I Trial of the Anti-CD47 Antibody Hu5F9-G4 in Patients With Advanced Cancers. J Clin Oncol. 2019;37(12):946-53.
Ritchie M, Tchistiakova L, and Scott N. Implications of receptor-mediated endocytosis and intracellular trafficking dynamics in the development of antibody drug conjugates. MAbs. 2013;5(1):13-21.

(56) References Cited

OTHER PUBLICATIONS

Panowski S, Bhakta S, Raab H, Polakis P, and Junutula JR. Site-specific antibody drug conjugates for cancer therapy. MAbs. 2014;6(1):34-45.
Nath N, Godat B, Zimprich C, Dwight SJ, Corona C, McDougall M, et al. Homogeneous plate based antibody internalization assay using pH sensor fluorescent dye. J Immunol Methods. 2016;431:11-21.
Casi G, and Neri D. Antibody-drug conjugates: basic concepts, examples and future perspectives. J Control Release. 2012;161(2):422-8.
Lammerts van Bueren JJ, Bleeker WK, Bogh HO, Houtkamp M, Schuurman J, van de Winkel JG, et al. Effect of target dynamics on pharmacokinetics of a novel therapeutic antibody against the epidermal growth factor receptor: implications for the mechanisms of action. Cancer Res. 2006;66(15):7630-8.
Chaparro-Riggers J, Liang H, DeVay RM, Bai L, Sutton JE, Chen W, et al. Increasing serum half-life and extending cholesterol lowering in vivo by engineering antibody with pH-sensitive binding to PCSK9. J Biol Chem. 2012;287(14):11090-7.
Amano J, Masuyama N, Hirota Y, Tanaka Y, Igawa Y, Shiokawa R, et al. Antigendependent internalization is related to rapid elimination from plasma of humanized anti-HM1.24 monoclonal antibody. Drug Metab Dispos. 2010;38(12):2339-46.
van Beek EM, Cochrane F, Barclay AN, and van den Berg TK. Signal regulatory proteins in the immune system. J Immunol. 2005;175(12):7781-7.
Liu et al. "Targeting macrophage checkpoint inhibitor SIRPa for anticancer therapy:", JCI Insight, 2020 https:doi.org/10.1172/jci.insight/134728.

* cited by examiner

QVQLQQPGAERVKPGASVKMSCKASGYTFTSYWITWVKQRPGQGLEWIGDIYPGSGSTNHIE
KFKSKATLTVDTSSNTAYMQLSRLTSEDSAVYYCATGYGSSYGYFDYWGQGTTLTVSS

B.

DIQMTQSPASLSASVGETVTITCRASENIYSYLAWYQQKQGKSPQLLVYTAKTLAEGVPSRFSGS
GSGTQFSLKINSLQPEDFGNYYCQHQYGPPFTFGSGTRLVIK

QVQLQQPGAELVRPGSSVKLSCKASGYTFTSYVWMHWVKQRPIQGLEWIGNIDPSDSDTHYNQKFKDKATLTVDKSSSTAYMQLSSLTSEDSAVYYCARGYSKYYAMDYWGQGTSVTVSS

B.

DVLMTQTPLSLSVSLGDQASISCRSSQSIVHSYGNTYLEWYLQKPGQSPKLLIYKVSNRFSGVPDRFSGSGSGTDFTLKISRVEAEDLGVYYCFQGSHVPYTFGGGTKLEIK

QVQLVQSGAEVKKPGASVKVSCKASGYTFTSYWITWVKQAPGQG
LEWIGDIYPGSGSTNHIEKFKSKATLTVDTSISTAYMELSRLRSDDTAVYYCATGYGSSYGYFDYW
GQGTLVTVSS

B.

DIQMTQSPSSLSASVGDRVTITCRASENIYSYLAWYQQKPGKAPKLLIYTAKTLAEGVPSRFSGSGS
GTDFTLTISSLQPEDFATYYCQHQYGPPFTFGQGTKLEIK

QVQLVQSGAEVKKPGASVKVSCKASGYTFTSYWMHWVRQAPGQGLEWMGNIDPSDSDTHY
NQKFKDRVTMTRDTSTSTVYMELSSLRSEDTAVYYCARGYSKYYAMDYWGQGTLVTVSS

B.

DIVMTQTPLSLSVTPGQPASISCRSSQSIVHSYGNTYLEWYLQKPGQSPQLLIYKVSNRFSGVPDR
FSGSGSGTDFTLKISRVEAEDVGVYYCFQGSHVPYTFGQGTKLEIK

ANTI-SIRP-α ANTIBODIES AND RELATED METHODS

CROSS REFERENCE TO RELATED APPLICATIONS

This application claims the benefit of U.S. Provisional Application No. 62/537,207, filed Jul. 26, 2017, which is hereby incorporated in its entirety by reference for all purposes.

SEQUENCE LISTING

The instant application contains a Sequence Listing which has been submitted via EFS-Web and is hereby incorporated by reference in its entirety. Said ASCII copy, created on Aug. 31, 2018, is named 40752US_CRF_sequencelisting.txt, and is 46 407 bytes in size.

BACKGROUND

Turnover of cells begins with the induction of an apoptotic program or other cellular changes that mark them for removal, and the subsequent recognition of markers by phagocytes, including macrophages, dendritic cells, and the like. This process requires a specific and selective removal of unwanted cells. Unlike healthy cells, the unwanted/aged/dying cells display markers or ligands called "eat-me" signals, i.e. "altered self", which can in turn be recognized by receptors on the phagocytes. Healthy cells may display "don't eat-me" signals that actively inhibit phagocytosis; these signals are either downregulated in the dying cells, are present in an altered conformation or they are superseded by the upregulation of "eat-me" or pro-phagocytic signals. The cell surface protein CD47 on healthy cells and its engagement of a phagocyte receptor, SIRPα, constitutes a key "don't eat-me" signal that can turn off engulfment mediated by multiple modalities, including apoptotic cell clearance and FcR mediated phagocytosis. Blocking the CD47 mediated engagement of SIRPα on a phagocyte can cause removal of live cells bearing "eat me" signals.

CD47 is a broadly expressed transmembrane glycoprotein with a single Ig-like domain and five membrane spanning regions, which functions as a cellular ligand for SIRPα with binding mediated through the NH2-terminal V-like domain of SIRPα. SIRPα is expressed primarily on myeloid cells, including macrophages, granulocytes, myeloid dendritic cells (DCs), mast cells, and their precursors, including hematopoietic stem cells. Structural determinants on SIRPα that mediate CD47 binding are discussed by Lee et al. (2007) J. Immunol. 179:7741-7750; Hatherley et al. (2007) J.B.C. 282:14567-75; and the role of SIRPα cis dimerization in CD47 binding is discussed by Lee et al. (2010) J.B.C. 285:37953-63. In keeping with the role of CD47 to inhibit phagocytosis of normal cells, there is evidence that it is transiently upregulated on hematopoietic stem cells (HSCs) and progenitors just prior to and during their migratory phase, and that the level of CD47 on these cells determines the probability that they are engulfed in vivo.

SUMMARY

Disclosed herein is an isolated humanized, human, or chimeric antibody that: specifically binds human SIRPα; does not specifically bind human SIRPγ; and optionally comprises a human Fc region comprising at least one modification that reduces binding to a human Fc receptor.

In some aspects, the antibody comprises: a CDR-H1 comprising the sequence set forth in SEQ ID NO: 1; a CDR-H2 comprising the sequence set forth in SEQ ID NO:2; a CDR-H3 comprising the sequence set forth in SEQ ID NO:3; a CDR-L1 comprising the sequence set forth in SEQ ID NO:4; a CDR-L2 comprising the sequence set forth in SEQ ID NO:5; and a CDR-L3 comprising the sequence set forth in SEQ ID NO:6; or a CDR-H1 comprising the sequence set forth in SEQ ID NO:9; a CDR-H2 comprising the sequence set forth in SEQ ID NO:10; a CDR-H3 comprising the sequence set forth in SEQ ID NO:11; a CDR-L1 comprising the sequence set forth in SEQ ID NO: 12; a CDR-L2 comprising the sequence set forth in SEQ ID NO:13; and a CDR-L3 comprising the sequence set forth in SEQ ID NO:14.

In some aspects, the antibody comprises: a $V_H$ sequence of SEQ ID NO:7 and a $V_L$ sequence of SEQ ID NO:8; or a $V_H$ sequence of SEQ ID NO:15 and a $V_L$ sequence of SEQ ID NO:16.

In some aspects, the antibody comprises: a heavy chain of SEQ ID NO: 17 and a light chain of SEQ ID NO:18; or a heavy chain of SEQ ID NO:19 and a light chain of SEQ ID NO:20.

Also disclosed herein is an isolated humanized, human, or chimeric antibody, comprising: a CDR-H1 comprising the sequence set forth in SEQ ID NO:1; a CDR-H2 comprising the sequence set forth in SEQ ID NO:2; a CDR-H3 comprising the sequence set forth in SEQ ID NO:3; a CDR-L1 comprising the sequence set forth in SEQ ID NO:4; a CDR-L2 comprising the sequence set forth in SEQ ID NO:5; and a CDR-L3 comprising the sequence set forth in SEQ ID NO:6.

Also disclosed herein is an isolated humanized, human, or chimeric antibody, comprising: a $V_H$ sequence of SEQ ID NO:7 and a $V_L$ sequence of SEQ ID NO:8.

Also disclosed herein is an isolated humanized, human, or chimeric antibody, comprising: a heavy chain of SEQ ID NO: 17 and a light chain of SEQ ID NO: 18.

Also disclosed herein is an isolated humanized, human, or chimeric antibody, comprising: a CDR-H1 comprising the sequence set forth in SEQ ID NO:9; a CDR-H2 comprising the sequence set forth in SEQ ID NO: 10; a CDR-H3 comprising the sequence set forth in SEQ ID NO:11; a CDR-L1 comprising the sequence set forth in SEQ ID NO:12; a CDR-L2 comprising the sequence set forth in SEQ ID NO:13; and a CDR-L3 comprising the sequence set forth in SEQ ID NO:14.

Also disclosed herein is an isolated humanized, human, or chimeric antibody, comprising: a $V_H$ sequence of SEQ ID NO:15 and a $V_L$ sequence of SEQ ID NO:16.

Also disclosed herein is an isolated humanized, human, or chimeric antibody, comprising: a heavy chain of SEQ ID NO: 19 and a light chain of SEQ ID NO:20.

In some aspects, an antibody disclosed herein comprises a human Fc region comprising at least one modification that reduces binding to a human Fc receptor.

In some aspects, an antibody disclosed herein: (a) competes for binding to human SIRPα with an antibody selected from 1H9 and 3C2; (b) does not compete for binding to human SIRPα with KWar antibody; (c) partially competes for binding to human SIRPα with KWar antibody; (d) inhibits binding of human CD47 to human SIRPα; (e) inhibits binding of human SP-A to human SIRPα; (f) inhibits binding of human SP-D to human SIRPα; (g) binds to rhesus monkey SIRPα; (h) binds to cynomolgus SIRPα; (i) increases phagocytosis relative to control; or (j) is capable of any combination of (a)-(i).

In some aspects, an antibody disclosed herein is pan-specific for human SIRPα isotypes. An antibody disclosed herein, such as 1H9, can bind to multiple human SIRPα isotypes including one or more of V1, V2, and V1/V5. An antibody disclosed herein can bind to each of human SIRPα isotypes V1 and V2. An antibody disclosed herein can bind to human SIRPα isotype V1, including homozygous. An antibody disclosed herein can bind to human SIRPα isotype V2, including homozygous. An antibody disclosed herein can bind to human SIRPα isotypes V1/V5 (heterozygous). An antibody disclosed herein, such as 1H9, can bind to multiple human SIRPα isotypes including each of V1, V2, and V1/V5. Such antibodies can include 1H9 and 3C2. Binding to the human SIRPα variants can be measured using assays known in the art including PCR and/or flow cytometry. For example, a given sample can be genotyped to determine SIRP status and binding to SIRP can be determined using flow cytometry.

In some aspects, an antibody disclosed herein is specific for a human SIRPα isotype.

In some aspects, human SIRPα is expressed on a professional antigen presenting cell. In some aspects, human SIRPα is expressed on a macrophage.

An antibody disclosed herein, such as 1H9, can bind to human SIRPα on the cell surface. The binding of an antibody disclosed herein to SIRPα can be stable, e.g., for 1, 2, 3, 4, 5, 6, 7, 8, 9, 10, 11, 12, 13, 14, 15, 16, 17, 18, 19, 20, 21, 22, 23, 24, or greater than 24 hours. An antibody disclosed herein can avoid substantial internalization upon binding to SIRPα. Such antibodies can include 1H9 and 3C2, including humanized and/or Fc engineered versions of such antibodies. Binding to the human SIRPα can be measured using assays known in the art including flow cytometry and/or IHC.

In some aspects, the antibody is 1H9 or 3C2.

In some aspects, the human Fc region is IgG1 or IgG4, optionally modified with a modification.

In some aspects, glycosylation of the antibody is reduced by enzymatic deglycosylation, expression in a bacterial host, or modification of an amino acid residue utilized for glycosylation. In some aspects, a modification disclosed herein reduces glycosylation of the human Fc region. In some aspects, the human Fc region modification comprises a modification at EU index position asparagine 297. In some aspects, the human Fc region modification comprises an amino acid substitution at EU index position asparagine 297. In some aspects, the human Fc region modification comprises an N297A amino acid substitution, numbering according to EU index. In some aspects, the modification comprises one or more amino acid substitutions at: N297A; L234A/L235A; C220S/C226S/C229S/P238S; C226S/C229S/E3233P/L234V/L235A; or L234F/L235E/P331S, numbering according to EU index. In some aspects, the modification comprises one or more amino acid substitutions at: N297; L234/L235; C220/C226/C229/P238; C226/C229/E3233/L234/L235; or L234/L235/P331, numbering according to EU index. In some aspects, the modification comprises one or more amino acid substitutions in the CH2 region at EU index positions 234, 235, and/or 237. In some aspects, the modification comprises one or both amino acid substitutions L234A and L235A, and optionally P331S and/or K322A and/or G237A, numbering according to EU index. In some aspects, the modification comprises amino acid substitution K322A, numbering according to EU index. In some aspects, the modification comprises E233P/L234V/L235A/G236+A327G/A330S/P331S, numbering according to EU index.

In some aspects, the antibody is a monoclonal antibody.

In some aspects, the antibody is multispecific. In some aspects, the antibody binds greater than one antigen or greater than one epitope on a single antigen.

In some aspects, the antibody comprises heavy chain constant region of a class selected from IgG, IgA, IgD, IgE, and IgM. In some aspects, the antibody comprises a heavy chain constant region of the class IgG and a subclass selected from IgG1, IgG4, IgG2, and IgG3.

In some aspects, the antibody binds human SIRPα with a $K_D$ of less than or equal to about 1, 1-6, 1-5, 1-4, 1-3, 2, 3, 4, 5, 6, 7, 8, 9, or $10\times10^{-9}$ M, as measured by Biacore assay.

In some aspects, an antibody disclosed herein is for use as a medicament. In some aspects, an antibody disclosed herein is for use in the treatment of a cancer or infection. In some aspects, an antibody disclosed herein is for use in the treatment of a cancer, wherein the cancer is selected from a solid tumor and a hematological tumor. In some aspects, an antibody disclosed herein is for use in increasing phagocytosis.

Also disclosed herein is an isolated humanized, human, or chimeric antibody that competes for binding to human SIRPα with an antibody disclosed herein.

Also disclosed herein is an isolated humanized, human, or chimeric antibody that binds the human SIRPα epitope bound by an antibody disclosed herein.

Also disclosed herein is an isolated polynucleotide or set of polynucleotides encoding an isolated antibody disclosed herein, a $V_H$ thereof, a $V_L$ thereof, a light chain thereof, a heavy chain thereof, or an antigen-binding portion thereof.

Also disclosed herein is a vector or set of vectors comprising a polynucleotide or set of polynucleotides disclosed herein.

Also disclosed herein is a host cell comprising a polynucleotide or set of polynucleotides disclosed herein or a vector or set of vectors disclosed herein.

Also disclosed herein is a method of producing an antibody comprising expressing the antibody with a host cell disclosed herein and isolating the expressed antibody.

Also disclosed herein is a pharmaceutical composition comprising an antibody disclosed herein and a pharmaceutically acceptable excipient.

Also disclosed herein is a method of treating or preventing a disease or condition in a subject in need thereof, comprising administering to the subject an effective amount of an antibody disclosed herein or a pharmaceutical composition disclosed herein.

In some aspects, the disease or condition is: cancer; infection; a viral infection; a bacterial infection; a fungal infection; fibrosis; artherosclerosis; a parasitic infection, optionally malaria; and depletion or reduction of endogenous blood-forming stem cells from bone marrow to allow radiation and/or chemotherapy—free or—reduced conditioning for transplantation of blood-forming stem cells, optionally in combination with anti-CKIT (CD117) antibody.

In some aspects, the disease or condition is a cancer, and the cancer is selected from a solid tumor and a hematological tumor.

Also disclosed herein is a method of increasing phagocytosis in a subject in need thereof, comprising administering to the subject an effective amount of an antibody disclosed herein or a pharmaceutical composition disclosed herein.

Also disclosed herein is a method of modulating an immune response in a subject in need thereof, comprising administering to the subject an effective amount of an antibody disclosed herein or a pharmaceutical composition disclosed herein.

In some aspects, a method disclosed herein further comprises administering one or more additional therapeutic agents to the subject.

In some aspects, the additional therapeutic agent is an antibody. In some aspects, the additional therapeutic agent is an antibody that binds a protein or proteins on a tumor cell surface. In some aspects, the additional therapeutic agent is an antibody that binds: HER2 (ERBB2/neu), CD52, PD-L1, VEGF, CD30, EGFR, CD38, RANKL (CD254), GD2 (ganglioside), SLAMF7 (CD319), CD20, EGFR, PDGFRa, VEGFR2, CD33, CD44, CD99, CD96, CD90, CD133, CKIT (CD117 for CKIT positive tumors); CTLA-4, PD-1, PD-L1, CD40 (agonistic), LAG3 (CD223), 41BB (CD137 agonistic), OX40 (CD134, agonistic); and/or CKIT (CD117) to deplete blood-forming stem cells for transplantation therapy. In some aspects, the additional therapeutic agent is at least one of: Rituximab, Cetuximab, Alemtuzumab (CD52), Atezolizumab (PD-L1), Avelumab (PD-L1), Bevacizumab (VEGF), Brentuximab (CD30), Daratumumab (CD38), Denosumab (RANKL), Dinutuximab (GD2), Elotuzumab (SLAMF7), Ibritumomab (CD20), Ipilimumab (CTLA-4), Necitumumab (EGFR), Nivolumab (PD-1), Obinutuzumab (CD20), Ofatumumab (CD20), Olaratumab (PDGFRa), Panitumumab (EGFR), Pembrolizumab (PD-1), Pertuzumab (HER2), Ramucirumab (VEGFR2), Tositumomab (CD20), and Gemtuzumab (CD33).

In some aspects, the additional therapeutic agent is formulated in the same pharmaceutical composition as the antibody. In some aspects, the additional therapeutic agent is formulated in a different pharmaceutical composition from the antibody.

In some aspects, the additional therapeutic agent is administered prior to administering the antibody. In some aspects, the additional therapeutic agent is administered after administering the antibody. In some aspects, the additional therapeutic agent is administered contemporaneously with the antibody.

Also disclosed herein is a kit comprising an antibody disclosed herein or a pharmaceutical composition disclosed herein; and instructions for use.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 1. Heavy (A) (SEQ ID NO: 55) and light (B) (SEQ ID NO: 56) chain variable region sequences of 1H9. CDRs are underlined.

FIG. 2. Heavy (A) (SEQ ID NO: 57) and light (B) (SEQ ID NO: 58) chain variable region sequences of 3C2. CDRs are underlined.

FIG. 5. Heavy (A) (SEQ ID NO: 7) and light (B) (SEQ ID NO: 8) chain variable region sequences of humanized 1H9. CDRs are underlined.

FIG. 6. Heavy (A) (SEQ ID NO: 15) and light (B) (SEQ ID NO: 16) chain variable region sequences of humanized 3C2. CDRs are underlined.

DETAILED DESCRIPTION

Definitions

Figure 3:
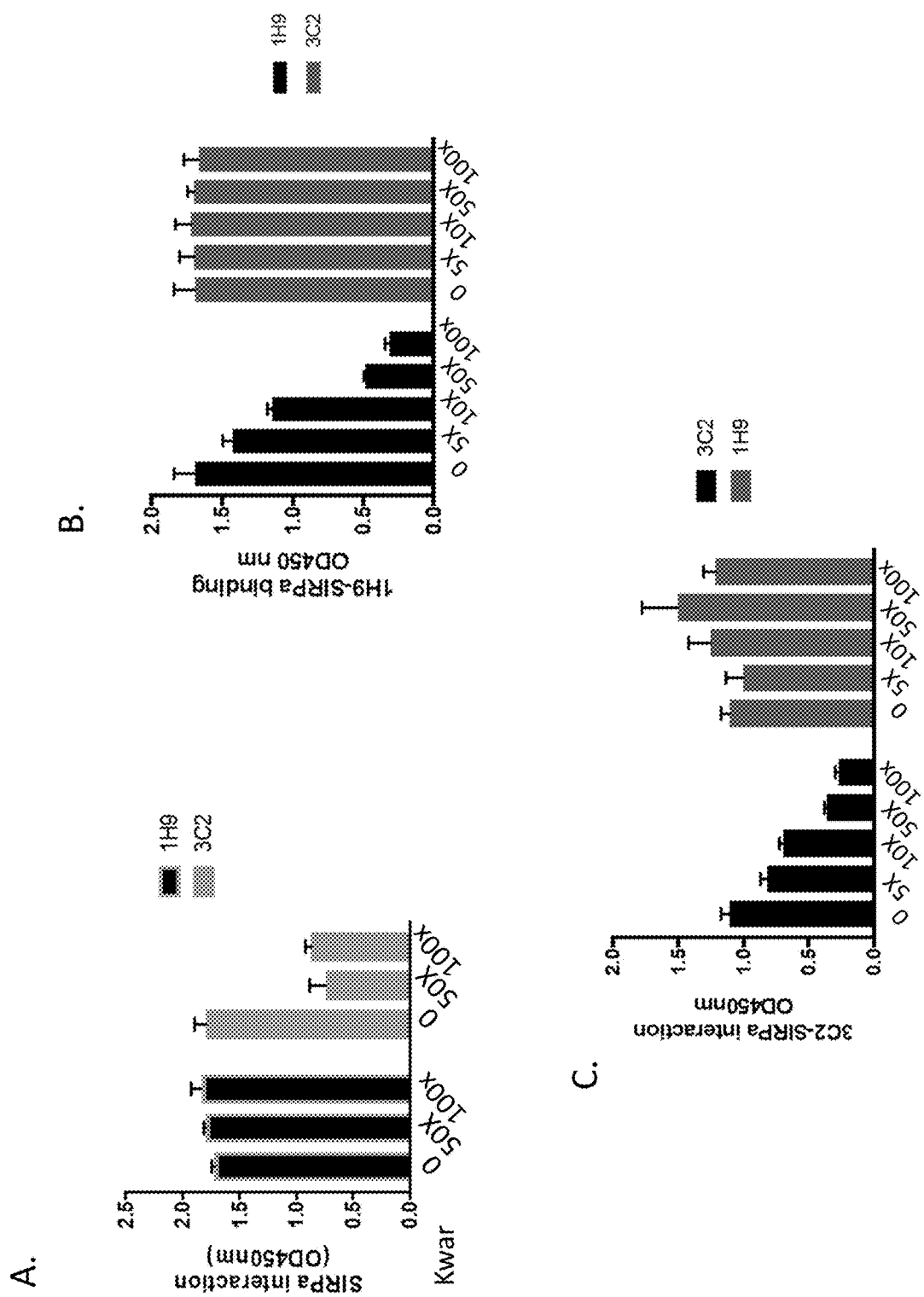
FIG. 3. 1H9 and 3C2 recognize distinct epitopes. (A) SIRPa-Fc fusion protein was coated in a 96-well plate and incubated with 1H9 or 3C2 in the absence or presence of 50- or 100-times excess amounts of mouse Kwar. (B) SIRPa-Fc fusion protein was coated in a 96-wells plate and incubated with mouse 1H9 in the absence or presence of 5-, 10-, 50- and 100-times excess amounts of 1H9 or 3C2. (C) SIRPa-Fc fusion protein was coated in a 96-wells plate and incubated with mouse 3C2 in the absence or presence of 5-, 10-, 50- and 100-times excess amounts of 3C2 or 1H9.

Unless otherwise defined, all terms of art, notations and other scientific terminology used herein are intended to have the meanings commonly understood by those of skill in the art. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., *Molecular Cloning: A Laboratory Manual* 4th ed. (2012) Cold Spring Harbor Laboratory Press, Cold Spring Harbor, N.Y. As appropriate, procedures involving the use of commercially available kits and reagents are generally carried out in accordance with manufacturer-defined protocols and conditions unless otherwise noted.

As used herein, the singular forms "a," "an," and "the" include the plural referents unless the context clearly indicates otherwise. The terms "include," "such as," and the like are intended to convey inclusion without limitation, unless otherwise specifically indicated.

As used herein, the term "comprising" also specifically includes embodiments "consisting of" and "consisting essentially of" the recited elements, unless specifically indicated otherwise. For example, a multispecific antibody "comprising a diabody" includes a multispecific antibody "consisting of a diabody" and a multispecific antibody "consisting essentially of a diabody."

The term "about" indicates and encompasses an indicated value and a range above and below that value. In certain embodiments, the term "about" indicates the designated value ±10%, ±5%, or ±1%. In certain embodiments, where applicable, the term "about" indicates the designated value(s) ±one standard deviation of that value(s).

SIRPα1 (PTPNS1, SHPS1), is a transmembrane glycoprotein, expressed primarily on myeloid and neuronal cells. SIRPα interacts with the widely distributed membrane protein CD47. In addition to SIRPα, there are two closely related proteins in the SIRP family: SIRPβ and SIRPγ. All three have three immunoglobulin superfamily (IgSF) domains in their extracellular region. In humans, the SIRPα protein is found in two major forms. One form, the variant 1 or V1 form, has the amino acid sequence set out as NCBI RefSeq NP_542970.1 (residues 27-504 constitute the mature form). Another form, the variant 2 or V2 form, differs by 13 amino acids and has the amino acid sequence set out in GenBank as CAA71403.1 (residues 30-504 constitute the mature form). These two forms of SIRPα constitute about 80% of the forms of SIRPα present in humans, and both are embraced herein by the term "human SIRPα". Also embraced by the term "human SIRPα" are the minor forms thereof that are endogenous to humans and have the same property of triggering signal transduction through CD47 upon binding thereto. Sequences of human SIRPα variants may be accessed through public databases, including Genbank accession numbers: ref|NP_542970.1; gb|EAX10606.1; ref|XP_005260726.1; gb|EAX10606.1; XP_005260726.1; gb|EAX10611.1; gb|EAX10609.1; dbj|BAA12974.1; gb|AAH26692.1; ref|XP_011527475.1. See, for example Lee et al. (2007) J. Immunol. 179(11):7741-7750; herein specifically incorporated by reference.

Antibodies that specifically bind to human SIRPα are known and used in the art, and may be adapted by the use of an engineered Fc region as disclosed herein. Exemplary antibodies include those described in international patent application WO 2015/138600; in published US application 2014/0242095 (University Health Networks); published application CN103665165 (JIANGSU KUANGYA BIOLOGICAL MEDICAL SCIENCE & TECHNOLOGY; Zhao X W et al. *Proc Natl Acad Sci USA* 108:18342-7 (2011), each herein specifically incorporated by reference. An anti-SIRPα antibody may be pan-specific, i.e. binding to two or more different human SIRPα isoforms; or may be specific for one isoform. For example, the antibody 1.23A described by Zhang et al., supra. is reported to be specific for the SIRPα1 variant, while the 12C4 antibody is pan-specific. Anti-SIRPα antibodies can also be specific for SIRPα and lack binding to SIRPβ and/or SIRPγ. Anti-SIRPα antibodies can be pan-specific with respect to SIRPβ and/or SIRPγ.

The term "immunoglobulin" refers to a class of structurally related proteins generally comprising two pairs of polypeptide chains: one pair of light (L) chains and one pair of heavy (H) chains. In an "intact immunoglobulin," all four of these chains are interconnected by disulfide bonds. The structure of immunoglobulins has been well characterized. See, e.g., Paul, *Fundamental Immunology* 7th ed., Ch. 5 (2013) Lippincott Williams & Wilkins, Philadelphia, Pa. Briefly, each heavy chain typically comprises a heavy chain variable region ($V_H$) and a heavy chain constant region ($C_H$). The heavy chain constant region typically comprises three domains, abbreviated $C_{H1}$, $C_{H2}$, and $C_{H3}$. Each light chain typically comprises a light chain variable region ($V_L$) and a light chain constant region. The light chain constant region typically comprises one domain, abbreviated $C_L$.

The term "antibody" is used herein in its broadest sense and includes certain types of immunoglobulin molecules comprising one or more antigen-binding domains that specifically bind to an antigen or epitope. An antibody specifically includes intact antibodies (e.g., intact immunoglobulins), antibody fragments, and multi-specific antibodies. In some embodiments, the antibody comprises an alternative scaffold. In some embodiments, the antibody consists of an alternative scaffold. In some embodiments, the antibody consists essentially of an alternative scaffold. In some embodiments, the antibody comprises an antibody fragment. In some embodiments, the antibody consists of an antibody fragment. In some embodiments, the antibody consists essentially of an antibody fragment. A "SIRP-ALPHA antibody," "anti-SIRP-ALPHA antibody," or "SIRP-ALPHA-specific antibody" is an antibody, as provided herein, which specifically binds to the antigen SIRP-ALPHA. In some embodiments, the antibody binds the extracellular domain of SIRP-ALPHA. In certain embodiments, a SIRP-ALPHA antibody provided herein binds to an epitope of SIRP-ALPHA that is conserved between or among SIRP-ALPHA proteins from different species.

The term "alternative scaffold" refers to a molecule in which one or more regions may be diversified to produce one or more antigen-binding domains that specifically bind to an antigen or epitope. In some embodiments, the antigen-binding domain binds the antigen or epitope with specificity and affinity similar to that of an antibody. Exemplary alternative scaffolds include those derived from fibronectin (e.g., Adnectins™), the β-sandwich (e.g., iMab), lipocalin (e.g., Anticalins®), EETI-II/AGRP, BPTI/LACI-D1/ITI-D2 (e.g., Kunitz domains), thioredoxin peptide aptamers, protein A (e.g., Affibody®), ankyrin repeats (e.g., DARPins), gamma-B-crystallin/ubiquitin (e.g., Affilins), CTLD$_3$ (e.g., Tetranectins), Fynomers, and (LDLR-A module) (e.g., Avimers). Additional information on alternative scaffolds is provided in Binz et al., *Nat. Biotechnol.*, 2005 23:1257-1268; Skerra, *Current Opin. in Biotech.*, 2007 18:295-304; and Silacci et al., *J. Biol. Chem.*, 2014, 289:14392-14398; each of which is incorporated by reference in its entirety. An alternative scaffold is one type of antibody.

The term "antigen-binding domain" means the portion of an antibody that is capable of specifically binding to an antigen or epitope. One example of an antigen-binding domain is an antigen-binding domain formed by a $V_H$-$V_L$ dimer of an antibody. Another example of an antigen-binding domain is an antigen-binding domain formed by diversification of certain loops from the tenth fibronectin type III domain of an Adnectin. An antigen-binding domain can include CDRs 1, 2, and 3 from a heavy chain in that order; and CDRs 1, 2, and 3 from a light chain in that order.

The terms "full length antibody," "intact antibody," and "whole antibody" are used herein interchangeably to refer to an antibody having a structure substantially similar to a naturally occurring antibody structure and having heavy chains that comprise an Fc region. For example, when used to refer to an IgG molecule, a "full length antibody" is an antibody that comprises two heavy chains and two light chains.

The term "Fc region" or "Fc" means the C-terminal region of an immunoglobulin heavy chain that, in naturally occurring antibodies, interacts with Fc receptors and certain proteins of the complement system. The structures of the Fc regions of various immunoglobulins, and the glycosylation sites contained therein, are known in the art. See Schroeder and Cavacini, *J. Allergy Clin. Immunol.*, 2010, 125:S41-52, incorporated by reference in its entirety. The Fc region may be a naturally occurring Fc region, or an Fc region modified as described in the art or elsewhere in this disclosure.

The $V_H$ and $V_L$ regions may be further subdivided into regions of hypervariability ("hypervariable regions (HVRs);" also called "complementarity determining regions" (CDRs)) interspersed with regions that are more conserved. The more conserved regions are called framework regions (FRs). Each $V_H$ and $V_L$ generally comprises three CDRs and four FRs, arranged in the following order (from N-terminus to C-terminus): FR1-CDR1-FR2-CDR2-FR3-CDR3-FR4. The CDRs are involved in antigen binding, and influence antigen specificity and binding affinity of the antibody. See Kabat et al., *Sequences of Proteins of Immunological Interest* 5th ed. (1991) Public Health Service, National Institutes of Health, Bethesda, Md., incorporated by reference in its entirety.

The light chain from any vertebrate species can be assigned to one of two types, called kappa (κ) and lambda (λ), based on the sequence of its constant domain.

The heavy chain from any vertebrate species can be assigned to one of five different classes (or isotypes): IgA, IgD, IgE, IgG, and IgM. These classes are also designated α, δ, ε, γ, and µ, respectively. The IgG and IgA classes are further divided into subclasses on the basis of differences in sequence and function. Humans express the following subclasses: IgG1, IgG2, IgG3, IgG4, IgA1, and IgA2.

The amino acid sequence boundaries of a CDR can be determined by one of skill in the art using any of a number of known numbering schemes, including those described by Kabat et al., supra ("Kabat" numbering scheme); Al-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., *Dev. Comp. Immunol.*, 2003, 27:55-77 ("IMGT" numbering scheme); and Honegge and Plückthun, *J. Mol. Biol.*, 2001, 309:657-70 ("AHo" numbering scheme); each of which is incorporated by reference in its entirety.

Table 1 provides the positions of CDR-L1, CDR-L2, CDR-L3, CDR-H1, CDR-H2, and CDR-H3 as identified by the Kabat and Chothia schemes. For CDR-H1, residue numbering is provided using both the Kabat and Chothia numbering schemes.

CDRs may be assigned, for example, using antibody numbering software, such as Abnum, available at www.bioinf.org.uk/abs/abnum/, and described in Abhinandan and Martin, *Immunology*, 2008, 45:3832-3839, incorporated by reference in its entirety.

TABLE 1

Residues in CDRs according to Kabat and Chothia numbering schemes.

| CDR | Kabat | Chothia |
|---|---|---|
| L1 | L24-L34 | L24-L34 |
| L2 | L50-L56 | L50-L56 |
| L3 | L89-L97 | L89-L97 |
| H1 (Kabat Numbering) | H31-H35B | H26-H32 or H34* |
| H1 (Chothia Numbering) | H31-H35 | H26-H32 |
| H2 | H50-H65 | H52-H56 |
| H3 | H95-H102 | H95-H102 |

*The C-terminus of CDR-H1, when numbered using the Kabat numbering convention, varies between H32 and H34, depending on the length of the CDR.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

An "antibody fragment" comprises a portion of an intact antibody, such as the antigen-binding or variable region of an intact antibody. Antibody fragments include, for example, Fv fragments, Fab fragments, F(ab')$_2$ fragments, Fab' fragments, scFv (sFv) fragments, and scFv-Fc fragments.

"Fv" fragments comprise a non-covalently-linked dimer of one heavy chain variable domain and one light chain variable domain.

"Fab" fragments comprise, in addition to the heavy and light chain variable domains, the constant domain of the light chain and the first constant domain ($C_{H1}$) of the heavy chain. Fab fragments may be generated, for example, by recombinant methods or by papain digestion of a full-length antibody.

"F(ab')$_2$" fragments contain two Fab' fragments joined, near the hinge region, by disulfide bonds. F(ab')$_2$ fragments may be generated, for example, by recombinant methods or by pepsin digestion of an intact antibody. The F(ab') fragments can be dissociated, for example, by treatment with β-mercaptoethanol.

"Single-chain Fv" or "sFv" or "scFv" antibody fragments comprise a $V_H$ domain and a $V_L$ domain in a single polypeptide chain. The $V_H$ and $V_L$ are generally linked by a peptide linker. See Plückthun A. (1994). Any suitable linker may be used. In some embodiments, the linker is a (GGGGS)$_n$ (SEQ ID NO: 50). In some embodiments, n=1, 2, 3, 4, 5, or 6. See Antibodies from *Escherichia coli*. In Rosenberg M. & Moore G.P. (Eds.), *The Pharmacology of Monoclonal Antibodies* vol. 113 (pp. 269-315). Springer-Verlag, New York, incorporated by reference in its entirety.

"scFv-Fc" fragments comprise an scFv attached to an Fc domain. For example, an Fc domain may be attached to the C-terminal of the scFv. The Fc domain may follow the $V_H$ or $V_L$, depending on the orientation of the variable domains in the scFv (i.e., $V_H$—$V_L$ or $V_L$—$V_H$). Any suitable Fc domain known in the art or described herein may be used. In some cases, the Fc domain comprises an IgG4 Fc domain.

The term "single domain antibody" refers to a molecule in which one variable domain of an antibody specifically binds to an antigen without the presence of the other variable domain. Single domain antibodies, and fragments thereof, are described in Arabi Ghahroudi et al., *FEBS Letters*, 1998, 414:521-526 and Muyldermans et al., *Trends in Biochem. Sci.*, 2001, 26:230-245, each of which is incorporated by reference in its entirety. Single domain antibodies are also known as sdAbs or nanobodies.

A "multispecific antibody" is an antibody that comprises two or more different antigen-binding domains that collectively specifically bind two or more different epitopes. The two or more different epitopes may be epitopes on the same antigen (e.g., a single SIRP-ALPHA molecule expressed by a cell) or on different antigens (e.g., different SIRP-ALPHA molecules expressed by the same cell, or a SIRP-ALPHA molecule and a non-SIRP-ALPHA molecule). In some aspects, a multi-specific antibody binds two different epitopes (i.e., a "bispecific antibody"). In some aspects, a multi-specific antibody binds three different epitopes (i.e., a "trispecific antibody").

A "monospecific antibody" is an antibody that comprises one or more binding sites that specifically bind to a single epitope. An example of a monospecific antibody is a naturally occurring IgG molecule which, while divalent (i.e., having two antigen-binding domains), recognizes the same epitope at each of the two antigen-binding domains. The binding specificity may be present in any suitable valency.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "chimeric antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human antibody (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. For further details, see Jones et al., *Nature*, 1986, 321:522-525; Riechmann et al., *Nature*, 1988, 332:323-329; and Presta, *Curr. Op. Struct. Biol.*, 1992, 2:593-596, each of which is incorporated by reference in its entirety.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

"Affinity" refers to the strength of the sum total of non-covalent interactions between a single binding site of a molecule (e.g., an antibody) and its binding partner (e.g., an antigen or epitope). Unless indicated otherwise, as used herein, "affinity" refers to intrinsic binding affinity, which reflects a 1:1 interaction between members of a binding pair (e.g., antibody and antigen or epitope). The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein, such as surface plasmon resonance (SPR) technology (e.g., BIACORE®) or biolayer interferometry (e.g., FORTEBIO®).

With regard to the binding of an antibody to a target molecule, the terms "bind," "specific binding," "specifically binds to," "specific for," "selectively binds," and "selective for" a particular antigen (e.g., a polypeptide target) or an epitope on a particular antigen mean binding that is measurably different from a non-specific or non-selective interaction (e.g., with a non-target molecule). Specific binding can be measured, for example, by measuring binding to a target molecule and comparing it to binding to a non-target molecule. Specific binding can also be determined by competition with a control molecule that mimics the epitope recognized on the target molecule. In that case, specific binding is indicated if the binding of the antibody to the target molecule is competitively inhibited by the control molecule. In some aspects, the affinity of a SIRP-ALPHA antibody for a non-target molecule is less than about 50% of the affinity for SIRP-ALPHA. In some aspects, the affinity of a SIRP-ALPHA antibody for a non-target molecule is less than about 40% of the affinity for SIRP-ALPHA. In some aspects, the affinity of a SIRP-ALPHA antibody for a non-target molecule is less than about 30% of the affinity for SIRP-ALPHA. In some aspects, the affinity of a SIRP-ALPHA antibody for a non-target molecule is less than about 20% of the affinity for SIRP-ALPHA. In some aspects, the affinity of a SIRP-ALPHA antibody for a non-target molecule is less than about 10% of the affinity for SIRP-ALPHA. In some aspects, the affinity of a SIRP-ALPHA antibody for a non-target molecule is less than about 1% of the affinity for SIRP-ALPHA. In some aspects, the affinity of a SIRP-ALPHA antibody for a non-target molecule is less than about 0.1% of the affinity for SIRP-ALPHA.

The term "$k_d$" ($sec^{-1}$), as used herein, refers to the dissociation rate constant of a particular antibody-antigen interaction. This value is also referred to as the $k_{off}$ value.

The term "$k_a$" ($M^{-1} \times sec^{-1}$), as used herein, refers to the association rate constant of a particular antibody-antigen interaction. This value is also referred to as the $k_{on}$ value.

The term "$K_D$" (M), as used herein, refers to the dissociation equilibrium constant of a particular antibody-antigen interaction. $K_D = k_d/k_a$. In some embodiments, the affinity of an antibody is described in terms of the $K_D$ for an interaction between such antibody and its antigen. For clarity, as known in the art, a smaller $K_D$ value indicates a higher affinity interaction, while a larger $K_D$ value indicates a lower affinity interaction.

The term "$K_A$" ($M^{-1}$), as used herein, refers to the association equilibrium constant of a particular antibody-antigen interaction. $K_A=k_a/k_d$.

An "immunoconjugate" is an antibody conjugated to one or more heterologous molecule(s), such as a therapeutic (cytokine, for example) or diagnostic agent.

"Effector functions" refer to those biological activities mediated by the Fc region of an antibody, which activities may vary depending on the antibody isotype. Examples of antibody effector functions include C1q binding to activate complement dependent cytotoxicity (CDC), Fc receptor binding to activate antibody-dependent cellular cytotoxicity (ADCC), and antibody dependent cellular phagocytosis (ADCP).

When used herein in the context of two or more antibodies, the term "competes with" or "cross-competes with" indicates that the two or more antibodies compete for binding to an antigen (e.g., SIRP-ALPHA). In one exemplary assay, SIRP-ALPHA is coated on a surface and contacted with a first SIRP-ALPHA antibody, after which a second SIRP-ALPHA antibody is added. In another exemplary assay, a first SIRP-ALPHA antibody is coated on a surface and contacted with SIRP-ALPHA, and then a second SIRP-ALPHA antibody is added. If the presence of the first SIRP-ALPHA antibody reduces binding of the second SIRP-ALPHA antibody, in either assay, then the antibodies compete with each other. The term "competes with" also includes combinations of antibodies where one antibody reduces binding of another antibody, but where no competition is observed when the antibodies are added in the reverse order. However, in some embodiments, the first and second antibodies inhibit binding of each other, regardless of the order in which they are added. In some embodiments, one antibody reduces binding of another antibody to its antigen by at least 25%, at least 50%, at least 60%, at least 70%, at least 80%, at least 85%, at least 90%, or at least 95%. A skilled artisan can select the concentrations of the antibodies used in the competition assays based on the affinities of the antibodies for SIRP-ALPHA and the valency of the antibodies. The assays described in this definition are illustrative, and a skilled artisan can utilize any suitable assay to determine if antibodies compete with each other. Suitable assays are described, for example, in Cox et al., "Immunoassay Methods," in *Assay Guidance Manual* [*Internet*], Updated Dec. 24, 2014 (www.ncbi.nlm.nih.gov/books/NBK92434/; accessed Sep. 29, 2015); Silman et al., *Cytometry*, 2001, 44:30-37; and Finco et al., *J. Pharm. Biomed. Anal.*, 2011, 54:351-358; each of which is incorporated by reference in its entirety.

The term "epitope" means a portion of an antigen that specifically binds to an antibody. Epitopes frequently consist of surface-accessible amino acid residues and/or sugar side chains and may have specific three dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding, and other amino acid residues, which are not directly involved in the binding. The epitope to which an antibody binds can be determined using known techniques for epitope determination such as, for example, testing for antibody binding to SIRP-ALPHA variants with different point-mutations, or to chimeric SIRP-ALPHA variants.

Percent "identity" between a polypeptide sequence and a reference sequence, is defined as the percentage of amino acid residues in the polypeptide sequence that are identical to the amino acid residues in the reference sequence, after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, MEGALIGN (DNASTAR), CLUSTALW, CLUSTAL OMEGA, or MUSCLE software. Those skilled in the art can determine appropriate parameters for aligning sequences, including any algorithms needed to achieve maximal alignment over the full length of the sequences being compared.

A "conservative substitution" or a "conservative amino acid substitution," refers to the substitution an amino acid with a chemically or functionally similar amino acid. Conservative substitution tables providing similar amino acids are well known in the art. By way of example, the groups of amino acids provided in Tables 2-4 are, in some embodiments, considered conservative substitutions for one another.

TABLE 2

Selected groups of amino acids that are considered conservative substitutions for one another, in certain embodiments.

| | |
|---|---|
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |

TABLE 3

Additional selected groups of amino acids that are considered conservative substitutions for one another, in certain embodiments.

| | |
|---|---|
| Group 1 | A, S, and T |
| Group 2 | D and E |
| Group 3 | N and Q |
| Group 4 | R and K |
| Group 5 | I, L, and M |
| Group 6 | F, Y, and W |

TABLE 4

Further selected groups of amino acids that are considered conservative substitutions for one another, in certain embodiments.

| | |
|---|---|
| Group A | A and G |
| Group B | D and E |
| Group C | N and Q |
| Group D | R, K, and H |
| Group E | I, L, M, V |
| Group F | F, Y, and W |
| Group G | S and T |
| Group H | C and M |

Additional conservative substitutions may be found, for example, in Creighton, *Proteins: Structures and Molecular Properties* 2nd ed. (1993) W. H. Freeman & Co., New York, N.Y. An antibody generated by making one or more conservative substitutions of amino acid residues in a parent antibody is referred to as a "conservatively modified variant."

The term "amino acid" refers to the twenty common naturally occurring amino acids. Naturally occurring amino acids include alanine (Ala; A), arginine (Arg; R), asparagine (Asn; N), aspartic acid (Asp; D), cysteine (Cys; C); glutamic acid (Glu; E), glutamine (Gln; Q), Glycine (Gly; G); histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell," "host cell line," and "host cell culture" are used interchangeably and refer to cells into which an exogenous nucleic acid has been introduced, and the progeny of such cells. Host cells include "transformants" (or "transformed cells") and "transfectants" (or "transfected cells"), which each include the primary transformed or transfected cell and progeny derived therefrom. Such progeny may not be completely identical in nucleic acid content to a parent cell, and may contain mutations.

The term "treating" (and variations thereof such as "treat" or "treatment") refers to clinical intervention in an attempt to alter the natural course of a disease or condition in a subject in need thereof. Treatment can be performed both for prophylaxis and during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

As used herein, the term "therapeutically effective amount" or "effective amount" refers to an amount of an antibody or pharmaceutical composition provided herein that, when administered to a subject, is effective to treat a disease or disorder.

As used herein, the term "subject" means a mammalian subject. Exemplary subjects include humans, monkeys, dogs, cats, mice, rats, cows, horses, camels, goats, rabbits, and sheep. In certain embodiments, the subject is a human. In some embodiments the subject has a disease or condition that can be treated with an antibody provided herein. In some aspects, the disease or condition is a cancer. In some aspects, the disease or condition is a viral infection.

The term "package insert" is used to refer to instructions customarily included in commercial packages of therapeutic or diagnostic products (e.g., kits) that contain information about the indications, usage, dosage, administration, combination therapy, contraindications and/or warnings concerning the use of such therapeutic or diagnostic products.

The term "cytotoxic agent," as used herein, refers to a substance that inhibits or prevents a cellular function and/or causes cell death or destruction.

A "chemotherapeutic agent" refers to a chemical compound useful in the treatment of cancer. Chemotherapeutic agents include "anti-hormonal agents" or "endocrine therapeutics" which act to regulate, reduce, block, or inhibit the effects of hormones that can promote the growth of cancer.

The term "cytostatic agent" refers to a compound or composition which arrests growth of a cell either in vitro or in vivo. In some embodiments, a cytostatic agent is an agent that reduces the percentage of cells in S phase. In some embodiments, a cytostatic agent reduces the percentage of cells in S phase by at least about 20%, at least about 40%, at least about 60%, or at least about 80%.

The term "tumor" refers to all neoplastic cell growth and proliferation, whether malignant or benign, and all precancerous and cancerous cells and tissues. The terms "cancer," "cancerous," "cell proliferative disorder," "proliferative disorder" and "tumor" are not mutually exclusive as referred to herein. The terms "cell proliferative disorder" and "proliferative disorder" refer to disorders that are associated with some degree of abnormal cell proliferation. In some embodiments, the cell proliferative disorder is a cancer. In some aspects, the tumor is a solid tumor. In some aspects, the tumor is a hematologic malignancy.

The term "pharmaceutical composition" refers to a preparation which is in such form as to permit the biological activity of an active ingredient contained therein to be effective in treating a subject, and which contains no additional components which are unacceptably toxic to the subject in the amounts provided in the pharmaceutical composition.

The terms "co-administration", "co-administer", and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

The terms "modulate" and "modulation" refer to reducing or inhibiting or, alternatively, activating or increasing, a recited variable.

The terms "increase" and "activate" refer to an increase of 10%, 20%, 30%, 40%, 50%, 60%, 70%, 75%, 80%, 85%, 90%, 95%, 100%, 2-fold, 3-fold, 4-fold, 5-fold, 10-fold, 20-fold, 50-fold, 100-fold, or greater in a recited variable.

The terms "reduce" and "inhibit" refer to a decrease of 10%, 20%, 30%, 40%, 50%, 60%, 70%, 75%, 80%, 85%, 90%, 95%, 2-fold, 3-fold, 4-fold, 5-fold, 10-fold, 20-fold, 50-fold, 100-fold, or greater in a recited variable.

The term "agonize" refers to the activation of receptor signaling to induce a biological response associated with activation of the receptor. An "agonist" is an entity that binds to and agonizes a receptor.

The term "antagonize" refers to the inhibition of receptor signaling to inhibit a biological response associated with activation of the receptor. An "antagonist" is an entity that binds to and antagonizes a receptor.

SIRP-ALPHA Antibodies

Provided herein are antibodies that specifically bind to SIRP-ALPHA. In some aspects, the SIRP-ALPHA is human SIRP-ALPHA. In some embodiments, the antibodies provided herein specifically bind to the extracellular domain of SIRP-ALPHA. The SIRP-ALPHA may be expressed on the surface of any suitable target cell. In some embodiments, the target cell is a professional antigen presenting cell. In some embodiments, the target cell is a macrophage. An antibody can be pan-specific for human SIRPα isotypes. An antibody can be specific for a human SIRPα isotype.

In certain embodiments an antibody is 1H9. In certain embodiments an antibody is 3C2.

In some embodiments, the antibodies provided herein comprise a light chain. In some aspects, the light chain is a kappa light chain. In some aspects, the light chain is a lambda light chain.

In some embodiments, the antibodies provided herein comprise a heavy chain. In some aspects, the heavy chain is an IgA. In some aspects, the heavy chain is an IgD. In some aspects, the heavy chain is an IgE. In some aspects, the heavy chain is an IgG. In some aspects, the heavy chain is an IgM. In some aspects, the heavy chain is an IgG1. In some aspects, the heavy chain is an IgG2. In some aspects, the heavy chain is an IgG3. In some aspects, the heavy chain is an IgG4. In some aspects, the heavy chain is an IgA1. In some aspects, the heavy chain is an IgA2.

In some embodiments, an antibody binds human SIRPα with a $K_D$ of less than or equal to about 1, 1-6, 1-5, 1-4, 1-3, 2, 3, 4, 5, 6, 7, 8, 9, or $10 \times 10^{-9}$ M, as measured by Biacore assay.

In some embodiments, the antibodies provided herein comprise an antibody fragment. In some embodiments, the antibodies provided herein consist of an antibody fragment. In some embodiments, the antibodies provided herein consist essentially of an antibody fragment. In some aspects, the antibody fragment is an Fv fragment. In some aspects, the antibody fragment is a Fab fragment. In some aspects, the antibody fragment is a F(ab')2 fragment. In some aspects, the antibody fragment is a Fab' fragment. In some aspects, the antibody fragment is an scFv (sFv) fragment. In some aspects, the antibody fragment is an scFv-Fc fragment. In some aspects, the antibody fragment is a fragment of a single domain antibody.

In some embodiments, an antibody fragment provided herein is derived from an illustrative antibody provided herein. In some embodiments, an antibody fragments provided herein is not derived from an illustrative antibody provided herein and may, for example, be isolated de novo according to the methods provided herein for obtaining antibody fragments.

In some embodiments, an antibody fragment provided herein retains the ability to antagonize SIRP-ALPHA, as measured by one or more assays or biological effects described herein. In some embodiments, an antibody fragment provided herein retains the ability to prevent SIRP-ALPHA from interacting with one or more of its ligands, as described herein.

In some embodiments, an antibody fragment provided herein competes for binding to SIRP-ALPHA with 1H9 and/or 3C2. In some embodiments, a fragment of an antibody provided herein binds the same epitope of SIRP-ALPHA as such antibody.

As an alternative to the use of an antibody comprising a human Fc region with reduced affinity for an Fcγ receptor, an antibody can be engineered to lack Fc sequences, e.g., by producing an antibody fragment such as a F(ab')2 fragment. To generate an F(ab)2 fragment, the purified antibody is suspended with Pierce F(ab')2 Preparation pepsin immobilized on settled resin, according to the manufacturer's instructions. Pepsin digestion typically produces a F(ab')2 fragment (~110 kDa by SDS-PAGE under non-reducing conditions) and numerous small peptides of the Fc portion. The resulting F(ab')2 fragment is composed of a pair of Fab' units connected by two disulfide bonds. The Fc fragment is extensively degraded and separated from F(ab')2 by dialysis, gel filtration, or ion exchange chromatography.

In some embodiments, the antibodies provided herein are monoclonal antibodies. In some embodiments, the antibodies provided herein are polyclonal antibodies.

In some embodiments, the antibodies provided herein comprise a chimeric antibody. In some embodiments, the antibodies provided herein consist of a chimeric antibody. In some embodiments, the antibodies provided herein consist essentially of a chimeric antibody. In some embodiments, the antibodies provided herein comprise a humanized antibody. In some embodiments, the antibodies provided herein consist of a humanized antibody. In some embodiments, the antibodies provided herein consist essentially of a humanized antibody. In some embodiments, the antibodies provided herein comprise a human antibody. In some embodiments, the antibodies provided herein consist of a human antibody. In some embodiments, the antibodies provided herein consist essentially of a human antibody.

In some embodiments, the antibodies provided herein comprise an alternative scaffold. In some embodiments, the antibodies provided herein consist of an alternative scaffold. In some embodiments, the antibodies provided herein consist essentially of an alternative scaffold. Any suitable alternative scaffold may be used. In some aspects, the alternative scaffold is selected from an Adnectin™, an iMab, an Anticalin®, an EETI-II/AGRP, a Kunitz domain, a thioredoxin peptide aptamer, an Affibody®, a DARPin, an Affilin, a Tetranectin, a Fynomer, and an Avimer.

In some embodiments, an antibody provided herein inhibits binding of SIRP-ALPHA to one or more ligands of SIRP-ALPHA.

In certain aspects, an antibody does not bind to SIRP-Gamma. In certain aspects, an antibody does not substantially bind to SIRP-Gamma.

In some aspects, an antibody disclosed herein is pan-specific for human SIRPα isotypes. An antibody disclosed herein, such as 1H9, can bind to multiple human SIRPα isotypes including one or more of V1, V2, and V1/V5. Exemplary V1 sequence shown in SEQ ID NO:48. Exemplary V2 sequence shown in SEQ ID NO:49. See also Polymorphism in Sirpa modulates engraftment of human hematopoietic stem cells. Nature Immunology, 8; 1313, 2007. An antibody disclosed herein can bind to each of human SIRPα isotypes V1 and V2. An antibody disclosed herein can bind to human SIRPα isotype V1, including homozygous. An antibody disclosed herein can bind to human SIRPα isotype V2, including homozygous. An antibody disclosed herein can bind to human SIRPα isotypes V1/V5 (heterozygous). An antibody disclosed herein, such as 1H9, can bind to multiple human SIRPα isotypes including each of V1, V2, and V1/V5. Such antibodies can include 1H9 and 3C2, including humanized and/or Fc engineered versions of such antibodies. 1H9 can bind to each of human SIRPα isotypes V1 and V2. 1H9 can bind to human SIRPα isotype V1, including homozygous. 1H9 can bind to human SIRPα isotype V2, including homozygous. 1H9 can bind to human SIRPα isotypes V1/V5 (heterozygous). 1H9 can bind to multiple human SIRPα isotypes including each of V1, V2, and V1/V5. Binding to the human SIRPα variants can be measured using assays known in the art including PCR and/or flow cytometry. For example, a given sample can be genotyped to determine SIRP status and binding to SIRP can be determined using flow cytometry.

In certain aspects, an antibody competes for binding to human SIRPα with an antibody selected from 1H9 and 3C2. In certain aspects, an antibody binds to the same human SIRPα epitope as bound by 1H9 or 3C2. In certain aspects, an antibody binds to an overlapping human SIRPα epitope as bound by 1H9 or 3C2. In certain aspects, an antibody binds to a distinct human SIRPα epitope as bound by 1H9 or 3C2.

In certain aspects, an antibody does not compete for binding to human SIRPα with KWar antibody.

In certain aspects, an antibody partially competes for binding to human SIRPα with KWar antibody.

In certain aspects, an antibody inhibits binding of human CD47 to human SIRPα.

In certain aspects, an antibody inhibits binding of human SP-A to human SIRPα.

In certain aspects, an antibody inhibits binding of human SP-D to human SIRPα.

In certain aspects, an antibody binds to rhesus monkey SIRPα.

In certain aspects, an antibody binds to cynomolgus SIRPα.

In certain aspects, an antibody increases phagocytosis relative to control.

Also disclosed herein is an isolated humanized, human, or chimeric antibody that competes for binding to human SIRPα with an antibody disclosed herein.

Also disclosed herein is an isolated humanized, human, or chimeric antibody that binds the human SIRPα epitope bound by an antibody disclosed herein.

In certain aspects, an antibody comprises a human Fc region comprising at least one modification that reduces binding to a human Fc receptor.

In some embodiments, an antibody is an antibody that competes with an illustrative antibody provided herein, e.g., 1H9 and/or 3C2. In some aspects, the antibody that competes with the illustrative antibody provided herein binds the same epitope as an illustrative antibody provided herein.

It is known that when an antibody is expressed in cells, the antibody is modified after translation. Examples of the posttranslational modification include cleavage of lysine at the C terminal of the heavy chain by a carboxypeptidase; modification of glutamine or glutamic acid at the N terminal of the heavy chain and the light chain to pyroglutamic acid by pyroglutamylation; glycosylation; oxidation; deamidation; and glycation, and it is known that such posttranslational modifications occur in various antibodies (See Journal of Pharmaceutical Sciences, 2008, Vol. 97, p. 2426-2447, incorporated by reference in its entirety). In some embodiments, an antibody is an antibody or antigen-binding fragment thereof which has undergone posttranslational modification. Examples of an antibody or antigen-binding fragment thereof which have undergone posttranslational modification include an antibody or antigen-binding fragments thereof which have undergone pyroglutamylation at the N terminal of the heavy chain variable region and/or deletion of lysine at the C terminal of the heavy chain. It is known in the art that such posttranslational modification due to pyroglutamylation at the N terminal and deletion of lysine at the C terminal does not have any influence on the activity of the antibody or fragment thereof (Analytical Biochemistry, 2006, Vol. 348, p. 24-39, incorporated by reference in its entirety).

Sequences of SIRP-ALPHA Antibodies

An antibody can comprise: a CDR-H1 comprising the sequence set forth in SEQ ID NO: 1; a CDR-H2 comprising the sequence set forth in SEQ ID NO:2; a CDR-H3 comprising the sequence set forth in SEQ ID NO:3; a CDR-L1 comprising the sequence set forth in SEQ ID NO:4; a CDR-L2 comprising the sequence set forth in SEQ ID NO:5; and a CDR-L3 comprising the sequence set forth in SEQ ID NO:6.

An antibody can comprise: a $V_H$ sequence of SEQ ID NO:7 and a $V_L$ sequence of SEQ ID NO:8.

An antibody can comprise: a heavy chain of SEQ ID NO: 17 and a light chain of SEQ ID NO:18.

An antibody can comprise: a CDR-H1 comprising the sequence set forth in SEQ ID NO:9; a CDR-H2 comprising the sequence set forth in SEQ ID NO: 10; a CDR-H3 comprising the sequence set forth in SEQ ID NO: 11; a CDR-L1 comprising the sequence set forth in SEQ ID NO:12; a CDR-L2 comprising the sequence set forth in SEQ ID NO:13; and a CDR-L3 comprising the sequence set forth in SEQ ID NO:14.

An antibody can comprise: a $V_H$ sequence of SEQ ID NO:15 and a $V_L$ sequence of SEQ ID NO:16.

An antibody can comprise: a heavy chain of SEQ ID NO:19 and a light chain of SEQ ID NO:20.

An antibody can comprise: a CDR-H1 comprising the sequence set forth in SEQ ID NO:21; a CDR-H2 comprising the sequence set forth in SEQ ID NO:22; a CDR-H3 comprising the sequence set forth in SEQ ID NO:23; a CDR-L1 comprising the sequence set forth in SEQ ID NO:24; a CDR-L2 comprising the sequence set forth in SEQ ID NO:25; and a CDR-L3 comprising the sequence set forth in SEQ ID NO:26.

An antibody can comprise: a $V_H$ sequence of SEQ ID NO:27 and a $V_L$ sequence of SEQ ID NO:28.

An antibody can comprise: a CDR-H1 comprising the sequence set forth in SEQ ID NO:29; a CDR-H2 comprising the sequence set forth in SEQ ID NO:30; a CDR-H3 comprising the sequence set forth in SEQ ID NO:31; a CDR-L1 comprising the sequence set forth in SEQ ID NO:32; a CDR-L2 comprising the sequence set forth in SEQ ID NO:33; and a CDR-L3 comprising the sequence set forth in SEQ ID NO:34.

An antibody can comprise: a $V_H$ sequence of SEQ ID NO:35 and a $V_L$ sequence of SEQ ID NO:36.

In certain aspects, an antibody can comprise one or more CDRs of 1H9. In certain aspects, an antibody can comprise all CDRs of 1H9. In certain aspects, an antibody can comprise one or more variable sequences of 1H9. In certain aspects, an antibody can comprise each variable sequence of 1H9. In certain aspects, an antibody can comprise the heavy chain of 1H9. In certain aspects, an antibody can comprise the light chain of 1H9. In certain aspects, an antibody can comprise the heavy chain and the light chain of 1H9. In certain aspects, an antibody is 1H9.

In certain aspects, an antibody can comprise one or more CDRs of 3C2. In certain aspects, an antibody can comprise all CDRs of 3C2. In certain aspects, an antibody can comprise one or more variable sequences of 3C2. In certain aspects, an antibody can comprise each variable sequence of 3C2. In certain aspects, an antibody can comprise the heavy chain of 3C2. In certain aspects, an antibody can comprise the light chain of 3C2. In certain aspects, an antibody can comprise the heavy chain and the light chain of 3C2. In certain aspects, an antibody is 3C2.

In certain aspects, an antibody can comprise one or more CDRs of 9B11. In certain aspects, an antibody can comprise all CDRs of 9B11. In certain aspects, an antibody can comprise one or more variable sequences of 9B11. In certain aspects, an antibody can comprise each variable sequence of 9B11. In certain aspects, an antibody can comprise the heavy chain of 9B11. In certain aspects, an antibody can comprise the light chain of 9B11. In certain aspects, an antibody can comprise the heavy chain and the light chain of 9B11. In certain aspects, an antibody is 9B11.

In certain aspects, an antibody can comprise one or more CDRs of 7E11. In certain aspects, an antibody can comprise all CDRs of 7E11. In certain aspects, an antibody can comprise one or more variable sequences of 7E11. In certain aspects, an antibody can comprise each variable sequence of 7E11. In certain aspects, an antibody can comprise the heavy chain of 7E11. In certain aspects, an antibody can comprise the light chain of 7E11. In certain aspects, an antibody can comprise the heavy chain and the light chain of 7E11. In certain aspects, an antibody is 7E11.

In some embodiments, an antibody provided herein comprises a sequence having at least about 50%, 60%, 70%, 80%, 90%, 95%, or 99% identity to an illustrative sequence provided in SEQ ID NOs: 1-36. In some embodiments, an antibody provided herein comprises a sequence provided in SEQ ID NOs: 1-36, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

Monospecific and Multispecific SIRP-ALPHA Antibodies

In some embodiments, the antibodies provided herein are monospecific antibodies.

In some embodiments, the antibodies provided herein are multispecific antibodies.

In some embodiments, a multispecific antibody provided herein binds more than one antigen. In some embodiments, a multispecific antibody binds 2 antigens. In some embodiments, a multispecific antibody binds 3 antigens. In some embodiments, a multispecific antibody binds 4 antigens. In some embodiments, a multispecific antibody binds 5 antigens.

In some embodiments, a multispecific antibody provided herein binds more than one epitope on a SIRP-ALPHA antigen. In some embodiments, a multispecific antibody binds 2 epitopes on a SIRP-ALPHA antigen. In some embodiments, a multispecific antibody binds 3 epitopes on a SIRP-ALPHA antigen.

Many multispecific antibody constructs are known in the art, and the antibodies provided herein may be provided in the form of any suitable multispecific suitable construct.

In some embodiments, the multispecific antibody comprises an immunoglobulin comprising at least two different heavy chain variable regions each paired with a common light chain variable region (i.e., a "common light chain antibody"). The common light chain variable region forms a distinct antigen-binding domain with each of the two different heavy chain variable regions. See Merchant et al., *Nature Biotechnol.*, 1998, 16:677-681, incorporated by reference in its entirety.

In some embodiments, the multispecific antibody comprises an immunoglobulin comprising an antibody or fragment thereof attached to one or more of the N- or C-termini of the heavy or light chains of such immunoglobulin. See Coloma and Morrison, *Nature Biotechnol.*, 1997, 15:159-163, incorporated by reference in its entirety. In some aspects, such antibody comprises a tetravalent bispecific antibody.

In some embodiments, the multispecific antibody comprises a hybrid immunoglobulin comprising at least two different heavy chain variable regions and at least two different light chain variable regions. See Milstein and Cuello, *Nature*, 1983, 305:537-540; and Staerz and Bevan, *Proc. Natl. Acad. Sci. USA*, 1986, 83:1453-1457; each of which is incorporated by reference in its entirety.

In some embodiments, the multispecific antibody comprises immunoglobulin chains with alterations to reduce the formation of side products that do not have multispecificity. In some aspects, the antibodies comprise one or more "knobs-into-holes" modifications as described in U.S. Pat. No. 5,731,168, incorporated by reference in its entirety.

In some embodiments, the multispecific antibody comprises immunoglobulin chains with one or more electrostatic modifications to promote the assembly of Fc hetero-multimers. See WO 2009/089004, incorporated by reference in its entirety.

In some embodiments, the multispecific antibody comprises a bispecific single chain molecule. See Traunecker et al., *EMBO J.*, 1991, 10:3655-3659; and Gruber et al., *J. Immunol.*, 1994, 152:5368-5374; each of which is incorporated by reference in its entirety.

In some embodiments, the multispecific antibody comprises a heavy chain variable domain and a light chain variable domain connected by a polypeptide linker, where the length of the linker is selected to promote assembly of multispecific antibody with the desired multispecificity. For example, monospecific scFvs generally form when a heavy chain variable domain and light chain variable domain are connected by a polypeptide linker of more than 12 amino acid residues. See U.S. Pat. Nos. 4,946,778 and 5,132,405, each of which is incorporated by reference in its entirety. In some embodiments, reduction of the polypeptide linker length to less than 12 amino acid residues prevents pairing of heavy and light chain variable domains on the same polypeptide chain, thereby allowing pairing of heavy and light chain variable domains from one chain with the complementary domains on another chain. The resulting antibody therefore has multispecificity, with the specificity of each binding site contributed by more than one polypeptide chain. Polypeptide chains comprising heavy and light chain variable domains that are joined by linkers between 3 and 12 amino acid residues form predominantly dimers (termed diabodies). With linkers between 0 and 2 amino acid residues, trimers (termed triabodies) and tetramers (termed tetrabodies) are favored. However, the exact type of oligomerization appears to depend on the amino acid residue composition and the order of the variable domain in each polypeptide chain (e.g., $V_H$-linker-$V_L$ vs. $V_L$-linker-$V_H$), in addition to the linker length. A skilled person can select the appropriate linker length based on the desired multispecificity.

Glycosylation and Related Variants

An antibody provided herein may be altered to increase, decrease or eliminate the extent to which it is glycosylated. Glycosylation of polypeptides is typically either "N-linked" or "O-linked." In some aspects, glycosylation of the antibody is reduced by enzymatic deglycosylation, expression in a bacterial host, or modification of an amino acid residue utilized for glycosylation. Modifications such as mutations can be used to alter glycosylation.

"N-linked" glycosylation refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site.

"O-linked" glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition or deletion of N-linked glycosylation sites to or from an antibody provided herein may be accomplished by altering the amino acid sequence such that one or more of the above-described tripeptide sequences is created or removed. Addition or deletion of O-linked glycosylation sites may be accomplished by addition, deletion, or substitution of one or more serine or threonine residues in or to (as the case may be) the sequence of an antibody.

In some embodiments, an antibody provided herein comprises a glycosylation motif that is different from a naturally occurring antibody. Any suitable naturally occurring glycosylation motif can be modified in the antibody provided herein. The structural and glycosylation properties of immunoglobulins, for example, are known in the art and summarized, for example, in Schroeder and Cavacini, *J. Allergy Clin. Immunol.*, 2010, 125:S41-52, incorporated by reference in its entirety.

In some embodiments, an antibody provided herein comprises an IgG1 Fc region with modification to the oligosaccharide attached to asparagine 297 (Asn 297). Naturally occurring IgG1 antibodies produced by mammalian cells typically comprise a branched, biantennary oligosaccharide that is generally attached by an N-linkage to Asn 297 of the $C_{H2}$ domain of the Fc region. See Wright et al., *TIBTECH*, 1997, 15:26-32, incorporated by reference in its entirety. The oligosaccharide attached to Asn 297 may include various carbohydrates such as mannose, N-acetyl glucosamine (GlcNAc), galactose, and sialic acid, as well as a fucose attached to a GlcNAc in the "stem" of the biantennary oligosaccharide structure.

In some embodiments, the oligosaccharide attached to Asn 297 is modified to create antibodies having altered ADCC. In some embodiments, the oligosaccharide is altered to improve ADCC. In some embodiments, the oligosaccharide is altered to reduce ADCC.

In some aspects, an antibody provided herein comprises an IgG1 domain with reduced fucose content at position Asn 297 compared to a naturally occurring IgG1 domain. Such Fc domains are known to have improved ADCC. See Shields et al., *J. Biol. Chem.*, 2002, 277:26733-26740, incorporated by reference in its entirety. In some aspects, such antibodies do not comprise any fucose at position Asn 297. The amount of fucose may be determined using any suitable method, for example as described in WO 2008/077546, incorporated by reference in its entirety.

In some embodiments, an antibody provided herein comprises a bisected oligosaccharide, such as a biantennary oligosaccharide attached to the Fc region of the antibody that is bisected by GlcNAc. Such antibody variants may have reduced fucosylation and/or improved ADCC function. Examples of such antibody variants are described, for example, in WO 2003/011878; U.S. Pat. No. 6,602,684; and U.S. Pat. Pub. No. 2005/0123546; each of which is incorporated by reference in its entirety.

Other illustrative glycosylation variants which may be incorporated into an antibody provided herein are described, for example, in U.S. Pat. Pub. Nos. 2003/0157108, 2004/0093621, 2003/0157108, 2003/0115614, 2002/0164328, 2004/0093621, 2004/0132140, 2004/0110704, 2004/0110282, 2004/0109865; International Pat. Pub. Nos. 2000/61739, 2001/29246, 2003/085119, 2003/084570, 2005/035586, 2005/035778; 2005/053742, 2002/031140; Okazaki et al., *J. Mol. Biol.*, 2004, 336:1239-1249; and Yamane-Ohnuki et al., *Biotech. Bioeng.*, 2004, 87: 614-622; each of which is incorporated by reference in its entirety.

In some embodiments, an antibody provided herein comprises an Fc region with at least one galactose residue in the oligosaccharide attached to the Fc region. Such antibody variants may have improved CDC function. Examples of such antibody variants are described, for example, in WO 1997/30087; WO 1998/58964; and WO 1999/22764; each of which his incorporated by reference in its entirety.

Examples of cell lines capable of producing defucosylated antibody include Lec 13 CHO cells, which are deficient in protein fucosylation (see Ripka et al., *Arch. Biochem. Biophys.*, 1986, 249:533-545; U.S. Pat. Pub. No. 2003/0157108; WO 2004/056312; each of which is incorporated by reference in its entirety), and knockout cell lines, such as alpha-1,6-fucosyltransferase gene or FUT8 knockout CHO cells (see Yamane-Ohnuki et al., *Biotech. Bioeng.*, 2004, 87: 614-622; Kanda et al., *Biotechnol. Bioeng.*, 2006, 94:680-688; and WO 2003/085107; each of which is incorporated by reference in its entirety).

In some embodiments, an antibody provided herein is an aglycosylated antibody. An aglycosylated antibody can be produced using any method known in the art or described herein. In some aspects, an aglycosylated antibody is produced by modifying the antibody to remove all glycosylation sites. In some aspects, the glycosylation sites are removed only from the Fc region of the antibody. In some aspects, an aglycosylated antibody is produced by expressing the antibody in an organism that is not capable of glycosylation, such as *E. coli*, or by expressing the antibody in a cell-free reaction mixture.

In some embodiments, an antibody provided herein has a constant region with reduced effector function compared to a native IgG1 antibody. In some embodiments, the affinity of a constant region of an Fc region of an antibody provided herein for Fc receptor is less than the affinity of a native IgG1 constant region for such Fc receptor.

Fc Region and Variants

In certain embodiments, an antibody provided herein comprises an Fc region. In certain embodiments, an antibody provided herein comprises an Fc region with one or more amino acid substitutions, insertions, or deletions in comparison to a naturally occurring Fc region. In some aspects, such substitutions, insertions, or deletions yield antibody with altered stability, glycosylation, or other characteristics. In some aspects, such substitutions, insertions, or deletions yield aglycosylated antibody.

A "variant Fc region" or "engineered Fc region" comprises an amino acid sequence that differs from that of a native-sequence Fc region by virtue of at least one amino acid modification, preferably one or more amino acid substitution(s). Preferably, the variant Fc region has at least one amino acid substitution compared to a native-sequence Fc region or to the Fc region of a parent polypeptide, e.g., from about one to about ten amino acid substitutions, and preferably from about one to about five amino acid substitutions in a native-sequence Fc region or in the Fc region of the parent polypeptide. The variant Fc region herein will preferably possess at least about 80% homology with a native-sequence Fc region and/or with an Fc region of a parent polypeptide, and most preferably at least about 90% homology therewith, more preferably at least about 95% homology therewith.

Variant Fc sequences for a "dead Fc" can include three amino acid substitutions in the CH2 region to reduce FcγRI binding at EU index positions 234, 235, and 237 (see Duncan et al., (1988) Nature 332:563). Two amino acid substitutions in the complement C1q binding site at EU index positions 330 and 331 reduce complement fixation (see Tao et al., J. Exp. Med. 178:661 (1993) and Canfield and Morrison, J. Exp. Med. 173:1483 (1991)). Substitution into human IgG1 of IgG2 residues at positions 233-236 and IgG4 residues at positions 327, 330 and 331 greatly reduces ADCC and CDC (see, for example, Armour K L. et al., 1999 Eur J Immunol. 29(8):2613-24; and Shields R L. et al., 2001. J Biol Chem. 276(9):6591-604).

Binding of IgG to the FcγRs or C1q depends on residues located in the hinge region and the CH2 domain. Two regions of the CH2 domain are critical for FcγRs and C1q binding, and have unique sequences in IgG2 and IgG4. Substitutions into human IgG1 or IgG2 residues at positions 233-236 and IgG4 residues at positions 327, 330 and 331 have been shown to greatly reduce ADCC and CDC. Numerous mutations have been made in the CH2 domain of human IgG1.

The triple amino acid substitution L234A, L235A, and G237A largely eliminates FcγR and complement effector functions (see, for example, US20100266505).

In some embodiments the Fc region has been modified by the choice of expression host, enzymatic treatment of amino acid substitutions to have reduced glycosylation and binding to FcγR, relative to the native protein. Mutations that reduce binding to FcγR include, without limitation, modification of the glycosylation on asparagine 297 of the Fc domain, which is known to be required for optimal FcR interaction. For example known amino acid substitutions include N297A or N297G, which results in the loss of a glycosylation site on the protein. Enzymatically deglycosylated Fc domains, recombinantly expressed antibodies in the presence of a glycosylation inhibitor and the expression of Fc domains in bacteria have a similar loss of glycosylation and consequent binding to FcγRs.

The LALA variant, L234A/L235A, also has significantly reduced FcγR binding; as does E233P/L234V/L235A/G236+A327G/A330S/P331S. See, for example, Armour et al. (1999) Eur J Immunol. 29(8):2613-24. The set of mutations: K322A, L234A and L235A are sufficient to almost completely abolish FcγR and C1q binding. A set of three mutations, L234F/L235E/P331S (Dubbed™), have a very similar effect.

Other Fc variants are possible, including without limitation one in which a region capable of forming a disulfide bond is deleted, or in which certain amino acid residues are eliminated at the N-terminal end of a native Fc form or a methionine residue is added thereto.

The Fc may be in the form of having native sugar chains, increased sugar chains compared to a native form or decreased sugar chains compared to the native form, or may be in an aglycosylated or deglycosylated form. The increase, decrease, removal or other modification of the sugar chains may be achieved by methods common in the art, such as a chemical method, an enzymatic method or by expressing it in a genetically engineered production cell line. Such cell lines can include microorganisms, e.g. *Pichia Pastoris*, and mammalians cell line, e.g. CHO cells, that naturally express glycosylating enzymes. Further, microorganisms or cells can be engineered to express glycosylating enzymes, or can be rendered unable to express glycosylation enzymes (See e.g., Hamilton, et al., Science, 313:1441 (2006); Kanda, et al, J. Biotechnology, 130:300 (2007); Kitagawa, et al., J. Biol. Chem., 269 (27): 17872 (1994); Ujita-Lee et al., J. Biol. Chem., 264 (23): 13848 (1989); Imai-Nishiya, et al, BMC Biotechnology 7:84 (2007); and WO 07/055916). As one example of a cell engineered to have altered sialylation activity, the alpha-2,6-sialyltransferase 1 gene has been engineered into Chinese Hamster Ovary cells and into sf9 cells. Antibodies expressed by these engineered cells are thus sialylated by the exogenous gene product. A further method for obtaining Fc molecules having a modified amount of sugar residues compared to a plurality of native molecules includes separating said plurality of molecules into glycosylated and non-glycosylated fractions, for example, using lectin affinity chromatography (See e.g., WO 07/117505). The presence of particular glycosylation moieties has been shown to alter the function of Immunoglobulins. For example, the removal of sugar chains from an Fc molecule results in a sharp decrease in binding affinity to the C1q part of the first complement component C1 and a decrease or loss in antibody-dependent cell-mediated cytotoxicity (ADCC) or complement-dependent cytotoxicity (CDC), thereby not inducing unnecessary immune responses in vivo. Additional important modifications include sialylation and fucosylation: the presence of sialic acid in IgG has been correlated with anti-inflammatory activity (See e.g., Kaneko, et al, Science 313:760 (2006)), whereas removal of fucose from the IgG leads to enhanced ADCC activity (See e.g., Shoj-Hosaka, et al, J. Biochem., 140:777 (2006)).

The term "Fc-region-comprising antibody" refers to an antibody that comprises an Fc region. The C-terminal lysine (residue 447 according to the EU numbering system) of the Fc region may be removed, for example, during purification of the antibody or by recombinant engineering the nucleic acid encoding the antibody. Accordingly, an antibody having an Fc region can comprise an antibody with or without K447.

In some aspects, the Fc region of an antibody provided herein is modified to yield an antibody with altered affinity for an Fc receptor, or an antibody that is more immunologically inert. In some embodiments, the antibody variants provided herein possess some, but not all, effector functions. Such antibodies may be useful, for example, when the half-life of the antibody is important in vivo, but when certain effector functions (e.g., complement activation and ADCC) are unnecessary or deleterious.

In some embodiments, the Fc region of an antibody provided herein is a human IgG4 Fc region comprising one or more of the hinge stabilizing mutations S228P and L235E. See Aalberse et al., *Immunology*, 2002, 105:9-19, incorporated by reference in its entirety. In some embodiments, the IgG4 Fc region comprises one or more of the following mutations: E233P, F234V, and L235A. See Armour et al., *Mol. Immunol.*, 2003, 40:585-593, incorporated by reference in its entirety. In some embodiments, the IgG4 Fc region comprises a deletion at position G236.

In some embodiments, the Fc region of an antibody provided herein is a human IgG1 Fc region comprising one or more mutations to reduce Fc receptor binding. In some aspects, the one or more mutations are in residues selected from S228 (e.g., S228A), L234 (e.g., L234A), L235 (e.g., L235A), D265 (e.g., D265A), and N297 (e.g., N297A). In some aspects, the antibody comprises a PVA236 mutation. PVA236 means that the amino acid sequence ELLG (SEQ ID NO: 51), from amino acid position 233 to 236 of IgG1 or EFLG (SEQ ID NO: 52) of IgG4, is replaced by PVA. See U.S. Pat. No. 9,150,641, incorporated by reference in its entirety.

In some embodiments, the Fc region of an antibody provided herein is modified as described in Armour et al., *Eur. J. Immunol.*, 1999, 29:2613-2624; WO 1999/058572; and/or U.K. Pat. App. No. 98099518; each of which is incorporated by reference in its entirety.

In some embodiments, the Fc region of an antibody provided herein is a human IgG2 Fc region comprising one or more of mutations A330S and P331S.

In some embodiments, the Fc region of an antibody provided herein has an amino acid substitution at one or more positions selected from 238, 265, 269, 270, 297, 327 and 329. See U.S. Pat. No. 6,737,056, incorporated by reference in its entirety. Such Fc mutants include Fc mutants with substitutions at two or more of amino acid positions 265, 269, 270, 297 and 327, including the so-called "DANA" Fc mutant with substitution of residues 265 and 297 with alanine. See U.S. Pat. No. 7,332,581, incorporated by reference in its entirety. In some embodiments, the antibody comprises an alanine at amino acid position 265. In some embodiments, the antibody comprises an alanine at amino acid position 297.

In certain embodiments, an antibody provided herein comprises an Fc region with one or more amino acid substitutions which improve ADCC, such as a substitution at one or more of positions 298, 333, and 334 of the Fc region. In some embodiments, an antibody provided herein comprises an Fc region with one or more amino acid substitutions at positions 239, 332, and 330, as described in Lazar et al., *Proc. Natl. Acad. Sci. USA*, 2006, 103:4005-4010, incorporated by reference in its entirety.

In some embodiments, an antibody provided herein comprises one or more alterations that improves or diminishes C1q binding and/or CDC. See U.S. Pat. No. 6,194,551; WO 99/51642; and Idusogie et al., *J. Immunol.*, 2000, 164:4178-4184; each of which is incorporated by reference in its entirety.

In some embodiments, an antibody provided herein comprises one or more alterations to increase half-life. Antibodies with increased half-lives and improved binding to the neonatal Fc receptor (FcRn) are described, for example, in Hinton et al., *J. Immunol.*, 2006, 176:346-356; and U.S. Pat. Pub. No. 2005/0014934; each of which is incorporated by reference in its entirety. Such Fc variants include those with substitutions at one or more of Fc region residues: 238, 250, 256, 265, 272, 286, 303, 305, 307, 311, 312, 314, 317, 340, 356, 360, 362, 376, 378, 380, 382, 413, 424, 428, and 434 of an IgG.

In some embodiments, an antibody provided herein comprises one or more Fc region variants as described in U.S. Pat. Nos. 7,371,826 5,648,260, and 5,624,821; Duncan and Winter, *Nature*, 1988, 322:738-740; and WO 94/29351; each of which is incorporated by reference in its entirety.

Nucleotides, Vectors, Host Cells, and Related Methods

Also provided are isolated nucleic acids encoding SIRP-ALPHA antibodies, vectors comprising the nucleic acids, and host cells comprising the vectors and nucleic acids, as well as recombinant techniques for the production of the antibodies.

In some embodiments, a nucleic acid sequence is provided that encodes a sequence having at least about 50%, 60%, 70%, 80%, 90%, 95%, or 99% identity to an illustrative sequence provided in SEQ ID NOs: 1-36. In some embodiments, a nucleic acid sequence is provided that encodes a sequence provided in SEQ ID NOs: 1-36, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some embodiments, an antibody provided herein comprises a sequence having at least about 50%, 60%, 70%, 80%, 90%, 95%, or 99% identity to an illustrative sequence provided in SEQ ID NOs: 37-44. In some embodiments, an antibody provided herein comprises a sequence provided in SEQ ID NOs: 37-44, with up to 1, 2, 3, 4, 5, 6, 7, 8, 9, 10, 11, 12, 13, 14, 15, 16, 17, 18, 19, 20, 21, 22, 23, 24, or 25 mutations. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

For recombinant production of an antibody, the nucleic acid(s) encoding it may be isolated and inserted into a replicable vector for further cloning (i.e., amplification of the DNA) or expression. In some aspects, the nucleic acid may be produced by homologous recombination, for example as described in U.S. Pat. No. 5,204,244, incorporated by reference in its entirety.

Many different vectors are known in the art. The vector components generally include one or more of the following: a signal sequence, an origin of replication, one or more marker genes, an enhancer element, a promoter, and a transcription termination sequence, for example as described in U.S. Pat. No. 5,534,615, incorporated by reference in its entirety.

Illustrative examples of suitable host cells are provided below. These host cells are not meant to be limiting, and any suitable host cell may be used to produce the antibodies provided herein.

Suitable host cells include any prokaryotic (e.g., bacterial), lower eukaryotic (e.g., yeast), or higher eukaryotic (e.g., mammalian) cells. Suitable prokaryotes include eubacteria, such as Gram-negative or Gram-positive organisms, for example, Enterobacteriaceae such as *Escherichia* (*E. coli*), *Enterobacter*, *Erwinia*, *Klebsiella*, *Proteus*, *Salmonella* (*S. typhimurium*), *Serratia* (*S. marcescans*), *Shigella*, *Bacilli* (*B. subtilis* and *B. licheniformis*), *Pseudomonas* (*P. aeruginosa*), and *Streptomyces*. One useful *E. coli* cloning host is *E. coli* 294, although other strains such as *E. coli* B, *E. coli* X1776, and *E. coli* W3110 are also suitable.

In addition to prokaryotes, eukaryotic microbes such as filamentous fungi or yeast are also suitable cloning or expression hosts for SIRP-ALPHA antibody-encoding vectors. *Saccharomyces cerevisiae*, or common baker's yeast, is a commonly used lower eukaryotic host microorganism. However, a number of other genera, species, and strains are available and useful, such as *Schizosaccharomyces pombe*, *Kluyveromyces* (*K. lactis*, *K. fragilis*, *K. bulgaricus K. wickeramii*, *K. waltii*, *K. drosophilarum*, *K. thermotolerans*, and *K. marxianus*), *Yarrowia*, *Pichia pastoris*, *Candida* (*C. albicans*), *Trichoderma reesia*, *Neurospora crassa*, *Schwanniomyces* (*S. occidentalis*), and filamentous fungi such as, for example *Penicillium*, *Tolypocladium*, and *Aspergillus* (*A. nidulans* and *A. niger*).

Useful mammalian host cells include COS-7 cells, HEK293 cells; baby hamster kidney (BHK) cells; Chinese hamster ovary (CHO); mouse sertoli cells; African green monkey kidney cells (VERO-76), and the like.

The host cells used to produce the SIRP-ALPHA antibody may be cultured in a variety of media. Commercially available media such as, for example, Ham's F10, Minimal Essential Medium (MEM), RPMI-1640, and Dulbecco's Modified Eagle's Medium (DMEM) are suitable for culturing the host cells. In addition, any of the media described in Ham et al., *Meth. Enz.,* 1979, 58:44; Barnes et al., *Anal. Biochem.,* 1980, 102:255; and U.S. Pat. Nos. 4,767,704, 4,657,866, 4,927,762, 4,560,655, and 5,122,469; or WO 90/03430 and WO 87/00195 may be used. Each of the foregoing references is incorporated by reference in its entirety.

Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics, trace elements (defined as inorganic compounds usually present at final concentrations in the micromolar range), and glucose or an equivalent energy source. Any other necessary supplements may also be included at appropriate concentrations that would be known to those skilled in the art.

The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. For example, Carter et al. (*Bio/Technology,* 1992, 10:163-167, incorporated by reference in its entirety) describes a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation.

In some embodiments, the antibody is produced in a cell-free system. In some aspects, the cell-free system is an in vitro transcription and translation system as described in Yin et al., *mAbs,* 2012, 4:217-225, incorporated by reference in its entirety. In some aspects, the cell-free system utilizes a cell-free extract from a eukaryotic cell or from a prokaryotic cell. In some aspects, the prokaryotic cell is *E. coli*. Cell-free expression of the antibody may be useful, for example, where the antibody accumulates in a cell as an insoluble aggregate, or where yields from periplasmic expression are low.

Where the antibody is secreted into the medium, supernatants from such expression systems are generally first concentrated using a commercially available protein concentration filter, for example, an Amicon® or Millipore® Pellcon® ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a particularly useful purification technique. The suitability of protein A as an affinity ligand depends on the species and isotype of any immunoglobulin Fc domain that is present in the antibody. Protein A can be used to purify antibodies that comprise human γ1, γ2, or γ4 heavy chains (Lindmark et al., *J. Immunol. Meth.,* 1983, 62:1-13, incorporated by reference in its entirety). Protein G is useful for all mouse isotypes and for human $\gamma^3$ (Guss et al., *EMBO J.,* 1986, 5:1567-1575, incorporated by reference in its entirety).

The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the BakerBond ABX® resin is useful for purification.

Other techniques for protein purification, such as fractionation on an ion-exchange column, ethanol precipitation, Reverse Phase HPLC, chromatography on silica, chromatography on heparin Sepharose®, chromatofocusing, SDS-PAGE, and ammonium sulfate precipitation are also available, and can be applied by one of skill in the art.

Following any preliminary purification step(s), the mixture comprising the antibody of interest and contaminants may be subjected to low pH hydrophobic interaction chromatography using an elution buffer at a pH between about 2.5 to about 4.5, generally performed at low salt concentrations (e.g., from about 0 to about 0.25 M salt).

Methods of Making SIRP-ALPHA Antibodies

SIRP-ALPHA Antigen Preparation

The SIRP-ALPHA antigen used for isolation or creation of the antibodies provided herein may be intact SIRP-ALPHA or a fragment of SIRP-ALPHA. The SIRP-ALPHA antigen may be, for example, in the form of an isolated protein or a protein expressed on the surface of a cell.

In some embodiments, the SIRP-ALPHA antigen is a non-naturally occurring variant of SIRP-ALPHA, such as a SIRP-ALPHA protein having an amino acid sequence or post-translational modification that does not occur in nature.

In some embodiments, the SIRP-ALPHA antigen is truncated by removal of, for example, intracellular or membrane-spanning sequences, or signal sequences. In some embodiments, the SIRP-ALPHA antigen is fused at its C-terminus to a human IgG1 Fc domain or a polyhistidine tag.

Methods of Making Monoclonal Antibodies

Monoclonal antibodies may be obtained, for example, using the hybridoma method first described by Kohler et al., *Nature,* 1975, 256:495-497 (incorporated by reference in its entirety), and/or by recombinant DNA methods (see e.g., U.S. Pat. No. 4,816,567, incorporated by reference in its entirety). Monoclonal antibodies may also be obtained, for example, using phage or yeast-based libraries. See e.g., U.S. Pat. Nos. 8,258,082 and 8,691,730, each of which is incorporated by reference in its entirety.

In the hybridoma method, a mouse or other appropriate host animal is immunized to elicit lymphocytes that produce or are capable of producing antibodies that will specifically bind to the protein used for immunization. Alternatively, lymphocytes may be immunized in vitro. Lymphocytes are then fused with myeloma cells using a suitable fusing agent, such as polyethylene glycol, to form a hybridoma cell. See Goding J. W., *Monoclonal Antibodies: Principles and Practice* $3^{rd}$ ed. (1986) Academic Press, San Diego, Calif., incorporated by reference in its entirety.

The hybridoma cells are seeded and grown in a suitable culture medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Useful myeloma cells are those that fuse efficiently, support stable high-level production of antibody by the selected antibody-producing cells, and are sensitive media conditions, such as the presence or absence of HAT medium. Among these, preferred myeloma cell lines are murine myeloma lines, such as those derived from MOP-21 and MC-11 mouse tumors (available from the Salk Institute Cell Distribution Center, San Diego, Calif.), and SP-2 or X63-Ag8-653 cells (available from the American Type Culture Collection, Rockville, Md.). Human myeloma and mouse-human heteromyeloma cell lines also have been described for the production of human monoclonal antibodies. See e.g., Kozbor, *J. Immunol.*, 1984, 133:3001, incorporated by reference in its entirety.

After the identification of hybridoma cells that produce antibodies of the desired specificity, affinity, and/or biological activity, selected clones may be subcloned by limiting dilution procedures and grown by standard methods. See Goding, supra. Suitable culture media for this purpose include, for example, D-MEM or RPMI-1640 medium. In addition, the hybridoma cells may be grown in vivo as ascites tumors in an animal.

DNA encoding the monoclonal antibodies may be readily isolated and sequenced using conventional procedures (e.g., by using oligonucleotide probes that are capable of binding specifically to genes encoding the heavy and light chains of the monoclonal antibodies). Thus, the hybridoma cells can serve as a useful source of DNA encoding antibodies with the desired properties. Once isolated, the DNA may be placed into expression vectors, which are then transfected into host cells such as bacteria (e.g., *E. coli*), yeast (e.g., *Saccharomyces* or *Pichia* sp.), COS cells, Chinese hamster ovary (CHO) cells, or myeloma cells that do not otherwise produce antibody, to produce the monoclonal antibodies.

Methods of Making Chimeric Antibodies

Illustrative methods of making chimeric antibodies are described, for example, in U.S. Pat. No. 4,816,567; and Morrison et al., *Proc. Natl. Acad. Sci. USA*, 1984, 81:6851-6855; each of which is incorporated by reference in its entirety. In some embodiments, a chimeric antibody is made by using recombinant techniques to combine a non-human variable region (e.g., a variable region derived from a mouse, rat, hamster, rabbit, or non-human primate, such as a monkey) with a human constant region.

Methods of Making Humanized Antibodies

Humanized antibodies may be generated by replacing most, or all, of the structural portions of a non-human monoclonal antibody with corresponding human antibody sequences. Consequently, a hybrid molecule is generated in which only the antigen-specific variable, or CDR, is composed of non-human sequence. Methods to obtain humanized antibodies include those described in, for example, Winter and Milstein, *Nature*, 1991, 349:293-299; Rader et al., *Proc. Nat. Acad. Sci. U.S.A.*, 1998, 95:8910-8915; Steinberger et al., *J. Biol. Chem.*, 2000, 275:36073-36078; Queen et al., *Proc. Natl. Acad. Sci. U.S.A.*, 1989, 86:10029-10033; and U.S. Pat. Nos. 5,585,089, 5,693,761, 5,693,762, and 6,180,370; each of which is incorporated by reference in its entirety.

Methods of Making Human Antibodies

Human antibodies can be generated by a variety of techniques known in the art, for example by using transgenic animals (e.g., humanized mice). See, e.g., Jakobovits et al., *Proc. Natl. Acad. Sci. U.S.A.*, 1993, 90:2551; Jakobovits et al., *Nature*, 1993, 362:255-258; Bruggermann et al., *Year in Immuno.*, 1993, 7:33; and U.S. Pat. Nos. 5,591,669, 5,589,369 and 5,545,807; each of which is incorporated by reference in its entirety. Human antibodies can also be derived from phage-display libraries (see e.g., Hoogenboom et al., *J. Mol. Biol.*, 1991, 227:381-388; Marks et al., *J. Mol. Biol.*, 1991, 222:581-597; and U.S. Pat. Nos. 5,565,332 and 5,573,905; each of which is incorporated by reference in its entirety). Human antibodies may also be generated by in vitro activated B cells (see e.g., U.S. Pat. Nos. 5,567,610 and 5,229,275, each of which is incorporated by reference in its entirety). Human antibodies may also be derived from yeast-based libraries (see e.g., U.S. Pat. No. 8,691,730, incorporated by reference in its entirety).

Methods of Making Antibody Fragments

The antibody fragments provided herein may be made by any suitable method, including the illustrative methods described herein or those known in the art. Suitable methods include recombinant techniques and proteolytic digestion of whole antibodies. Illustrative methods of making antibody fragments are described, for example, in Hudson et al., Nat. Med., 2003, 9:129-134, incorporated by reference in its entirety. Methods of making scFv antibodies are described, for example, in Plückthun, in *The Pharmacology of Monoclonal Antibodies*, vol. 113, Rosenburg and Moore eds., Springer-Verlag, New York, pp. 269-315 (1994); WO 93/16185; and U.S. Pat. Nos. 5,571,894 and 5,587,458; each of which is incorporated by reference in its entirety.

Methods of Making Alternative Scaffolds

The alternative scaffolds provided herein may be made by any suitable method, including the illustrative methods described herein or those known in the art. For example, methods of preparing Adnectins™ are described in Emanuel et al., *mAbs*, 2011, 3:38-48, incorporated by reference in its entirety. Methods of preparing iMabs are described in U.S. Pat. Pub. No. 2003/0215914, incorporated by reference in its entirety. Methods of preparing Anticalins® are described in Vogt and Skerra, *Chem. Biochem.*, 2004, 5:191-199, incorporated by reference in its entirety. Methods of preparing Kunitz domains are described in Wagner et al., *Biochem. & Biophys. Res. Comm.*, 1992, 186:118-1145, incorporated by reference in its entirety. Methods of preparing thioredoxin peptide aptamers are provided in Geyer and Brent, *Meth. Enzymol.*, 2000, 328:171-208, incorporated by reference in its entirety. Methods of preparing Affibodies are provided in Fernandez, *Curr. Opinion in Biotech.*, 2004, 15:364-373, incorporated by reference in its entirety. Methods of preparing DARPins are provided in Zahnd et al., *J. Mol. Biol.*, 2007, 369:1015-1028, incorporated by reference in its entirety. Methods of preparing Affilins are provided in Ebersbach et al., *J. Mol. Biol.*, 2007, 372:172-185, incorporated by reference in its entirety. Methods of preparing Tetranectins are provided in Graversen et al., *J. Biol. Chem.*, 2000, 275:37390-37396, incorporated by reference in its entirety. Methods of preparing Avimers are provided in Silverman et al., *Nature Biotech.*, 2005, 23:1556-1561, incorporated by reference in its entirety. Methods of preparing Fynomers are provided in Silacci et al., *J. Biol. Chem.*, 2014, 289:14392-14398, incorporated by reference in its entirety. Further information on alternative scaffolds is provided in Binz et al., *Nat. Biotechnol.*, 2005 23:1257-1268; and Skerra, *Current Opin. in Biotech.*, 2007 18:295-304, each of which is incorporated by reference in its entirety.

Methods of Making Multispecific Antibodies

The multispecific antibodies provided herein may be made by any suitable method, including the illustrative methods described herein or those known in the art. Methods of making common light chain antibodies are described in Merchant et al., *Nature Biotechnol.*, 1998, 16:677-681, incorporated by reference in its entirety. Methods of making tetravalent bispecific antibodies are described in Coloma and Morrison, *Nature Biotechnol.*, 1997, 15:159-163, incorporated by reference in its entirety. Methods of making hybrid immunoglobulins are described in Milstein and Cuello, *Nature*, 1983, 305:537-540; and Staerz and Bevan, *Proc. Natl. Acad. Sci. USA*, 1986, 83:1453-1457; each of which is incorporated by reference in its entirety. Methods of making immunoglobulins with knobs-into-holes modification are described in U.S. Pat. No. 5,731,168, incorporated by reference in its entirety. Methods of making immunoglobulins with electrostatic modifications are provided in WO 2009/089004, incorporated by reference in its entirety. Methods of making bispecific single chain antibodies are described in Traunecker et al., *EMBO J.*, 1991, 10:3655-3659; and Gruber et al., *J. Immunol.*, 1994, 152:5368-5374; each of which is incorporated by reference in its entirety. Methods of making single-chain antibodies, whose linker length may be varied, are described in U.S. Pat. Nos. 4,946,778 and 5,132,405, each of which is incorporated by reference in its entirety. Methods of making diabodies are described in Hollinger et al., *Proc. Natl. Acad. Sci. USA*, 1993, 90:6444-6448, incorporated by reference in its entirety. Methods of making triabodies and tetrabodies are described in Todorovska et al., *J. Immunol. Methods*, 2001, 248:47-66, incorporated by reference in its entirety. Methods of making trispecific F(ab')3 derivatives are described in Tutt et al. *J. Immunol.*, 1991, 147:60-69, incorporated by reference in its entirety. Methods of making cross-linked antibodies are described in U.S. Pat. No. 4,676,980; Brennan et al., *Science*, 1985, 229:81-83; Staerz, et al. *Nature*, 1985, 314:628-631; and EP 0453082; each of which is incorporated by reference in its entirety. Methods of making antigen-binding domains assembled by leucine zippers are described in Kostelny et al., *J. Immunol.*, 1992, 148:1547-1553, incorporated by reference in its entirety. Methods of making antibodies via the DNL approach are described in U.S. Pat. Nos. 7,521,056; 7,550,143; 7,534,866; and 7,527,787; each of which is incorporated by reference in its entirety. Methods of making hybrids of antibody and non-antibody molecules are described in WO 93/08829, incorporated by reference in its entirety, for examples of such antibodies. Methods of making DAF antibodies are described in U.S. Pat. Pub. No. 2008/0069820, incorporated by reference in its entirety. Methods of making antibodies via reduction and oxidation are described in Carlring et al., *PLoS One*, 2011, 6:e22533, incorporated by reference in its entirety. Methods of making DVD-Igs™ are described in U.S. Pat. No. 7,612,181, incorporated by reference in its entirety. Methods of making DARTs™ are described in Moore et al., *Blood*, 2011, 117:454-451, incorporated by reference in its entirety. Methods of making DuoBodies® are described in Labrijn et al., *Proc. Natl. Acad. Sci. USA*, 2013, 110:5145-5150; Gramer et al., *mAbs*, 2013, 5:962-972; and Labrijn et al., *Nature Protocols*, 2014, 9:2450-2463; each of which is incorporated by reference in its entirety. Methods of making antibodies comprising scFvs fused to the C-terminus of the $C_{H3}$ from an IgG are described in Coloma and Morrison, *Nature Biotechnol.*, 1997, 15:159-163, incorporated by reference in its entirety. Methods of making antibodies in which a Fab molecule is attached to the constant region of an immunoglobulin are described in Miler et al., *J. Immunol.*, 2003, 170:4854-4861, incorporated by reference in its entirety. Methods of making CovX-Bodies are described in Doppalapudi et al., *Proc. Natl. Acad. Sci. USA*, 2010, 107:22611-22616, incorporated by reference in its entirety. Methods of making Fcab antibodies are described in Wozniak-Knopp et al., *Protein Eng. Des. Sel.*, 2010, 23:289-297, incorporated by reference in its entirety. Methods of making TandAb® antibodies are described in Kipriyanov et al., *J. Mol. Biol.*, 1999, 293:41-56 and Zhukovsky et al., *Blood*, 2013, 122:5116, each of which is incorporated by reference in its entirety. Methods of making tandem Fabs are described in WO 2015/103072, incorporated by reference in its entirety. Methods of making Zybodies™ are described in LaFleur et al., *mAbs*, 2013, 5:208-218, incorporated by reference in its entirety.

Methods of Making Variants

Any suitable method can be used to introduce variability into a polynucleotide sequence(s) encoding an antibody, including error-prone PCR, chain shuffling, and oligonucleotide-directed mutagenesis such as trinucleotide-directed mutagenesis (TRIM). In some aspects, several CDR residues (e.g., 4-6 residues at a time) are randomized. CDR residues involved in antigen binding may be specifically identified, for example, using alanine scanning mutagenesis or modeling. CDR-H3 and CDR-L3 in particular are often targeted for mutation.

The introduction of diversity into the variable regions and/or CDRs can be used to produce a secondary library. The secondary library is then screened to identify antibody variants with improved affinity. Affinity maturation by constructing and reselecting from secondary libraries has been described, for example, in Hoogenboom et al., *Methods in Molecular Biology*, 2001, 178:1-37, incorporated by reference in its entirety.

Assays

A variety of assays known in the art may be used to identify and characterize an SIRP-ALPHA antibody provided herein.

Binding, Competition, and Epitope Mapping Assays

Specific antigen-binding activity of an antibody provided herein may be evaluated by any suitable method, including using SPR, BLI, RIA and MSD-SET, as described elsewhere in this disclosure. Additionally, antigen-binding activity may be evaluated by ELISA assays and Western blot assays.

Assays for measuring competition between two antibodies, or an antibody and another molecule (e.g., one or more ligands of SIRP-ALPHA) are described elsewhere in this disclosure and, for example, in Harlow and Lane, *Antibodies: A Laboratory Manual* ch. 14, 1988, Cold Spring Harbor Laboratory, Cold Spring Harbor, N.Y., incorporated by reference in its entirety.

Assays for mapping the epitopes to which an antibody provided herein bind are described, for example, in Morris "Epitope Mapping Protocols," in *Methods in Molecular Biology* vol. 66, 1996, Humana Press, Totowa, N.J., incorporated by reference in its entirety. In some embodiments, the epitope is determined by peptide competition. In some embodiments, the epitope is determined by mass spectrometry. In some embodiments, the epitope is determined by crystallography.

Assays for Effector Functions

Effector function following treatment with an antibody provided herein may be evaluated using a variety of in vitro and in vivo assays known in the art, including those described in Ravetch and Kinet, *Annu. Rev. Immunol.*, 1991, 9:457-492; U.S. Pat. Nos. 5,500,362, 5,821,337; Hellstrom et al., *Proc. Nat'l Acad. Sci. USA,* 1986, 83:7059-7063; Hellstrom et al., *Proc. Nat'l Acad. Sci. USA,* 1985, 82:1499-1502; Bruggemann et al., *J. Exp. Med.,* 1987, 166:1351-1361; Clynes et al., *Proc. Nat'l Acad. Sci. USA,* 1998, 95:652-656; WO 2006/029879; WO 2005/100402; Gazzano-Santoro et al., *J. Immunol. Methods,* 1996, 202:163-171; Cragg et al., *Blood,* 2003, 101:1045-1052; Cragg et al. *Blood,* 2004, 103:2738-2743; and Petkova et al., *Int'l. Immunol.,* 2006, 18:1759-1769; each of which is incorporated by reference in its entirety.

Pharmaceutical Compositions

An antibody provided herein can be formulated in any appropriate pharmaceutical composition and administered by any suitable route of administration. Suitable routes of administration include, but are not limited to, the intraarterial, intradermal, intramuscular, intraperitoneal, intravenous, nasal, parenteral, pulmonary, and subcutaneous routes.

The pharmaceutical composition may comprise one or more pharmaceutical excipients. Any suitable pharmaceutical excipient may be used, and one of ordinary skill in the art is capable of selecting suitable pharmaceutical excipients. Accordingly, the pharmaceutical excipients provided below are intended to be illustrative, and not limiting. Additional pharmaceutical excipients include, for example, those described in the *Handbook of Pharmaceutical Excipients,* Rowe et al. (Eds.) 6th Ed. (2009), incorporated by reference in its entirety.

In some embodiments, the pharmaceutical composition comprises an anti-foaming agent. Any suitable anti-foaming agent may be used. In some aspects, the anti-foaming agent is selected from an alcohol, an ether, an oil, a wax, a silicone, a surfactant, and combinations thereof. In some aspects, the anti-foaming agent is selected from a mineral oil, a vegetable oil, ethylene bis stearamide, a paraffin wax, an ester wax, a fatty alcohol wax, a long chain fatty alcohol, a fatty acid soap, a fatty acid ester, a silicon glycol, a fluorosilicone, a polyethylene glycol-polypropylene glycol copolymer, polydimethylsiloxane-silicon dioxide, ether, octyl alcohol, capryl alcohol, sorbitan trioleate, ethyl alcohol, 2-ethylhexanol, dimethicone, oleyl alcohol, simethicone, and combinations thereof.

In some embodiments, the pharmaceutical composition comprises a cosolvent. Illustrative examples of cosolvents include ethanol, poly(ethylene) glycol, butylene glycol, dimethylacetamide, glycerin, propylene glycol, and combinations thereof.

In some embodiments, the pharmaceutical composition comprises a buffer. Illustrative examples of buffers include acetate, borate, carbonate, lactate, malate, phosphate, citrate, hydroxide, diethanolamine, monoethanolamine, glycine, methionine, guar gum, monosodium glutamate, and combinations thereof.

In some embodiments, the pharmaceutical composition comprises a carrier or filler. Illustrative examples of carriers or fillers include lactose, maltodextrin, mannitol, sorbitol, chitosan, stearic acid, xanthan gum, guar gum, and combinations thereof.

In some embodiments, the pharmaceutical composition comprises a surfactant. Illustrative examples of surfactants include d-alpha tocopherol, benzalkonium chloride, benzethonium chloride, cetrimide, cetylpyridinium chloride, docusate sodium, glyceryl behenate, glyceryl monooleate, lauric acid, macrogol 15 hydroxystearate, myristyl alcohol, phospholipids, polyoxyethylene alkyl ethers, polyoxyethylene sorbitan fatty acid esters, polyoxyethylene stearates, polyoxylglycerides, sodium lauryl sulfate, sorbitan esters, vitamin E polyethylene(glycol) succinate, and combinations thereof.

In some embodiments, the pharmaceutical composition comprises an anti-caking agent. Illustrative examples of anti-caking agents include calcium phosphate (tribasic), hydroxymethyl cellulose, hydroxypropyl cellulose, magnesium oxide, and combinations thereof.

Other excipients that may be used with the pharmaceutical compositions include, for example, albumin, antioxidants, antibacterial agents, antifungal agents, bioabsorbable polymers, chelating agents, controlled release agents, diluents, dispersing agents, dissolution enhancers, emulsifying agents, gelling agents, ointment bases, penetration enhancers, preservatives, solubilizing agents, solvents, stabilizing agents, sugars, and combinations thereof. Specific examples of each of these agents are described, for example, in the *Handbook of Pharmaceutical Excipients,* Rowe et al. (Eds.) 6th Ed. (2009), The Pharmaceutical Press, incorporated by reference in its entirety.

In some embodiments, the pharmaceutical composition comprises a solvent. In some aspects, the solvent is saline solution, such as a sterile isotonic saline solution or dextrose solution. In some aspects, the solvent is water for injection.

In some embodiments, the pharmaceutical compositions are in a particulate form, such as a microparticle or a nanoparticle. Microparticles and nanoparticles may be formed from any suitable material, such as a polymer or a lipid. In some aspects, the microparticles or nanoparticles are micelles, liposomes, or polymersomes.

Further provided herein are anhydrous pharmaceutical compositions and dosage forms comprising an antibody, since water can facilitate the degradation of some antibodies.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

In certain embodiments, an antibody provided herein is formulated as parenteral dosage forms. Parenteral dosage forms can be administered to subjects by various routes including, but not limited to, subcutaneous, intravenous (including infusions and bolus injections), intramuscular, and intra-arterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry (e.g., lyophilized) products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Excipients that increase the solubility of one or more of the antibodies disclosed herein can also be incorporated into the parenteral dosage forms.

In some embodiments, the parenteral dosage form is lyophilized. Exemplary lyophilized formulations are described, for example, in U.S. Pat. Nos. 6,267,958 and 6,171,586; and WO 2006/044908; each of which is incorporated by reference in its entirety.

In human therapeutics, the doctor will determine the posology which he considers most appropriate according to a preventive or curative treatment and according to the age, weight, condition and other factors specific to the subject to be treated.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic antibody.

The amount of the antibody or composition which will be effective in the prevention or treatment of a disorder or one or more symptoms thereof will vary with the nature and severity of the disease or condition, and the route by which the antibody is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the antibodies provided herein are also encompassed by the dosage amounts and dose frequency schedules provided herein. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiments, treatment or prevention can be initiated with one or more loading doses of an antibody or composition provided herein followed by one or more maintenance doses.

In certain embodiments, a dose of an antibody or composition provided herein can be administered to achieve a steady-state concentration of the antibody in blood or serum of the subject. The steady-state concentration can be determined by measurement according to techniques available to those of skill or can be based on the physical characteristics of the subject such as height, weight and age.

As discussed in more detail elsewhere in this disclosure, an antibody provided herein may optionally be administered with one or more additional agents useful to prevent or treat a disease or disorder. The effective amount of such additional agents may depend on the amount of antibody present in the formulation, the type of disorder or treatment, and the other factors known in the art or described herein.

Therapeutic Applications

For therapeutic applications, antibodies are administered to a mammal, generally a human, in a pharmaceutically acceptable dosage form such as those known in the art and those discussed above. For example, antibodies may be administered to a human intravenously as a bolus or by continuous infusion over a period of time, by intramuscular, intraperitoneal, intra-cerebrospinal, subcutaneous, intra-articular, intrasynovial, intrathecal, or intratumoral routes. The antibodies also are suitably administered by peritumoral, intralesional, or perilesional routes, to exert local as well as systemic therapeutic effects. The intraperitoneal route may be particularly useful, for example, in the treatment of ovarian tumors.

The antibodies provided herein can be useful for the treatment of any disease or condition involving SIRP-ALPHA. In some embodiments, the disease or condition is a disease or condition that can benefit from treatment with an anti-SIRP-ALPHA antibody. In some embodiments, the disease or condition is a tumor. In some embodiments, the disease or condition is a cell proliferative disorder. In some embodiments, the disease or condition is a cancer. In some embodiments, the disease or condition is an infection.

Examples of symptoms, illnesses, and/or diseases that can be treated with a subject anti-SIRPα antibody include, but are not limited to cancer (any form of cancer, including but not limited to: carcinomas, soft tissue tumors, sarcomas, teratomas, melanomas, leukemias, lymphomas, brain cancers, solid tumors, mesothelioma (MSTO), etc.); infection (e.g., chronic infection); and an immunological disease or disorder (e.g., an inflammatory disease)(e.g., multiple sclerosis, arthritis, and the like, e.g., for immunosuppressive therapy). A subject anti-SIRPα antibody can also be used for transplant conditioning (e.g., stem cell transplant, bone marrow transplant, etc.) (e.g., to destroy malignant cells, to provide immunosuppression to prevent the patient's body from rejecting the donor's cells/stem cells, etc.). For example, in some cases, a subject antibody combination or bispecific antibody (e.g., anti-SIRPα in combination with anti-CD117) finds use for transplant conditioning. For example, a subject antibody combination or bispecific antibody (e.g., anti-SIRPα in combination with anti-CD117) can be used for bone marrow transplant conditioning. In some cases, a subject anti-SIRPα antibody (e.g., an antibody combination) can be used for immunosuppressive therapy.

In some embodiments, the antibodies provided herein are provided for use as a medicament. In some embodiments, the antibodies provided herein are provided for use in the manufacture or preparation of a medicament. In some embodiments, the medicament is for the treatment of a disease or condition that can benefit from an anti-SIRP-ALPHA antibody. In some embodiments, the disease or condition is a tumor. In some embodiments, the disease or condition is a cell proliferative disorder. In some embodiments, the disease or condition is a cancer. In some embodiments, the disease or condition is an infection. A disease or condition can be cancer; infection; a viral infection; a bacterial infection; a fungal infection; fibrosis; artherosclerosis; a parasitic infection, optionally malaria; and/or depletion or reduction of endogenous blood-forming stem cells from bone marrow to allow radiation and/or chemotherapy—free or—reduced conditioning for transplantation of blood-forming stem cells, optionally in combination with anti-CKIT (CD117) antibody.

In some embodiments, provided herein is a method of treating a disease or condition in a subject in need thereof by administering an effective amount of an antibody provided herein to the subject. In some aspects, the disease or condition is a cancer. In some aspects, the disease or condition is an infection.

In some embodiments, provided herein is a method of treating a disease or condition in a subject in need thereof by administering an effective amount of an antibody provided herein to the subject, wherein the disease or condition is a cancer, and the cancer is selected from a solid tumor and a hematological tumor.

In some embodiments, provided herein is a method of increasing phagocytosis in a subject in need thereof, comprising administering to the subject an effective amount of an antibody or a pharmaceutical composition disclosed herein.

In some embodiments, provided herein is a method of modulating an immune response in a subject in need thereof, comprising administering to the subject an effective amount of an antibody or a pharmaceutical composition disclosed herein.

Any suitable cancer may be treated with the antibodies provided herein.

For example, any cancer, where the cancer cells exhibit increased expression of CD47 compared to non-cancer cells, is a suitable cancer to be treated by the subject methods and compositions. As used herein "cancer" includes any form of cancer, including but not limited to solid tumor cancers (e.g., lung, prostate, breast, bladder, colon, ovarian, pancreas, kidney, liver, glioblastoma, medulloblastoma, leiomyosarcoma, head & neck squamous cell carcinomas, melanomas, neuroendocrine; etc.) and liquid cancers (e.g., hematological cancers); carcinomas; soft tissue tumors; sarcomas; teratomas; melanomas; leukemias; lymphomas; and brain cancers, including minimal residual disease, and including both primary and metastatic tumors. Any cancer, where the cancer cells express CD47 (e.g., in some cases, the cancer cells exhibit increased expression of CD47 compared to non-cancer cells), is a suitable cancer to be treated by the subject methods and compositions (e.g., a subject anti-SIRPα antibody).

Carcinomas are malignancies that originate in the epithelial tissues. Epithelial cells cover the external surface of the body, line the internal cavities, and form the lining of glandular tissues. Examples of carcinomas include, but are not limited to: adenocarcinoma (cancer that begins in glandular (secretory) cells), e.g., cancers of the breast, pancreas, lung, prostate, and colon can be adenocarcinomas; adrenocortical carcinoma; hepatocellular carcinoma; renal cell carcinoma; ovarian carcinoma; carcinoma in situ; ductal carcinoma; carcinoma of the breast; basal cell carcinoma; squamous cell carcinoma; transitional cell carcinoma; colon carcinoma; nasopharyngeal carcinoma; multilocular cystic renal cell carcinoma; oat cell carcinoma; large cell lung carcinoma; small cell lung carcinoma; non-small cell lung carcinoma; and the like. Carcinomas may be found in prostrate, pancreas, colon, brain (usually as secondary metastases), lung, breast, skin, etc.

Soft tissue tumors are a highly diverse group of rare tumors that are derived from connective tissue. Examples of soft tissue tumors include, but are not limited to: alveolar soft part sarcoma; angiomatoid fibrous histiocytoma; chondromyoxid fibroma; skeletal chondrosarcoma; extraskeletal myxoid chondrosarcoma; clear cell sarcoma; desmoplastic small round-cell tumor; dermatofibrosarcoma protuberans; endometrial stromal tumor; Ewing's sarcoma; fibromatosis (Desmoid); fibrosarcoma, infantile; gastrointestinal stromal tumor; bone giant cell tumor; tenosynovial giant cell tumor; inflammatory myofibroblastic tumor; uterine leiomyoma; leiomyosarcoma; lipoblastoma; typical lipoma; spindle cell or pleomorphic lipoma; atypical lipoma; chondroid lipoma; well-differentiated liposarcoma; myxoid/round cell liposarcoma; pleomorphic liposarcoma; myxoid malignant fibrous histiocytoma; high-grade malignant fibrous histiocytoma; myxofibrosarcoma; malignant peripheral nerve sheath tumor; mesothelioma; neuroblastoma; osteochondroma; osteosarcoma; primitive neuroectodermal tumor; alveolar rhabdomyosarcoma; embryonal rhabdomyosarcoma; benign or malignant schwannoma; synovial sarcoma; Evan's tumor; nodular fasciitis; desmoid-type fibromatosis; solitary fibrous tumor; dermatofibrosarcoma protuberans (DFSP); angiosarcoma; epithelioid hemangioendothelioma; tenosynovial giant cell tumor (TGCT); pigmented villonodular synovitis (PVNS); fibrous dysplasia; myxofibrosarcoma; fibrosarcoma; synovial sarcoma; malignant peripheral nerve sheath tumor; neurofibroma; and pleomorphic adenoma of soft tissue; and neoplasias derived from fibroblasts, myofibroblasts, histiocytes, vascular cells/endothelial cells and nerve sheath cells.

A sarcoma is a rare type of cancer that arises in cells of mesenchymal origin, e.g., in bone or in the soft tissues of the body, including cartilage, fat, muscle, blood vessels, fibrous tissue, or other connective or supportive tissue. Different types of sarcoma are based on where the cancer forms. For example, osteosarcoma forms in bone, liposarcoma forms in fat, and rhabdomyosarcoma forms in muscle. Examples of sarcomas include, but are not limited to: askin's tumor; sarcoma botryoides; chondrosarcoma; ewing's sarcoma; malignant hemangioendothelioma; malignant schwannoma; osteosarcoma; and soft tissue sarcomas (e.g., alveolar soft part sarcoma; angiosarcoma; cystosarcoma phyllodesdermatofibrosarcoma protuberans (DFSP); desmoid tumor; desmoplastic small round cell tumor; epithelioid sarcoma; extraskeletal chondrosarcoma; extraskeletal osteosarcoma; fibrosarcoma; gastrointestinal stromal tumor (GIST); hemangiopericytoma; hemangiosarcoma (more commonly referred to as "angiosarcoma"); kaposi's sarcoma; leiomyosarcoma; liposarcoma; lymphangiosarcoma; malignant peripheral nerve sheath tumor (MPNST); neurofibrosarcoma; synovial sarcoma; undifferentiated pleomorphic sarcoma, and the like).

A teratomas is a type of germ cell tumor that may contain several different types of tissue (e.g., can include tissues derived from any and/or all of the three germ layers: endoderm, mesoderm, and ectoderm), including for example, hair, muscle, and bone. Teratomas occur most often in the ovaries in women, the testicles in men, and the tailbone in children.

Melanoma is a form of cancer that begins in melanocytes (cells that make the pigment melanin). It may begin in a mole (skin melanoma), but can also begin in other pigmented tissues, such as in the eye or in the intestines.

Leukemias are cancers that start in blood-forming tissue, such as the bone marrow, and causes large numbers of abnormal blood cells to be produced and enter the bloodstream. For example, leukemias can originate in bone marrow-derived cells that normally mature in the bloodstream. Leukemias are named for how quickly the disease develops and progresses (e.g., acute versus chronic) and for the type of white blood cell that is effected (e.g., myeloid versus lymphoid). Myeloid leukemias are also called myelogenous or myeloblastic leukemias. Lymphoid leukemias are also called lymphoblastic or lymphocytic leukemia. Lymphoid leukemia cells may collect in the lymph nodes, which can become swollen. Examples of leukemias include, but are not limited to: Acute myeloid leukemia (AML), Acute lymphoblastic leukemia (ALL), Chronic myeloid leukemia (CML), and Chronic lymphocytic leukemia (CLL).

Lymphomas are cancers that begin in cells of the immune system. For example, lymphomas can originate in bone marrow-derived cells that normally mature in the lymphatic system. There are two basic categories of lymphomas. One kind is Hodgkin lymphoma (HL), which is marked by the presence of a type of cell called the Reed-Sternberg cell. There are currently 6 recognized types of HL. Examples of Hodgkin lymphomas include: nodular sclerosis classical Hodgkin lymphoma (CHL), mixed cellularity CHL, lymphocyte-depletion CHL, lymphocyte-rich CHL, and nodular lymphocyte predominant HL.

The other category of lymphoma is non-Hodgkin lymphomas (NHL), which includes a large, diverse group of cancers of immune system cells. Non-Hodgkin lymphomas can be further divided into cancers that have an indolent (slow-growing) course and those that have an aggressive (fast-growing) course. There are currently 61 recognized types of NHL. Examples of non-Hodgkin lymphomas include, but are not limited to: AIDS-related Lymphomas, anaplastic large-cell lymphoma, angioimmunoblastic lymphoma, blastic NK-cell lymphoma, Burkitt's lymphoma, Burkitt-like lymphoma (small non-cleaved cell lymphoma), chronic lymphocytic leukemia/small lymphocytic lymphoma, cutaneous T-Cell lymphoma, diffuse large B-Cell lymphoma, enteropathy-type T-Cell lymphoma, follicular lymphoma, hepatosplenic gamma-delta T-Cell lymphomas, T-Cell leukemias, lymphoblastic lymphoma, mantle cell lymphoma, marginal zone lymphoma, nasal T-Cell lymphoma, pediatric lymphoma, peripheral T-Cell lymphomas, primary central nervous system lymphoma, transformed lymphomas, treatment-related T-Cell lymphomas, and Waldenstrom's macroglobulinemia.

Brain cancers include any cancer of the brain tissues. Examples of brain cancers include, but are not limited to: gliomas (e.g., glioblastomas, astrocytomas, oligodendrogliomas, ependymomas, and the like), meningiomas, pituitary adenomas, vestibular schwannomas, primitive neuroectodermal tumors (medulloblastomas), etc.

As used herein, the term "infection" refers to any state in at least one cell of an organism (i.e., a subject) is infected by an infectious agent (e.g., a subject has an intracellular pathogen infection, e.g., a chronic intracellular pathogen infection). As used herein, the term "infectious agent" refers to a foreign biological entity (i.e. a pathogen) that induces CD47 expression (e.g., increased CD47 expression) in at least one cell of the infected organism. For example, infectious agents include, but are not limited to bacteria, viruses, protozoans, and fungi. Intracellular pathogens are of particular interest. Infectious diseases are disorders caused by infectious agents. Some infectious agents cause no recognizable symptoms or disease under certain conditions, but have the potential to cause symptoms or disease under changed conditions. The subject methods can be used in the treatment of chronic pathogen infections, for example including but not limited to viral infections, e.g. retrovirus, lentivirus, hepadna virus, herpes viruses, pox viruses, human papilloma viruses, etc.; intracellular bacterial infections, e.g. *Mycobacterium, Chlamydophila, Ehrlichia, Rickettsia, Brucella, Legionella, Francisella, Listeria, Coxiella, Neisseria, Salmonella, Yersinia* sp, *Helicobacter pylori* etc.; and intracellular protozoan pathogens, e.g. *Plasmodium* sp, *Trypanosoma* sp., *Giardia* sp., *Toxoplasma* sp., *Leishmania* sp., etc.

In some embodiments, provided herein is a method of antagonizing SIRP-ALPHA in a target cell of a subject in need thereof by administering an effective amount of an antibody provided herein to the subject.

In some embodiments, provided herein is a method of enhancing an immune response in a subject in need thereof by administering an effective amount of an antibody provided herein to the subject.

In some embodiments, provided herein is a method delaying the onset of a tumor in a subject in need thereof by administering an effective amount of an antibody provided herein to the subject.

In some embodiments, provided herein is a method preventing the recurrence or onset of a tumor in a subject in need thereof by administering an effective amount of an antibody provided herein to the subject.

In some embodiments, provided herein is a method of delaying the onset of a cancer in a subject in need thereof by administering an effective amount of an antibody provided herein to the subject.

In some embodiments, provided herein is a method of preventing the recurrence or onset of a cancer in a subject in need thereof by administering an effective amount of an antibody provided herein to the subject.

In some embodiments, provided herein is a method of reducing the size of a tumor in a subject in need thereof by administering an effective amount of an antibody provided herein to the subject.

In some embodiments, provided herein is a method of reducing the number of metastases in a subject in need thereof by administering an effective amount of an antibody provided herein to the subject.

In some embodiments, provided herein is a method of delaying the onset of an infection in a subject in need thereof by administering an effective amount of an antibody provided herein to the subject.

In some embodiments, provided herein is a method of preventing the recurrence or onset of an infection in a subject in need thereof by administering an effective amount of an antibody provided herein to the subject.

In some embodiments, provided herein is a method of reducing viral titer a subject in need thereof by administering an effective amount of an antibody provided herein to the subject.

In some embodiments, provided herein is a method of eliminating a virus from subject in need thereof by administering an effective amount of an antibody provided herein to the subject.

In some embodiments, provided herein is a method for extending the period of overall survival, median survival time, or progression-free survival in a subject in need thereof by administering an effective amount of an antibody provided herein to the subject.

Combination Therapies

In some embodiments, an antibody provided herein is administered with at least one additional therapeutic agent. Any suitable additional therapeutic agent may be administered with an antibody provided herein. In some aspects, the additional therapeutic agent is selected from radiation, a cytotoxic agent, a chemotherapeutic agent, a cytostatic agent, an anti-hormonal agent, an EGFR inhibitor, an immunostimulatory agent, an anti-angiogenic agent, and combinations thereof.

In some embodiments, the additional therapeutic agent comprises an immunostimulatory agent.

In some embodiments, the additional therapeutic agent is an antibody.

Anti-SIRPα antibodies may be used therapeutically in combination with a second antibody or agent that selectively binds to a target cell. The term "target cell" can be used in different ways depending on context. Typically a "target cell" is a cell that will be phagocytosed by a phagocytic cell (e.g., a phagocyte), where the phagocytosis is enhanced as a result of administering a subject anti-SIRPα antibody. Thus, the term "target cell" can refer to a CD47-expressing cell, because a subject anti-SIRPα antibody, by inhibiting the interaction between the CD47-expressing cell and the SIRPα expressing phagocytic cell, facilitates phagocytosis of the CD47-expressing cell.

However, in some cases, the target cell need not express high levels of CD47 (and in some cases need not express CD47 at all) in order for a subject multispecific antibody to induce phagocytosis of the target cell. For example, in the context of a multispecific (e.g., bispecific) antibody, the SIRPα binding region (the first binding region) of a subject multispecific (e.g., bispecific) antibody binds to SIRPα on a phagocytic cell (e.g., a macrophage), which allows the multispecific antibody to function as a tether to bring the phagocytic cell into the vicinity of a cell expressing an antigen (e.g., a marker of a cancer cell) that is recognized by (specifically bound by) a second binding region of the multispecific antibody (e.g., the second binding region of a bispecific antibody). Therefore, in the context of a multispecific antibody, a target cell can be a cell that does not express high levels of CD47 (and can also be a cell that does not express CD47). In some embodiments, a target cell is a mammalian cell, for example a human cell. A target cell can be from any individual (e.g., patient, subject, and the like) as described below.

In some cases, a target cell is an "inflicted" cell (e.g., a cell from an "inflicted" individual), where the term "inflicted" is used herein to refer to a subject with symptoms, an illness, or a disease that can be treated with a subject anti-SIRPα antibody. An "inflicted" subject can have cancer, can harbor an infection (e.g., a chronic infection), and/or can have other hyper-proliferative conditions, for example sclerosis, fibrosis, and the like, etc. "Inflicted cells" can be those cells that cause the symptoms, illness, or disease. As non-limiting examples, the inflicted cells of an inflicted patient can be CD47 expressing cancer cells, infected cells, inflammatory cells, immune cells, and the like. One indication that an illness or disease can be treated with a subject anti-SIRPα antibody is that the involved cells (i.e., the inflicted cells, e.g., the cancerous cells, the infected cells, the inflammatory cells, the immune cells, etc.) express CD47 (e.g., in some cases, an increased level of CD47 compared to normal cells of the same cell type).

In some embodiments, the additional therapeutic agent is an antibody that binds a protein or proteins on a tumor cell surface.

For the treatment of cancer, the anti-SIRPα antibody may be combined with one or more antibodies specific for a tumor antigen. Of these, tumor-associated antigens (TAAs) are relatively restricted to tumor cells, whereas tumor-specific antigens (TSAs) are unique to tumor cells. TSAs and TAAs typically are portions of intracellular molecules expressed on the cell surface as part of the major histocompatibility complex.

Tissue specific differentiation antigens are molecules present on tumor cells and their normal cell counterparts.

Tumor-associated antigens known to be recognized by therapeutic mAbs fall into several different categories. Hematopoietic differentiation antigens are glycoproteins that are usually associated with cluster of differentiation (CD) groupings and include CD20, CD30, CD33 and CD52. Cell surface differentiation antigens are a diverse group of glycoproteins and carbohydrates that are found on the surface of both normal and tumor cells. Antigens that are involved in growth and differentiation signaling are often growth factors and growth factor receptors. Growth factors that are targets for antibodies in cancer patients include CEA, epidermal growth factor receptor (EGFR; also known as ERBB1)' ERBB2 (also known as HER2), ERBB3, MET (also known as HGFR), insulin-like growth factor 1 receptor (IGF1R), ephrin receptor A3 (EPHA3), tumor necrosis factor (TNF)-related apoptosis-inducing ligand receptor 1 (TRAILR1; also known as TNFRSF10A), TRAILR2 (also known as TNFRSF10B) and receptor activator of nuclear factor-κB ligand (RANKL; also known as TNFSF11). Antigens involved in angiogenesis are usually proteins or growth factors that support the formation of new microvasculature, including vascular endothelial growth factor (VEGF), VEGF receptor (VEGFR), integrin αVβ3 and integrin α5β1. Tumor stroma and the extracellular matrix are indispensable support structures for a tumor. Stromal and extracellular matrix antigens that are therapeutic targets include fibroblast activation protein (FAP) and tenascin.

Examples of therapeutic antibodies useful in bispecific configurations or as combination therapy include, without limitation, rituximab; Ibritumomab; tiuxetan; tositumomab; Brentuximab; vedotin; Gemtuzumab; ozogamicin; Alemtuzumab; IGN101; adecatumumab; Labetuzumab; huA33; Pemtumomab; oregovomab; CC49 (minretumomab); cG250; J591; MOv18; MORAb-003 (farletuzumab); 3F8, ch 14.18; KW-2871; hu3S193; IgN311; Bevacizumab; IM-2C6; CDP791; Etaracizumab; Volociximab; Cetuximab, panitumumab, nimotuzumab; 806; Trastuzumab; pertuzumab; MM-121; AMG 102, METMAB; SCH 900105; AVE1642, IMC-A12, MK-0646, R1507; CP 751871; KB004; IIIA4; Mapatumumab (HGS-ETR1); HGS-ETR2; CS-1008; Denosumab; Sibrotuzumab; F19; and 81C6. A bispecific antibody may use the Fc region that activates an Fcγ receptor.

For the treatment of cancer, the anti-SIRPα antibody may be combined with one or more antibodies that inhibit immune checkpoint proteins. Of particular interest are immune checkpoint proteins displayed on the surface of a tumor cell. The immune-checkpoint receptors that have been most actively studied in the context of clinical cancer immunotherapy, cytotoxic T-lymphocyte-associated antigen 4 (CTLA4; also known as CD152) and programmed cell death protein 1 (PD1; also known as CD279)—are both inhibitory receptors. The clinical activity of antibodies that block either of these receptors implies that antitumor immunity can be enhanced at multiple levels and that combinatorial strategies can be intelligently designed, guided by mechanistic considerations and preclinical models.

The two ligands for PD1 are PD1 ligand 1 (PDL1; also known as B7-H1 and CD274) and PDL2 (also known as B7-DC and CD273). PDL1 is expressed on cancer cells and through binding to its receptor PD1 on T cells it inhibits T cell activation/function. See, for example, Avelumab as a therapeutic antibody.

Agents that agonize an immune costimulatory molecule are also useful in the methods disclosed herein. Such agents include agonists or CD40 and OX40. CD40 is a costimulatory protein found on antigen presenting cells (APCs) and is required for their activation. These APCs include phagocytes (macrophages and dendritic cells) and B cells. CD40 is part of the TNF receptor family. The primary activating signaling molecules for CD40 are IFNγ and CD40 ligand (CD40L). Stimulation through CD40 activates macrophages.

Anti CCR4 (CD194) antibodies of interest include humanized monoclonal antibodies directed against C—C chemokine receptor 4 (CCR4) with potential anti-inflammatory and antineoplastic activities.

In some embodiments, the additional therapeutic agent is an antibody that binds: HER2 (ERBB2/neu), CD52, PD-L1, VEGF, CD30, EGFR, CD38, RANKL (CD254), GD2 (ganglioside), SLAMF7 (CD319), CD20, EGFR, PDGFRa, VEGFR2, CD33, CD44, CD99, CD96, CD90, CD133, CKIT (CD117 for CKIT positive tumors); CTLA-4, PD-1, PD-L1, CD40 (agonistic), LAG3 (CD223), 41BB (CD137 agonistic), OX40 (CD134, agonistic); and/or CKIT (CD117) to deplete blood-forming stem cells for transplantation therapy.

In some embodiments, the additional therapeutic agent is at least one of: Rituximab, Cetuximab, Alemtuzumab (CD52), Atezolizumab (PD-L1), Avelumab (PD-L1), Bevacizumab (VEGF), Brentuximab (CD30), Daratumumab (CD38), Denosumab (RANKL), Dinutuximab (GD2), Elotuzumab (SLAMF7), Ibritumomab (CD20), Ipilimumab (CTLA-4), Necitumumab (EGFR), Nivolumab (PD-1), Obinutuzumab (CD20), Ofatumumab (CD20), Olaratumab (PDGFRa), Panitumumab (EGFR), Pembrolizumab (PD-1), Pertuzumab (HER2), Ramucirumab (VEGFR2), Tositumomab (CD20), and Gemtuzumab (CD33).

The additional therapeutic agent can be administered by any suitable means. In some embodiments, an antibody provided herein and the additional therapeutic agent are included in the same pharmaceutical composition. In some embodiments, an antibody provided herein and the additional therapeutic agent are included in different pharmaceutical compositions.

In embodiments where an antibody provided herein and the additional therapeutic agent are included in different pharmaceutical compositions, administration of the antibody can occur prior to, simultaneously, and/or following, administration of the additional therapeutic agent. In some aspects, administration of an antibody provided herein and the additional therapeutic agent occur within about one month of each other. In some aspects, administration of an antibody provided herein and the additional therapeutic agent occur within about one week of each other. In some aspects, administration of an antibody provided herein and the additional therapeutic agent occur within about one day of each other. In some aspects, administration of an antibody provided herein and the additional therapeutic agent occur within about twelve hours of each other. In some aspects, administration of an antibody provided herein and the additional therapeutic agent occur within about one hour of each other.

Diagnostic Methods

Also provided are methods for detecting the presence of SIRP-ALPHA on cells from a subject. Such methods may be used, for example, to predict and evaluate responsiveness to treatment with an antibody provided herein.

In some embodiments, a blood sample is obtained from a subject and the fraction of cells expressing SIRP-ALPHA is determined. In some aspects, the relative amount of SIRP-ALPHA expressed by such cells is determined. The fraction of cells expressing SIRP-ALPHA and the relative amount of SIRP-ALPHA expressed by such cells can be determined by any suitable method. In some embodiments, flow cytometry is used to make such measurements. In some embodiments, fluorescence assisted cell sorting (FACS) is used to make such measurement. See Li et al., *J. Autoimmunity*, 2003, 21:83-92 for methods of evaluating expression of SIRP-ALPHA in peripheral blood.

Kits

Also provided are kits comprising an antibody provided herein. The kits may be used for the treatment, prevention, and/or diagnosis of a disease or disorder, as described herein.

In some embodiments, the kit comprises a container and a label or package insert on or associated with the container. Suitable containers include, for example, bottles, vials, syringes, and IV solution bags. The containers may be formed from a variety of materials, such as glass or plastic. The container holds a composition that is by itself, or when combined with another composition, effective for treating, preventing and/or diagnosing a disease or disorder. The container may have a sterile access port. For example, if the container is an intravenous solution bag or a vial, it may have a port that can be pierced by a needle. At least one active agent in the composition is an antibody provided herein. The label or package insert indicates that the composition is used for treating the selected condition.

In some embodiments, the kit comprises (a) a first container with a first composition contained therein, wherein the first composition comprises an antibody provided herein; and (b) a second container with a second composition contained therein, wherein the second composition comprises a further therapeutic agent. The kit in this embodiment can further comprise a package insert indicating that the compositions can be used to treat a particular condition.

Alternatively, or additionally, the kit may further comprise a second (or third) container comprising a pharmaceutically-acceptable excipient. In some aspects, the excipient is a buffer. The kit may further include other materials desirable from a commercial and user standpoint, including filters, needles, and syringes.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ Ed. (Plenum Press) Vols A and B(1992).

Materials and Methods

Antibody Generation

A cDNA fragment of human SIRPa encoding the extracellular domain was synthesized and was fused to mouse Fc to generate a SIRPa-Fc fusion protein, which was used to immunize mice to produce monoclonal mouse anti-human CD47 antibodies. Hybridomas were generated using standard protocols. In brief, 4-6 week old Balb/c mice were immunized with purified recombinant a SIRPa-Fc fusion protein twice a week for a total of 4 weeks. Titers were assessed thereafter and the spleen cells were fused with SP2/0 cells. Hybridomas were selected and supernatants from the resulting clones were screened by enzyme linked immunosorbent assay (ELISA).

Antibody V Cloning and Sequencing.

The cloning strategy used here involved an initial RNA isolation from hybridoma cells (Qiagen). The cDNA sequences encoding the heavy and light chain variable regions of 1H9 and 3C2 monoclonal antibodies were obtained using 5' RACE-PCR techniques (Clontech) and were sequenced using standard DNA sequencing techniques.

Molecular Modeling and Antibody Humanization.

Humanization of 1H9 and 3C2 was performed by installing CDR residues from mouse antibodies onto human germline frameworks (FRs). Briefly, mouse 1H9 and 3C2 was humanized by judicious recruitment of corresponding CDR residues. Differences between mouse 1H9 and 3C2 and the human FR residues were individually modeled to investigate their possible influence on CDR conformation.

Cell Transfection.

293F cells were cultured under FreeStyle™ 293 Expression Medium (Invitrogen). Transient transfection was performed by co-transfection of expression vectors encoding antibody heavy chain and light chain using 293fectin transfection reagent (Invitrogen), according to the manufacturer's instructions. Four to five days later, supernatants from the transfected cells were harvested and tested for antibody secretion by ELISA. Briefly, 96-well plates (Nunc, Roskilde, Denmark) were coated with 1 µg/ml goat anti-human Fc gamma antibody in phosphate-buffered saline (PBS) for 16 hr at 4° C. After blocking for 1 hr with 0.4% BSA in PBS at room temperature, isolated supernatants were added in 1/3 sequential dilutions, and incubated for 1 hr at room temperature. Plates were subsequently washed three times and incubated with HRP-conjugated goat anti-human kappa-specific antibody for 1 hr at room temperature. After washing, plates were developed with TMB. The reaction was stopped with 2M $H_2SO_4$, and OD was measured at 450 nM.

Antibody Purification and Characterization.

The culture supernatant was applied to protein A Sepharose columns (GE Healthcare). The column was washed with PBS, and protein was then eluted with eluting buffer (0.1 M sodium citrate buffer, pH 3.0). Collected fractions were neutralized with 1 M Tris pH 9.0. Finally, purified samples were dialyzed against PBS. Purity of the eluted antibody fraction was analyzed by sodium dodecyl sulfate polyacrylamide gel electrophoresis (SDS-PAGE) on 10% gels under reducing or non-reducing conditions. Bands were visualized by Coomassie brilliant blue staining.

Antibody Affinity Measurement.

Human SIRPa-His fusion protein was made by fusing the extracellular domain of human SIRPa to His-tag and used for measuring monomeric binding affinity to 1H9 and 3C2. Binding experiments were performed on Biacore 3000 at 25° C. Goat anti-human capture antibody was immobilized (as indicated in the table) on the surface of the chip by direct immobilization using EDC/NHS coupling chemistry on flow cell2,3 and 4 of the CM5 chip. The unoccupied sites were blocked with 1M ethanolamine. Flow cell1 was untreated and used as reference for subtraction of any non-specific binding of the Ag to the chip surface. The test Abs were captured on flow cell 2, 3 and 4 at an RU as indicated. Antigen was flowed over the chip at single analyte concentration. Binding of antigen to the ligand was monitored in real time to obtain on (ka) and off (kd) rates. The equilibrium constant ($K_D$) was calculated from the observed ka and kd. For the fast off rate interactions, KD was determined by steady state kinetic analysis.

In Vitro Phagocytosis Assay.

Raji and HT29 cancer cells were washed and counted, then 25 µL containing $1 \times 10^5$ cells in serum-free IMDM were added to each well. Antibody treatment (in 25 µL) with a final concentration of 10 µg/mL of 1H9, 3C2 (otherwise indicated in the figures), rituximab or 0.1 µg/mL of cetuximab was added to the wells and incubated at 37° C. for 30 minutes. At 30 minutes, Macrophages that had previously been harvested with TrypLE were counted and plated with $5 \times 10^4$ cells in 50 µL of serum-free IMDM. Plates were incubated at 37° C. for 2 hours (Effector:Target=1:2). Phagocytosis percentage was calculated by Flow Cytometry analysis looking for GFP+ Macrophages.

Genotyping SIRPa Variants.

Genomic DNA was isolated from human donor blood samples using QIAamp DNA isolation kit (Qiagen). PCR was performed by using the isolated genomic DNA and primers of TAG AAT ACA GGC TCA TGT TGC AGG T (SEQ ID NO: 53) and GCC TTC AGC AAA TAG CAT GAC GT (SEQ ID NO: 54). PCR fragments were purified and sequenced. Different SIRPa variants were analyzed and identified according to SIRPa reference sequences (Polymorphism in Sirpa modulates engraftment of human hematopoietic stem cells. Nature Immunology, 8; 1313, 2007).

Blocking Human CD47 Binding on Monocytes Isolated from Human Donors.

Human peripheral blood mononuclear cells (PBMCs) were isolated from human blood using Ficoll. $5 \times 10^5$ cells were incubated with 1 ug/ml of AF488-conjugated human CD47-Fc fusion protein in the absence or presence of increasing concentrations of hHuIH9-G1. Binding of CD47 on the cells was measured and analyzed by flow cytometry.

Internalization of HuIH9-G1.

Internalization of humanized 1H9 was tested by incubating 10 ug/ml of the antibody with macrophage cells differentiated from normal human blood at 37° C. Cells were then fixed and permeabilized at each time point (0, 20 min, 1 h, 2 h, 4 h, 6 h, and 24 h). PE-labeled anti-human IgG1 antibody was used to detect 1H9. DAPI was used to stain nuclei. Incubation at 4° C. was used as a control for surface staining of 1H9.

Example 1: Anti-SIRPa Monoclonal Antibody Generation and Epitope Mapping

A cDNA fragment of human SIRPa encoding the extracellular domain was fused to mouse Fc to generate a SIRPa-Fc fusion protein (SEQ ID NO:45), which was used to immunize mice to produce monoclonal mouse anti-human SIRPa antibodies. The specificity of selected hybridoma clones was examined by ELISA binding to human SIRPa. Two of the positive clones were obtained and designated as 1H9 and 3C2. The variable regions of heavy and light chains were cloned and sequenced, and the sequences of VH and VL of 1H9 (FIG. 1) and 3C2 (FIG. 2) were determined.

To determine epitopes recognized by 1H9 and 3C2, human SIRPa-Fc fusion protein was coated in a 96-well plate. Binding of SIRPa with 1H9 and 3C2 was measured in the absence or presence of increasing concentrations of an anti-SIRPa antibody, KWar (disclosed in International Application WO 2015/138600, herein specifically incorporated by reference; Vh and Vl sequences shown in SEQ ID NOs 46-47). As shown in FIG. 3A, Kwar did not compete with 1H9 for SIRPa binding, indicating that 1H9 recognizes a distinct epitope than KWar. In contrast, Kwar competed 3C2 for SIRPa binding; however, the binding of 3C2 to SIRPa was only partially blocked even when 100-times excess amounts of KWar was used. This indicates that 3C2 likely recognizes an overlapping but not identical epitope as compared with KWar (FIG. 3A). Competitive binding was also performed between 1H9 and 3C2, and it was shown that binding of 1H9 with SIRPa was competed by 1H9 itself in a dose-dependent manner but not by 3C2 (FIG. 3B). Similarly, 3C2 competed itself in a dose-dependent manner but not by 1H9 (FIG. 3C). As such, 1H9 and 3C2 recognize distinct epitopes on SIRP-alpha.

Example 2: Antibody Isotype Selection for 1H9 and 3C2

Figure 4:
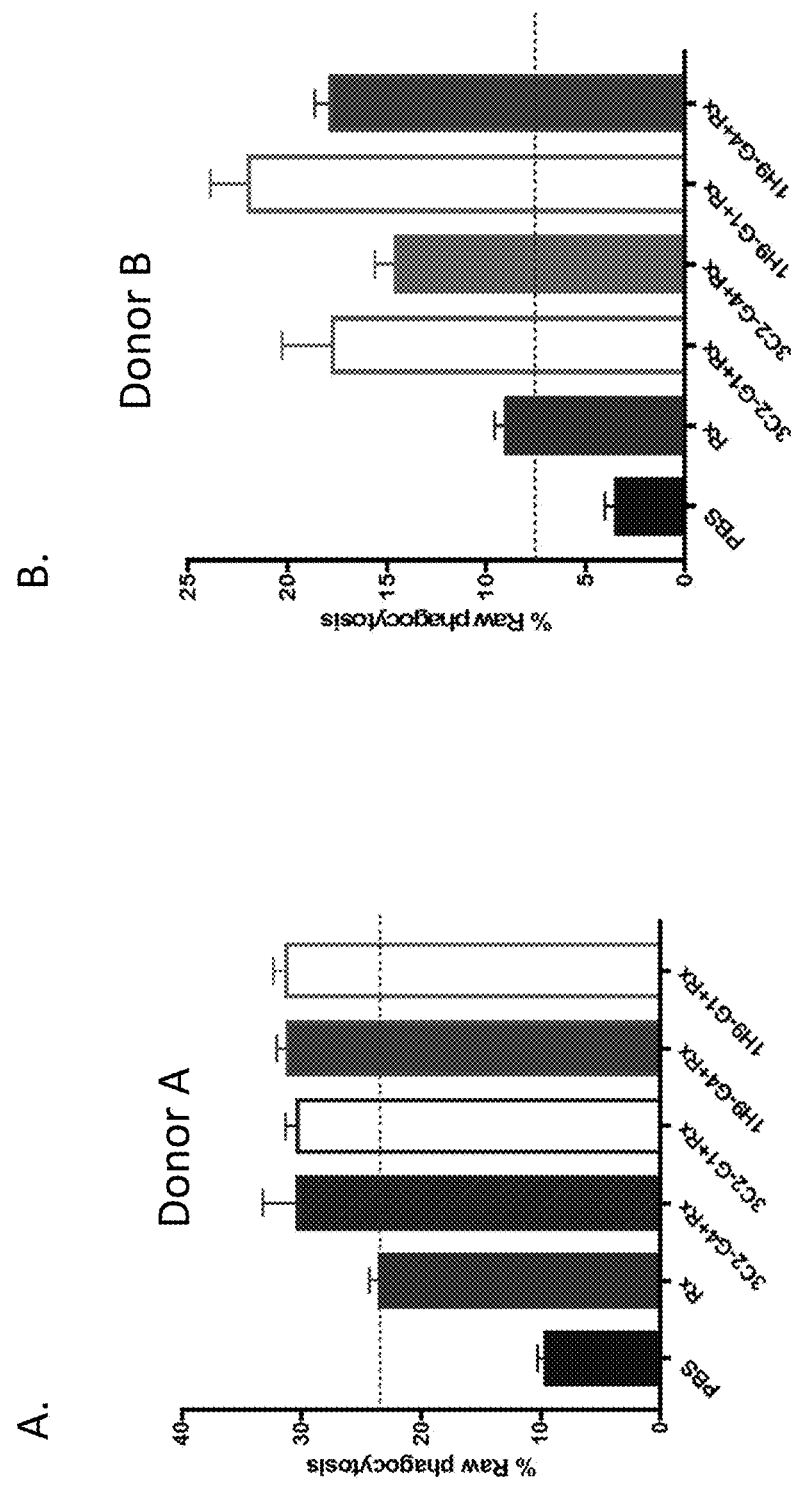
FIG. 4. 1H9 and 3C2 synergize with rituximab to promote macrophage-mediated phagocytosis of Raji cells. Macrophages were differentiated from monocytes of donor A (A) and donor B (B) in the presence of human serum for 7 days. Raji cells were labeled with CFSE and incubated with the macrophages in the presence of 10 ug/ml rituximab alone or in combination with 10 ug/ml of 1H9-G4, 1H9-G1, 3C2-G4, or 3C2-G1. Two hours later, Phagocytosis percentage was calculated by Flow Cytometry analysis looking for GFP+ Macrophages.

Chimeric 1H9 and 3C2 were constructed by fusing their light and heavy chain variable domains to the constant regions of human kappa, human IgG4, or human IgG1 which has a N297A mutation to abrogate interaction with FcgR. The resulting antibodies were then tested in an in vitro phagocytosis assay in combination with rituximab (Rx). The effects of donor variation were observed. 1H9 synergized with rituximab to promote phagocytosis equally well in human IgG4 (1H9-G4) and IgG1 N297A (1H9-G1) formats using macrophages differentiated from monocytes of some donors (FIG. 4A). While, using macrophages differentiated from monocytes of different donors, 1H9-G1 triggered better synergy with rituximab than that of 1H9-G4 (FIG. 4B). Similar results were also seen with 3C2 (FIG. 4A-B). It is possible that different allelic variations in FcgRs expressed on macrophages may cause the variations observed in the in vitro phagocytosis assay. These results demonstrate the general benefit of the dead-Fc construct for anti-SIRPα antibodies, in reducing variability of responsiveness, i.e., reducing the number of individuals that are non-responders in the enhancement of phagocytosis when combined with a cell-targeted antibody.

Example 3: 1H9 and 3C2 Humanization

Humanization of 1H9 and 3C2 was done by CDR-grafting, and the humanized sequences of VH and VL of 1H9 and 3C2 are shown in FIGS. 5 and 6, respectively. Full length sequences are shown in SEQ ID NOs 37-40.

Figure 7:
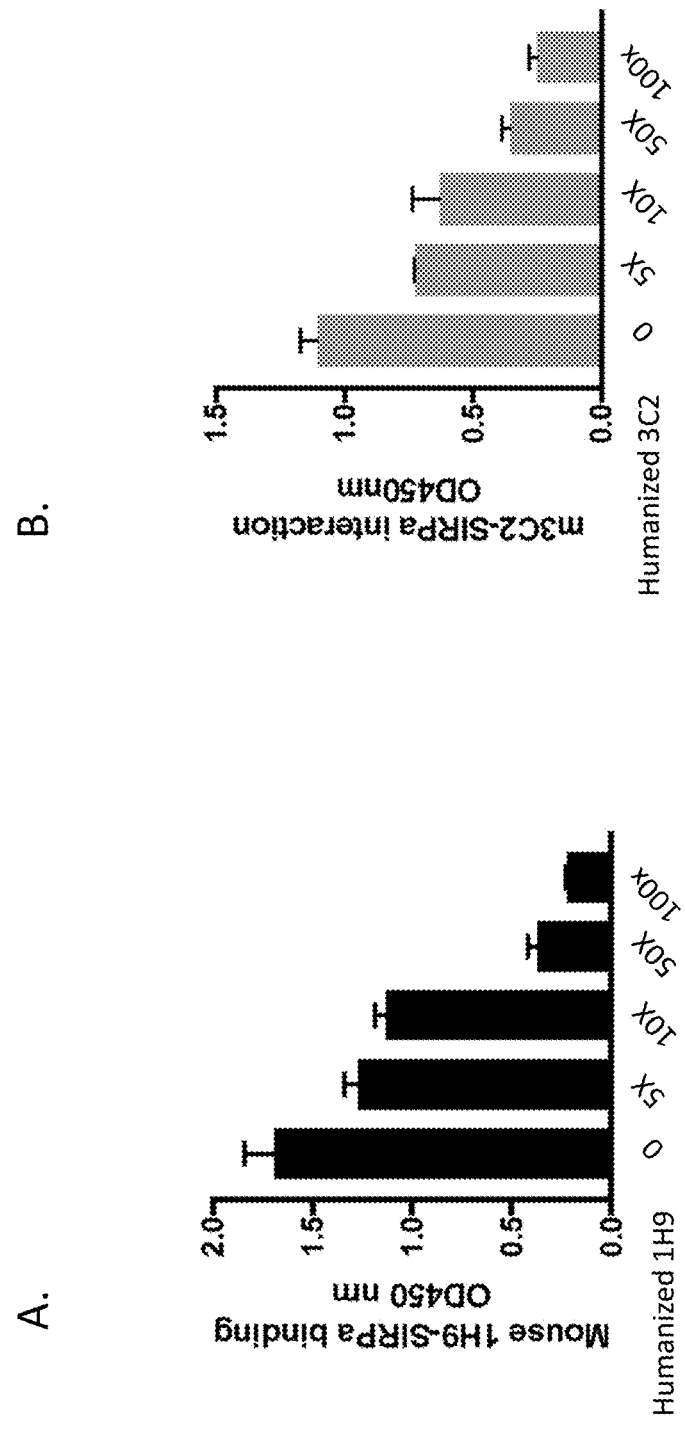
FIG. 7. Humanized 1H9 and 3C2 possesses the same antigen binding specificity as their parental antibodies. (A) SIRPa-Fc fusion protein was coated in a 96-wells plate and incubated with mouse 1H9 in the absence or presence of 5-, 10-, 50- and 100-times excess amounts of humanized 1H9. (B) SIRPa-Fc fusion protein was coated in a 96-wells plate and incubated with mouse 3C2 in the absence or presence of 5-, 10-, 50- and 100-times excess amounts of humanized 3C2.
Figure 8:
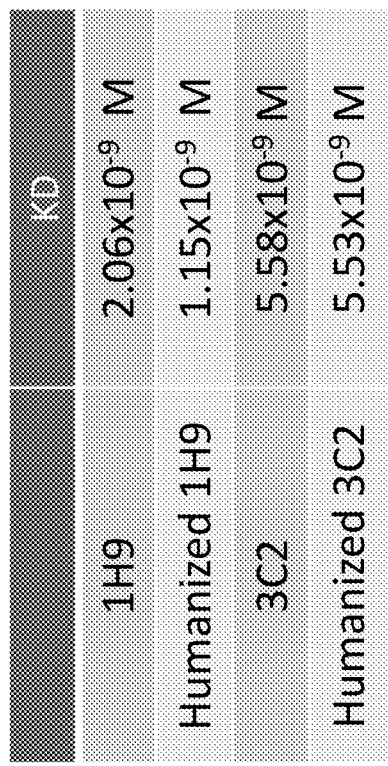
FIG. 8. Biacore affinity measurement of humanized 1H9 and 3C2.

To assess the antigen binding specificity of humanized 1H9 and 3C2, competition binding between humanized and parental mouse 1H9 or 3C2 was conducted by ELISA. It demonstrated that humanized 1H9 and 3C2 competed with mouse 1H9 and 3C2 for SIRPα binding in a dose-dependent manner, respectively (FIG. 7). Thus, humanized 1H9 and 3C2 possesses the same antigen binding specificity as their parental antibodies. The antigen binding affinities of humanized 1H9 and 3C2 were then measured using surface plasmon resonance. Humanized 1H9 bound to monomeric human SIRPα antigen with a $K_D$ of $1.15 \times 10^{-9}$ M, and humanized 3C2 bound to monomeric human SIRPα with a $K_D$ of $5.53 \times 10^{-9}$ M (FIG. 8).

Figure 9:
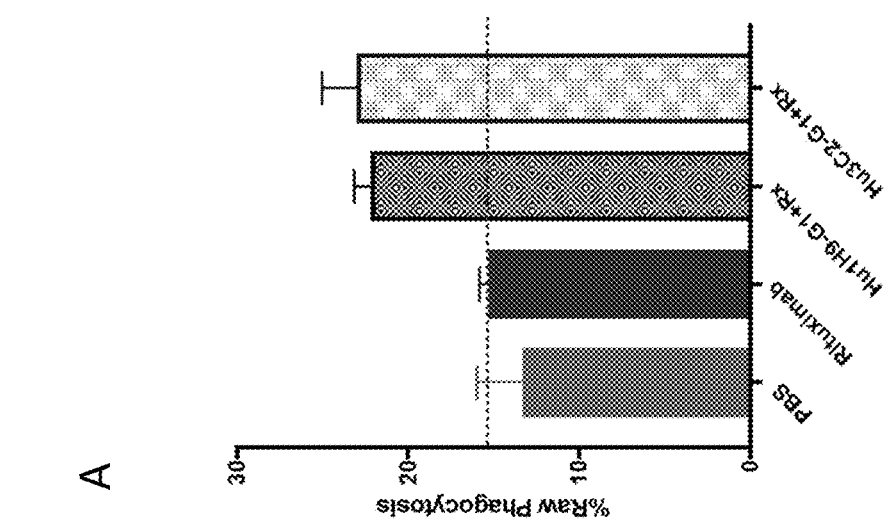
FIG. 9. Humanized 1H9 and 3C2 synergize with therapeutic antibodies to promote phagocytosis. (A) Raji cells were labeled with CFSE and incubated with human monocyte derived macrophages in the presence of 10 ug/ml rituximab alone or in combination with 10 ug/ml of HuIH9-G1 or Hu3C2-G1. (B) HT29 cells were labeled with CFSE and incubated with human monocyte derived macrophages in the presence of 0.1 ug/ml cetuximab alone or in combination with 0.5 ug/ml, 5 ug/ml and 10 ug/ml of HuIH9-G1 or Hu3C2-G1. Two hours later, Phagocytosis percentage was calculated by Flow Cytometry analysis looking for GFP+ Macrophages.

Example 4: Humanized 1H9 and 3C3 Synergize with Therapeutic Antibodies to Promote Macrophage-Mediated Phagocytosis We next investigated the ability of humanized 1H9 and 3C2 to enable the phagocytosis of human cancer cells by human peripheral blood-derived macrophages in combination of therapeutic antibodies. Humanized 1H9 or 3C2 alone did not substantially induce phagocytosis; however, when combined with rituximab (Rx) both antibodies induced higher phagocytic activity of Raji cells than that of rituximab alone (FIG. 9A). In addition, humanized 1H9 and 3C2 synergized with cetuximab (Cx) to induce phagocytosis of a human colorectal adenocarcinoma cell line HT-29, and the synergistic activity was observed across a range of concentrations of humanized 1H9 and 3C2 that were tested (FIG. 9B).

Example 5: Cross-Reactivity of 1H9 and 3C2 to SIRP Family Members

In addition to SIRP alpha there are two closely related proteins in the SIRP family namely (SIRPB, accession number NM_001083910.3) and SIRP gamma (SIRPG, accession number NM_001039508.1). SIRPB, although closely related to SIRPa, does not appear to bind CD47 and lacks cytoplasmic ITIMs or any other recognizable cytosolic motifs for signaling. Instead, SIRPB contains a trans-membrane region with a positively charged lysine residue that mediates association with DAP12, an adaptor protein that carries an ITAM. Phosphorylation of the DAP12 ITAM mediates recruitment of the protein tyrosine kinase Syk and consequent activation of the MAPK pathway that regulates various functions. Triggering of the murine SIRPB receptor, for instance, which also complexes with DAP12, promotes phagocytosis in macrophages. SIRPG, the third member of the human SIRP family, is expressed on T cells and activated NK cells. It can bind CD47, albeit with 10-fold lower affinity as compared with SIRPa. Moreover, SIRPg-CD47 interaction mediates cell-cell adhesion and supports APC-T cell contact, enhancing antigen presentation, the consequent T cell proliferation, and cytokine secretion. It is unlikely that SIRPG itself generates intracellular signals because it does not have any known signaling motifs. Instead, SIRPG may trigger signaling of CD47 in APCs.

Figure 10:
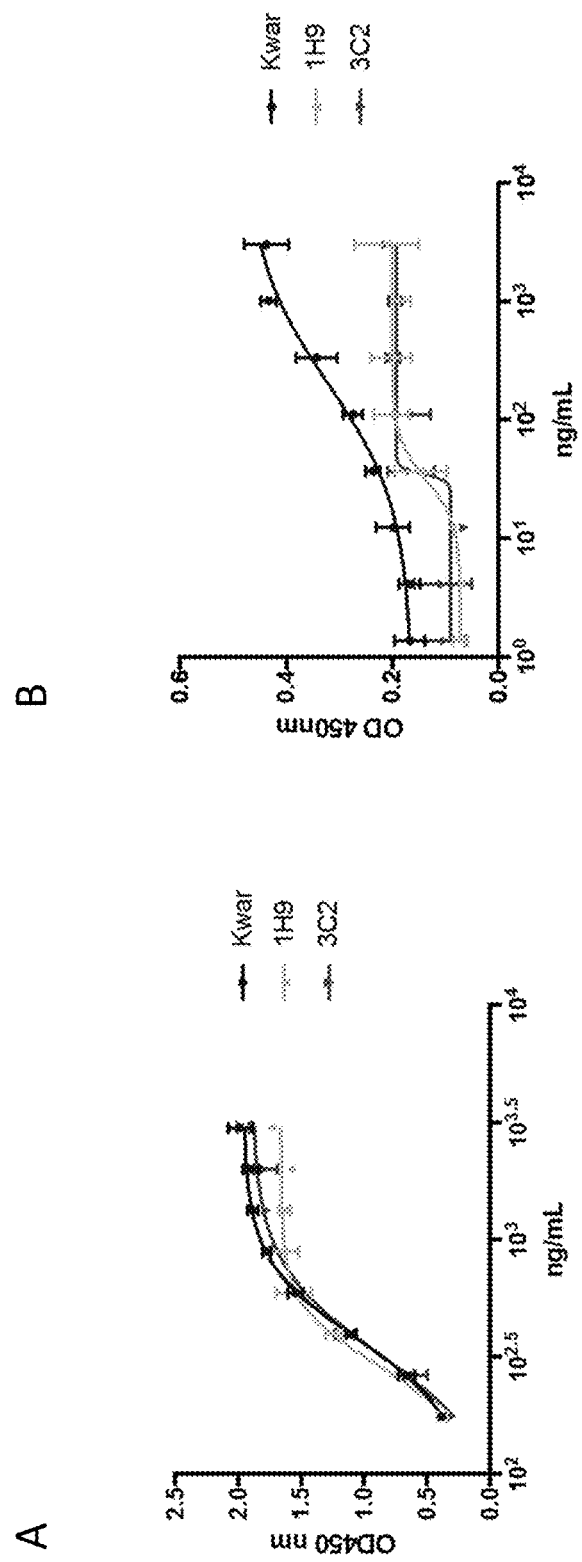
FIG. 10. Cross-reactivity to SIRPB and SIRPG. (A) Binding of Kwar, 1H9, and 3C2 to human SIRPB-His fusion protein was determined by ELISA. (B) Binding of Kwar, 1H9, and 3C2 to human SIRPG-His fusion protein was determined by ELISA.

SIRPB and SIRPG His-fusion protein were generated and binding of 1H9 and 3C2 to SIRPB and SIRPG was tested. As shown in FIG. 10, 1H9 and 3C2 bound to SIRPB as compared to that of Kwar (FIG. 10A). Unlike Kwar, no binding of 1H9 or 3C2 to SIRPG was detected (FIG. 10B). The lack of SIRPG binding by 1H9 and 3C2 confers the following potential advantages on these antibodies relative to state of the art anti-SIRPA antibodies: (1) SIRPA has more restricted expression relative to SIRPG which decreases risk of off-target effects, (2) there is a decreased risk of toxicity, e.g., given the increased specificity for SIRPA, (3) there is a decreased risk of developing an "antigen sink" phenomenon when the antibody is dosed in a subject, and (4) there is a decreased risk of interference with T cell and/or B cell function by the antibody.

Example 6: Generation and Testing of Additional Anti-SIRP-Alpha Antibodies

Additional antibodies were raised to human SIRPa by immunizing mice as outlined above. Two monoclonal antibody clones were designated—9B11 and 7E11, respectively. See SEQ ID NOs 21-36 and 41-44. The mouse variable regions were joined as a chimera to human IgG4 Fc region (designated as 7E11-G4 or 9B11-G4), or to a human IgG1 Fc region comprising N297A mutation to abrogate interaction with human FcγRs (designated as 7E11-G1 or 9B11-G1).

Figure 11:
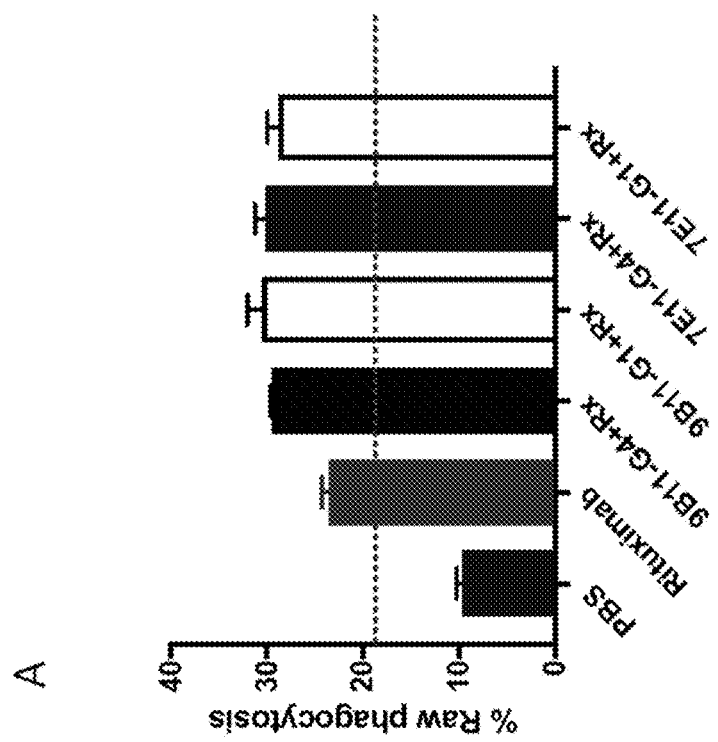
FIG. 11. 9B11 and 7E11 synergize with rituximab to promote macrophage-mediated phagocytosis of Raji cells.

As was found with 1H9 and 3C2, the 9B11 and 7E11 antibodies showed a synergistic response in enhancing phagocytosis of cancer cells when combined with Rituximab. Shown in FIG. 11, macrophages were differentiated from monocytes of donor A (A) and donor B (B) in the presence of human serum for 7 days. Raji cells were labeled with CFSE and incubated with the macrophages in the presence of 10 µg/ml rituximab (Rx) alone or in combination with 10 µg/ml of 9B11-G4, 9B11-G1, 7E11-G4, or 7E11-G1. Two hours later, Phagocytosis percentage was calculated by Flow Cytometry analysis looking for GFP+ Macrophages.

The data show that while both the IgG4 formatted antibodies and mutated IgG1 formatted antibodies could provide for a synergistic response, the mutated IgG1 format provided a more consistent response across donors.

Figure 12:
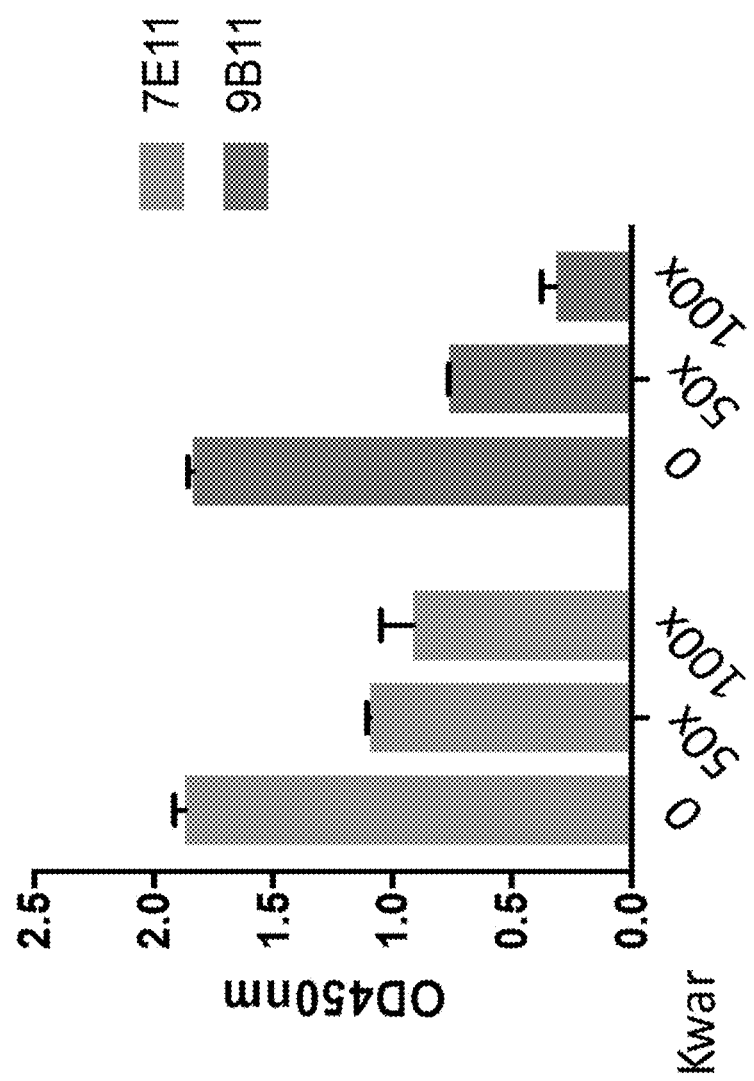
FIG. 12. 7E11 and 9B11 epitope binding. 7E11 recognizes an overlapping epitope as compared with Kwar (similar to 3C2) and 9B11 recognizes a very similar or identical epitope as compared with Kwar.

To determine epitopes recognized by 9B11 and 7E11, human SIRPa-Fc fusion protein was coated in a 96-well plate. Binding of SIRPa with 9B11 and 7E11 was measured in the absence or presence of increasing concentrations of an anti-SIRPa antibody, KWar (disclosed in International Application WO 2015/138600, herein specifically incorporated by reference). As shown in FIG. 12, 7E11 recognizes an overlapping epitope as compared with Kwar (similar to 3C2) and 9B11 recognizes a very similar or identical epitope as compared with Kwar.

Example 7: HuIH9-G1 Binding to Different SIRP-Alpha Variants on Primary Human Cells Human SIRP-α is highly polymorphic in the IgV domain, however, the majority of variants are variant 1 (V1) and variant 2 (V2).

Figure 13:
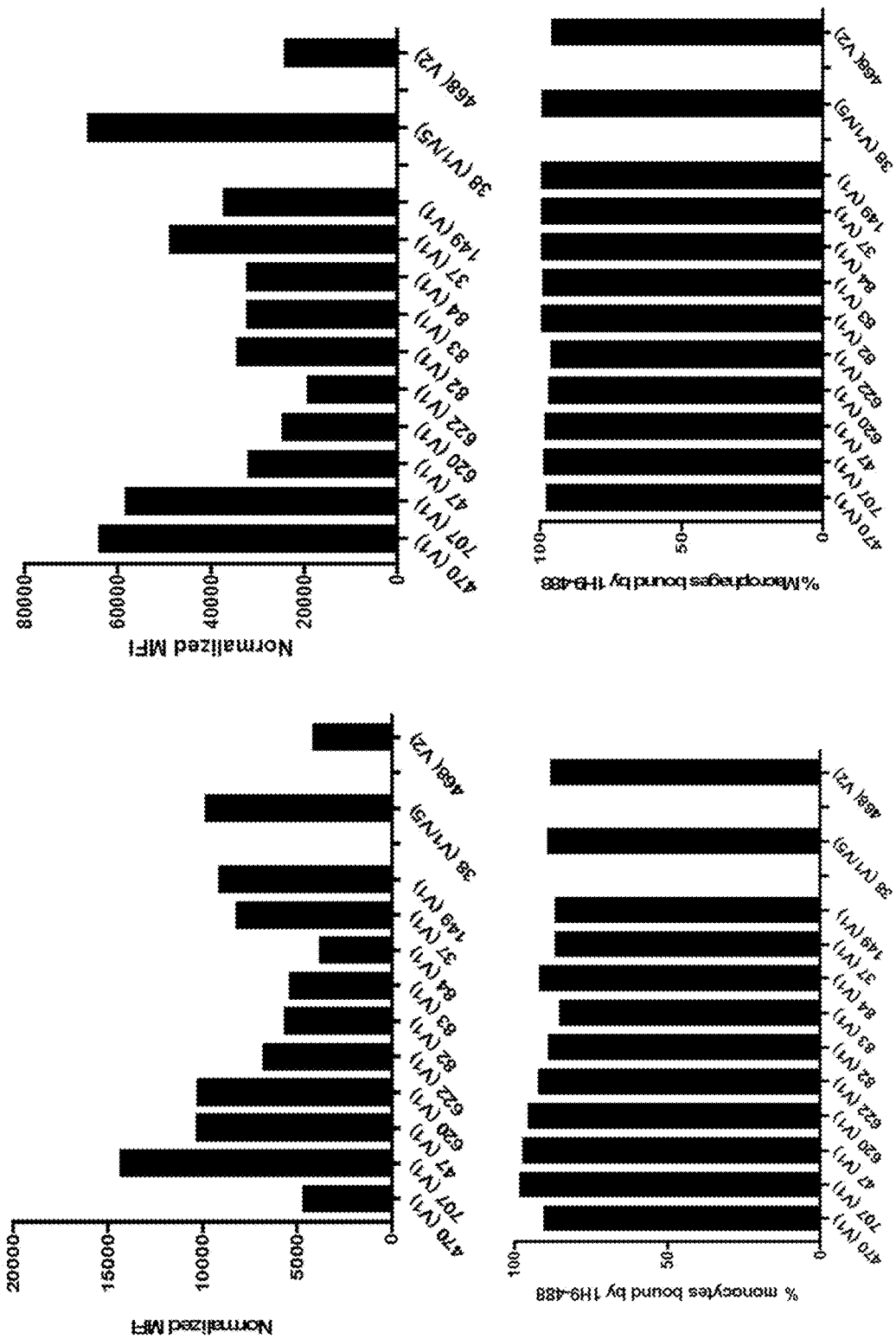
FIG. 13. HuIH9-G1 Binds to Both V1 and V2 Variants of SIRPα on Cells.

22 normal human donors were screened and genotyped and donors were identified with V1 homozygous, V2 homozygous, and V1/V5 heterozygous status for SIPR-alpha. (Polymorphism in Sirpa modulates engraftment of human hematopoietic stem cells. Nature Immunology, 8; 1313, 2007; For reference: V1 sequence shown in SEQ ID NO:48; V2 sequence shown in SEQ ID NO:49) Humanized 1H9 was tested and found to bind each of V1, V2, and V1/V5 alleles using the donors' monocytes and macrophages (FIG. 13). This data indicates that humanized 1H9 can be used in a wide range of humans given its ability to bind to multiple, distinct SIRP-alpha variants on primary human donor cells.

Figure 14:
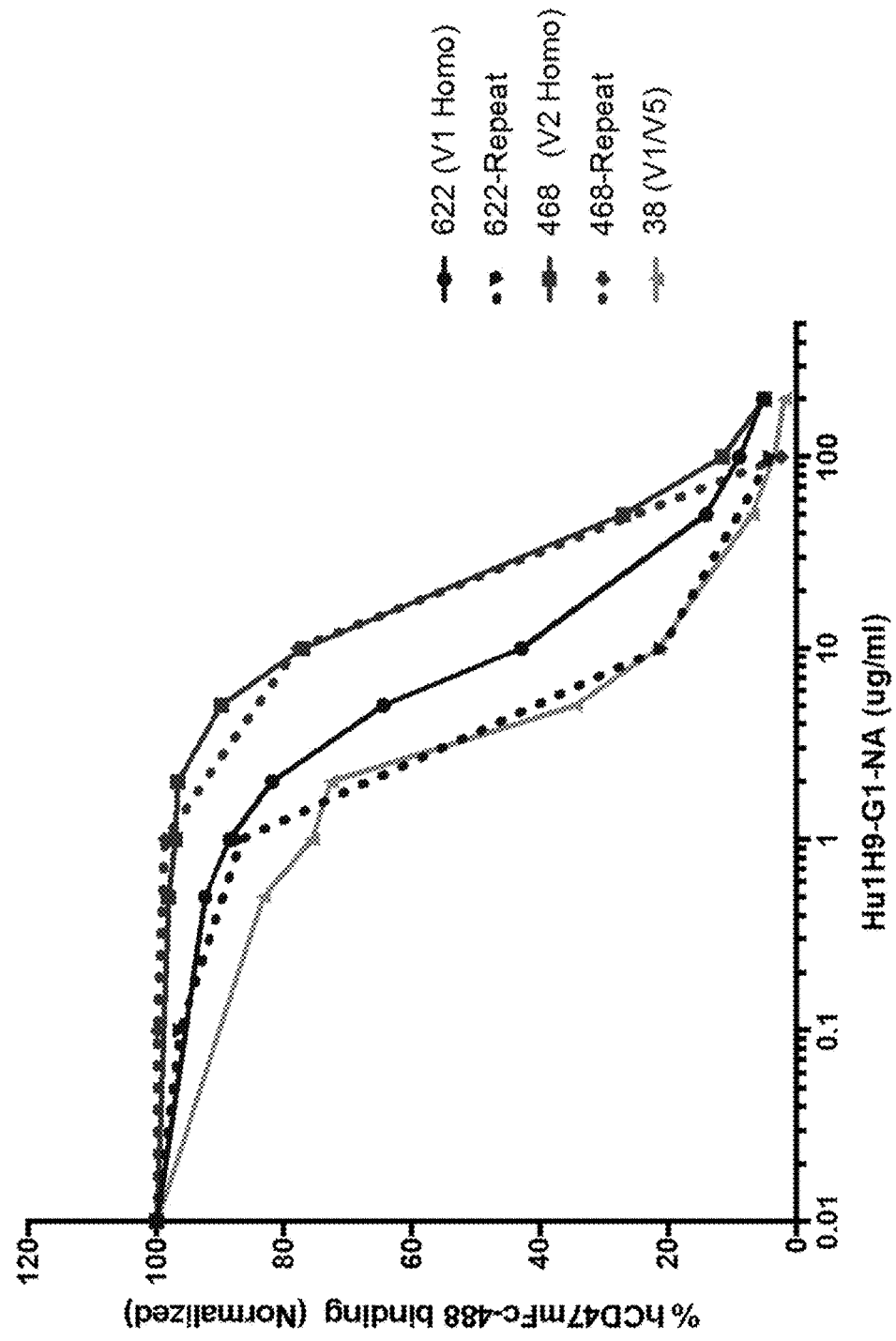
FIG. 14. HuIH9-G1 Blocks the Binding of CD47 to Monocytes from Different Donors.

Example 8: HuIH9-G1 Blocks the Binding of CD47 to Monocytes from Different Donors Humanized 1H9-G1 was next tested to determine if it can block interaction of CD47 and SIRP-alpha that is expressed as different variants. Monocytes were isolated from donors expressing V1, V2, and V1/V5 and incubated with CD47-Fc fusion protein either in the absence or presence of increasing concentrations of humanized 1H9 (FIG. 14). The data shows that humanized 1H9 blocked the interaction of CD47 and SIRP-alpha in a dose-dependent manner, and the blocking activities were comparable among different SIRP-alpha variants tested.

Figure 15:
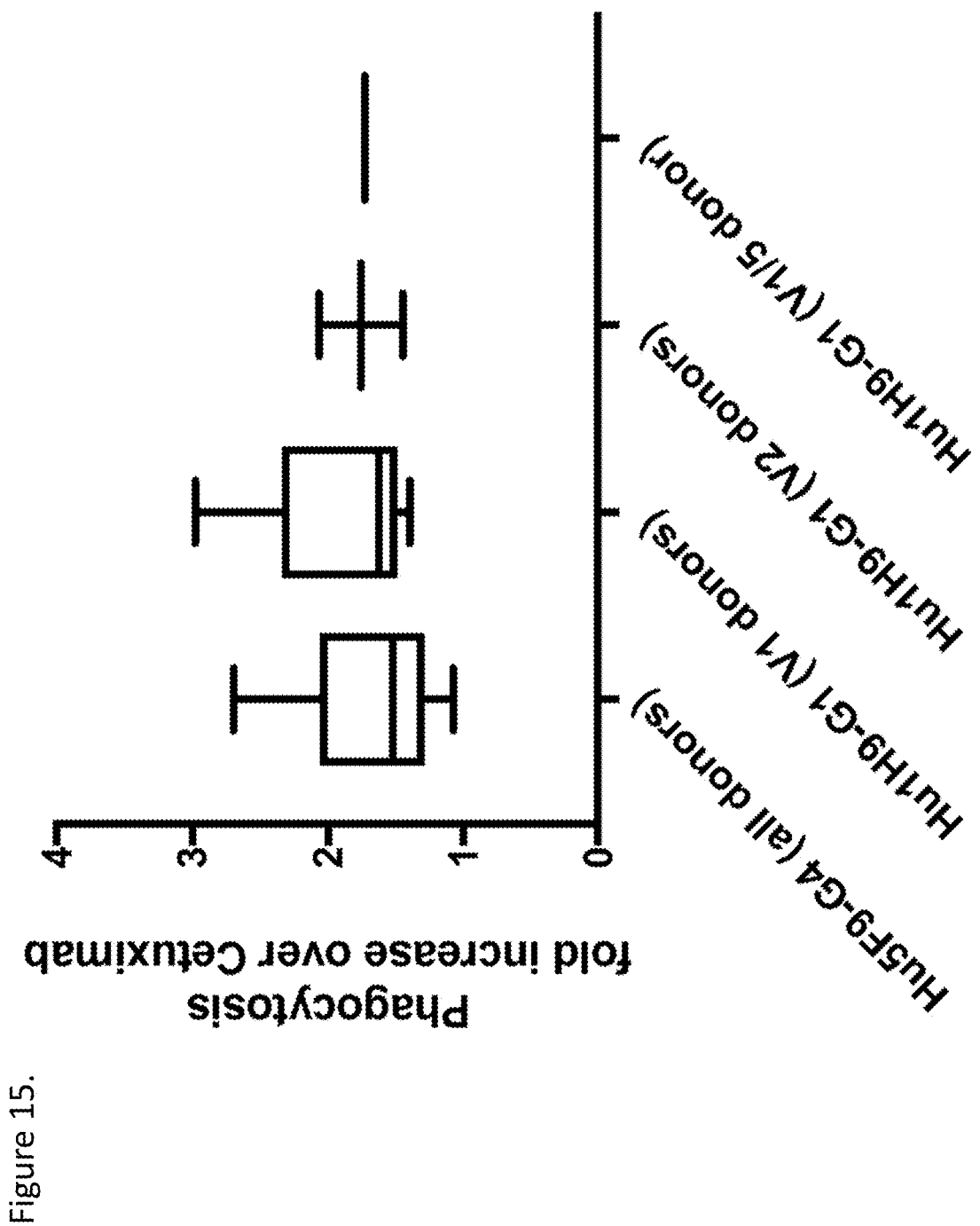
FIG. 15. HuIH9-G1 Synergizes with Cetuximab to Promote Phagocytosis across Different Donors.

Example 9: HuIH9-G1 Synergizes with Cetuximab to Promote Phagocytosis Across Different Donors In vitro phagocytosis using macrophages differentiated from different donors were performed. Humanized 1H9-G1 synergized with cetuximab to promote phagocytosis across donors having V1, V2, and V1/V5 variants (FIG. 15).

Example 10: Internalization of HuIH9-G1

Internalization of humanized 1H9 was tested by incubating 10 ug/ml of the antibody with macrophage cells differentiated from normal human blood at 37 C. Cells were then fixed and permeabilized at each time point (0, 20 min, 1 h, 2 h, 4 h, 6 h, and 24 h). PE-labeled anti-human IgG1 antibody was used to detect 1H9. DAPI was used to stain nuclei. Incubation at 4 C was used as a control for surface staining of 1H9.

The data shows that humanized 1H9 does not internalize into the cells and the surface staining of 1H9 was detectable at each time point including 24 hours (data not shown). This data indicates that humanized 1H9 is stable on the cell surface, which may be indicative of greater in vivo therapeutic efficacy.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

TABLE A

SEQUENCES

| SEQ ID NO | ID | Sequence |
|---|---|---|
| 1 | 1H9 CDR-H1 | SYWIT |
| 2 | 1H9 CDR-H2 | DIYPGSGSTNHIEKFKS |
| 3 | 1H9 CDR-H3 | GYGSSYGYFDY |
| 4 | 1H9 CDR-L1 | RASENIYSYLA |
| 5 | 1H9 CDR-L2 | TAKTLAE |

TABLE A -continued

SEQUENCES

| SEQ ID NO | ID | Sequence |
|---|---|---|
| 6 | 1H9 CDR-L3 | QHQYGPPFT |
| 7 | Humanized 1H9 VH | QVQLVQSGAE VKKPGASVKV SCKASGYTFT SYWITWVKQA PGQGLEWIGD IYPGSGSTNH IEKFKSKATL TVDTSISTAY MELSRLRSDD TAVYYCATGY GSSYGYFDYW GQGTLVTVSS |
| 8 | Humanized 1H9 VL | DIQMTQSPSS LSASVGDRVT ITCRASENIY SYLAWYQQKP GKAPKLLIYT AKTLAEGVPS RFSGSGSGTD FTLTISSLQP EDFATYYCQH QYGPPFTFGQ GTKLEIK |
| 9 | 3C2 CDR-H1 | SYWMH |
| 10 | 3C2 CDR-H2 | NIDPSDSDTHYNQKFKD |
| 11 | 3C2 CDR-H3 | GYSKYYAMDY |
| 12 | 3C2 CDR-L1 | RSSQSIVHSYGNTYLE |
| 13 | 3C2 CDR-L2 | KVSNRFS |
| 14 | 3C2 CDR-L3 | FQGSHVPYT |
| 15 | Humanized 3C2 $V_H$ | QVQLVQSGAE VKKPGASVKV SCKASGYTFT SYWMHWVRQA PGQGLEWMGN IDPSDSDTHY NQKFKDRVTM TRDTSTSTVY MELSSLRSED TAVYYCARGY SKYYAMDYWG QGTLVTVSS |
| 16 | Humanized 3C2 $V_L$ | DIVMTQTPLS LSVTPGQPAS ISCRSSQSIV HSYGNTYLEW YLQKPGQSPQ LLIYKVSNRF SGVPDRFSGS GSGTDFTLKI SRVEAEDVGV YYCFQGSHVP YTFGQGTKLE IK |
| 17 | Humanized 1H9 HC (full-length) | QVQLVQSGAEVKKPGASVKVSCKASGYTFTSYWITWVKQAPGQGLEW IGDIYPGSGSTNHIEKFKSKATLTVDTSISTAYMELSRLRSDDTAVY YCATGYGSSYGYFDYWGQGTLVTVSSASTKGPSVFPLAPSSKSTSGG TAALGCLVKDYFPEPVTVSWNSGALTSGVHTFPAVLQSSGLYSLSSV VTVPSSSLGTQTYICNVNHKPSNTKVDKKVEPKSCDKTHTCPPCPAP ELLGGPSVFLFPPKPKDTLMISRTPEVTCVVVDVSHEDPEVKFNWYV DGVEVHNAKTKPREEQYASTYRVVSVLTVLHQDWLNGKEYKCKVSNK ALPAPIEKTISKAKGQPREPQVYTLPPSREEMTKNQVSLTCLVKGFY PSDIAVEWESNGQPENNYKTTPPVLDSDGSFFLYSKLTVDKSRWQQG NVFSCSVMHEALHNHYTQKSLSLSPG |
| 18 | Humanized 1H9 LC (full-length) | DIQMTQSPSSLSASVGDRVTITCRASENIYSYLAWYQQKPGKAPKLL IYTAKTLAEGVPSRFSGSGSGTDFTLTISSLQPEDFATYYCQHQYGP PFTFGQGTKLEIKRTVAAPSVFIFPPSDEQLKSGTASVVCLLNNFYP REAKVQWKVDNALQSGNSQESVTEQDSKDSTYSLSSTLTLSKADYEK HKVYACEVTHQGLSSPVTKSFNRGEC |
| 19 | Humanized 3C2 HC (full-length) | QVQLVQSGAEVKKPGASVKVSCKASGYTFTSYWMHWVRQAPGQGLEW MGNIDPSDSDTHYNQKFKDRVTMTRDTSTSTVYMELSSLRSEDTAVY YCARGYSKYYAMDYWGQGTLVTVSSASTKGPSVFPLAPSSKSTSGGT AALGCLVKDYFPEPVTVSWNSGALTSGVHTFPAVLQSSGLYSLSSVV TVPSSSLGTQTYICNVNHKPSNTKVDKKVEPKSCDKTHTCPPCPAPE LLGGPSVFLFPPKPKDTLMISRTPEVTCVVVDVSHEDPEVKFNWYVD GVEVHNAKTKPREEQYASTYRVVSVLTVLHQDWLNGKEYKCKVSNKA LPAPIEKTISKAKGQPREPQVYTLPPSREEMTKNQVSLTCLVKGFYP SDIAVEWESNGQPENNYKTTPPVLDSDGSFFLYSKLTVDKSRWQQGN VFSCSVMHEALHNHYTQKSLSLSPG |
| 20 | Humanized 3C2 LC (full-length) | DIVMTQTPLSLSVTPGQPASISCRSSQSIVHSYGNTYLEWYLQKPGQ SPQLLIYKVSNRFSGVPDRFSGSGSGTDFTLKISRVEAEDVGVYYCF QGSHVPYTFGQGTKLEIKRTVAAPSVFIFPPSDEQLKSGTASVVCLL NNFYPREAKVQWKVDNALQSGNSQESVTEQDSKDSTYSLSSTLTLSK ADYEKHKVYACEVTHQGLSSPVTKSFNRGEC |
| 21 | 9B11 CDR-H1 | DYYIH |

TABLE A -continued

SEQUENCES

| SEQ ID NO | ID | Sequence |
|---|---|---|
| 22 | 9B11 CDR-H2 | RIDPEDGETKYAPKFQG |
| 23 | 9B11 CDR-H3 | GGFAY |
| 24 | 9B11 CDR-L1 | ASSSVSSSYLY |
| 25 | 9B11 CDR-L2 | STSNLAS |
| 26 | 9B11 CDR-L3 | HQWSSHPYT |
| 27 | 9B11 $V_H$ | EVQLQQSGAELVKPGASVKLSCTASGFNIKDYYIHWVKQRTEQGLEW IGRIDPEDGETKYAPKFQGKATITADTSSNTAYLQLNSLTSEDTAVY SCAKGGFAYWGQGTLVTVSA |
| 28 | 9B11 $V_L$ | QIVLTQSPAIMSASPGEKVTLTCSASSSVSSSYLYWYQQKPGSSPKL WIYSTSNLASGVPARFSGSGSGTSYSLTISSMEAEDAASYFCHQWSS HPYTFGGGTKLEIK |
| 29 | 7E11 CDR-H1 | SYWMH |
| 30 | 7E11 CDR-H2 | NIDPSDSDTHYNQKFKD |
| 31 | 7E11 CDR-H3 | SYGNYGENAMDY |
| 32 | 7E11 CDR-L1 | RSSQSIVHSYGNTYLE |
| 33 | 7E11 CDR-L2 | KVSNRFS |
| 34 | 7E11 CDR-L3 | FQGSHVPFT |
| 35 | 7E11 $V_H$ | QVKLQESGAELVRPGSSVKLSCKASGYTFTSYWMHWVKQRPIQGLEW IGNIDPSDSDTHYNQKFKDKATLTVDNSSSTAYMQLSSLTSEDSAVY YCASYGNYGENAMDYWGQGTSVTVSS |
| 36 | 7E11 $V_L$ | DILMTQTPLSLPVSLGDQASISCRSSQSIVHSYGNTYLEWYLQKPGQ SPKLLIYKVSNRFSGVPDRFSGSGSGTDFTLKISRVEAEDLGVYYCF QGSHVPFTFGSGTKLEIK |
| 37 | Humanized 1H9 heavy chain nucleic acid | CAGGTTCAGTTGGTTCAGTCTGGCGCCGAAGTGAAGAAACCTGGCGC CTCTGTGAAGGTGTCCTGCAAGGCTTCCGGCTACACCTTTACCAGCT ACTGGATCACCTGGGTCAAGCAGGCTCCTGGACAGGGACTCGAGTGG ATCGGCGATATCTATCCTGGCTCCGGCTCCACCAACCACATCGAGAA GTTCAAGTCCAAGGCTACCCTGACCGTGGACACCTCCATCTCCACCG CCTACATGGAACTGTCCCGGCTGAGATCTGACGACACCGCCGTGTAC TATTGCGCTACCGGCTACGGCTCCTCCTACGGCTACTTTGATTATTG GGGCCAGGGCACCCTGGTCACCGTGTCCTCTGCTTCTACCAAGGGAC CCAGCGTGTTCCCTCTGGCTCCTTCCAGCAAGTCTACCTCTGGCGGA ACAGCTGCTCTGGGCTGCCTGGTCAAGGACTACTTTCCTGAGCCTGT GACCGTGTCTTGGAACTCTGGCGCTCTGACATCTGGCGTGCACACAT TCCCTGCTGTGCTGCAGTCCTCCGGCCTGTACTCTCTGTCCTCTGTC GTGACCGTGCCTTCCAGCTCTCTGGGAACCCAGACCTACATCTGCAA TGTGAACCACAAGCCTTCCAACACCAAGGTGGACAAGAAGGTGGAAC CCAAGTCCTGCGACAAGACCCACACCTGTCCTCCATGTCCTGCTCCA GAACTGCTCGGCGGACCTTCCGTGTTTCTGTTCCCTCCAAAGCCTAA GGACACCCTGATGATCTCTCGGACCCCTGAAGTGACCTGCGTGGTGG TGGATGTGTCTCACGAGGACCCAGAAGTGAAGTTCAATTGGTACGTG GACGGCGTGGAAGTGCACAACGCCAAGACCAAGCCTAGAGAGGAACA GTACGCCTCCACCTACAGAGTGGTGTCCGTGCTGACAGTGCTGCACC AGGATTGGCTGAACGGCAAAGAGTACAAGTGCAAGGTGTCCAACAAG GCCCTGCCTGCTCCTATCGAAAAGACCATCTCCAAGGCCAAGGGCCA GCCTAGGGAACCCCAGGTTTACACCCTGCCACCTAGCCGGGAAGAGA TGACCAAGAACCAGGTGTCCCTGACCTGCCTCGTGAAGGGCTTCTAC CCTTCCGATATCGCTGTGGAATGGGAGAGCAACGGCCAGCCTGAGAA |

TABLE A -continued

SEQUENCES

| SEQ ID NO | ID | Sequence |
|---|---|---|
| | | CAACTACAAGACAACCCCTCCTGTGCTGGACTCCGACGGCTCATTCT<br>TTCTGTACTCCAAGCTGACTGTGGACAAGTCCAGATGGCAGCAGGGC<br>AACGTGTTCTCCTGCAGCGTGATGCACGAGGCCCTGCACAATCACTA<br>CACACAGAAGTCTCTGTCTCTGAGCCCCGGC |
| 38 | Humanized 1H9 light chain nucleic acid | GACATCCAGATGACCCAGTCTCCATCCTCTCTGTCCGCCTCTGTGGG<br>CGACAGAGTGACCATCACCTGTCGGGCCTCCGAGAACATCTACTCCT<br>ACCTGGCCTGGTATCAGCAGAAGCCTGGCAAGGCTCCCAAGCTGCTG<br>ATCTACACCGCTAAGACACTGGCCGAGGGCGTGCCCTCTAGATTTTC<br>TGGCTCTGGAAGCGGCACCGACTTTACCCTGACAATCTCCAGCCTGC<br>AGCCTGAGGACTTCGCCACCTACTACTGCCAGCACCAGTACGGCCCT<br>CCATTCACCTTTGGCCAGGGCACCAAGCTGGAAATCAAGCGGACAGT<br>GGCCGCTCCTTCCGTGTTCATCTTCCCACCTTCCGACGAGCAGCTGA<br>AGTCTGGCACAGCCTCTGTCGTGTGCCTGCTGAACAACTTCTACCCT<br>CGGGAAGCCAAGGTGCAGTGGAAGGTGGACAATGCCCTGCAGTCCGG<br>CAACTCCCAAGAGTCTGTGACCGAGCAGGACTCCAAGGACAGCACCT<br>ACAGCCTGTCCTCCACACTGACCCTGTCCAAGGCCGACTACGAGAAG<br>CACAAGGTGTACGCCTGCGAAGTGACCCATCAGGGCCTGTCTAGCCC<br>TGTGACCAAGTCTTTCAACCGGGGCGAGTGC |
| 39 | Humanized 3C2 heavy chain nucleic acid | CAGGTTCAGTTGGTTCAGTCTGGCGCCGAAGTGAAGAAACCTGGCGC<br>CTCTGTGAAGGTGTCCTGCAAGGCTTCCGGCTACACCTTTACCAGCT<br>ACTGGATGCACTGGGTCCGACAGGCTCCAGGACAAGGCTTGGAGTGG<br>ATGGGCAACATCGACCCCTCTGACAGCGACACCCACTACAACCAGAA<br>ATTCAAGGACCGCGTGACCATGACCAGAGACACCTCCACCAGCACCG<br>TGTACATGGAACTGTCCAGCCTGAGATCCGAGGACACCGCCGTGTAC<br>TACTGTGCCAGAGGCTACTCCAAGTACTACGCCATGGACTACTGGGG<br>CCAGGGCACACTGGTTACCGTGTCCTCTGCTTCCACCAAGGGACCCT<br>CTGTGTTCCCTCTGGCTCCTTCCAGCAAGTCTACCTCTGGCGGAACA<br>GCTGCTCTGGGCTGCCTGGTCAAGGACTACTTTCCTGAGCCTGTGAC<br>CGTGTCTTGGAACTCTGGCGCTCTGACATCTGGCGTGCACACATTCC<br>CTGCTGTGCTGCAGTCCTCCGGCCTGTACTCTCTGTCCTCTGTCGTG<br>ACCGTGCCTTCCAGCTCTCTGGGAACCCAGACCTACATCTGCAATGT<br>GAACCACAAGCCTTCCAACACCAAGGTGGACAAGAAGGTGGAACCCA<br>AGTCCTGCGACAAGACCCACACCTGTCCTCCATGTCCTGCTCCAGAA<br>CTGCTCGGCGGACCTTCCGTGTTTCTGTTCCCTCCAAAGCCTAAGGA<br>CACCCTGATGATCTCTCGGACCCCTGAAGTGACCTGCGTGGTGGTGG<br>ATGTGTCCCACGAAGATCCAGAAGTGAAGTTCAATTGGTACGTGGAC<br>GGCGTGGAAGTGCACAACGCCAAGACCAAGCCTAGAGAGGAACAGTA<br>CGCCTCCACCTACAGAGTGGTGTCCGTGCTGACAGTGCTGCACCAGG<br>ATTGGCTGAACGGCAAAGAGTACAAGTGCAAGGTGTCCAACAAGGCC<br>CTGCCTGCTCCTATCGAAAAGACCATCTCCAAGGCCAAGGGCCAGCC<br>TAGGGAACCCCAGGTTTACACCCTGCCTCCAAGCCGGGAAGAGATGA<br>CCAAGAACCAGGTGTCCCTGACCTGCCTCGTGAAGGGCTTCTACCCT<br>TCCGATATCGCCGTGGAATGGGAGAGCAATGGCCAGCCAGAGAACAA<br>CTACAAGACAACCCCTCCTGTGCTGGACTCCGACGGCTCATTCTTTC<br>TGTACTCCAAGCTGACCGTGGACAAGTCCAGATGGCAGCAGGGCAAC<br>GTGTTCTCCTGCAGCGTGATGCACGAGGCCCTGCACAATCACTATAC<br>CCAGAAGTCCCTGTCTCTGTCCCCTGGC |
| 40 | Humanized 3C2 light chain nucleic acid | GACATCGTGATGACCCAGACACCTCTGAGCCTGAGCGTGACACCTGG<br>ACAGCCTGCCTCCATCTCCTGCAGATCCTCTCAGTCCATCGTGCACT<br>CCTACGGCAACACCTACCTGGAATGGTATCTGCAGAAGCCCGGCCAG<br>TCTCCTCAGCTGCTGATCTACAAGGTGTCCAACCGGTTCTCTGGCGT<br>GCCCGACAGATTTTCCGGCTCTGGCTCTGGCACCGACTTCACCCTGA<br>AGATCTCCAGAGTGGAAGCCGAGGACGTGGGCGTGTACTACTGCTTC<br>CAAGGCTCTCACGTGCCCTACACCTTTGGCCAGGGCACCAAGCTGGA<br>AATCAAGCGGACAGTGGCCGCTCCTTCCGTGTTCATCTTCCCACCTT<br>CCGACGAGCAGCTGAAGTCCGGCACAGCTTCTGTCGTGTGCCTGCTG<br>AACAACTTCTACCCTCGGGAAGCCAAGGTGCAGTGGAAGGTGGACAA<br>TGCCCTGCAGTCCGGCAACTCCCAAGAGTCTGTGACCGAGCAGGACT<br>CCAAGGACAGCACCTACAGCCTGTCCAGCACACTGACCCTGTCCAAG<br>GCCGACTACGAGAAGCACAAGGTGTACGCCTGCGAAGTGACCCATCA<br>GGGCCTGTCTAGCCCTGTGACCAAGTCTTTCAACCGGGGCGAGTGC |
| 41 | 9B11 VH nucleic acid | GAGGTTCAGCTGCAGCAGTCTGGGGCAGAGCTTGTGAAGCCAGGGGC<br>CTCAGTCAAGTTGTCCTGCACAGCTTCTGGCTTCAACATTAAAGACT<br>ACTATATACACTGGGTGAAGCAGAGGACTGAACAGGGCCTGGAGTGG<br>ATTGGAAGGATTGATCCTGAGGATGGTGAAACTAAATATGCCCCGAA<br>ATTCCAGGGCAAGGCCACTATAACAGCAGACACATCCTCCAACACAG<br>CCTACCTGCAGCTCAACAGCCTGACATCTGAGGACACTGCCGTCTAT<br>TCCTGTGCTAAGGGGGGGTTTGCTTACTGGGGCCAAGGGACTCTGGT<br>CACTGTCTCTGCA |

TABLE A -continued

SEQUENCES

| SEQ ID NO | ID | Sequence |
|---|---|---|
| 42 | 9B11 VL nucleic acid | CAAATTGTTCTCACCCAGTCTCCAGCAATCATGTCTGCATCTCCTGG<br>GGAGAAGGTCACCTTGACCTGCAGTGCCAGTTCAAGTGTAAGTTCCA<br>GCTACTTGTACTGGTACCAGCAGAAGCCAGGATCCTCCCCCAAACTC<br>TGGATTTATAGCACATCCAACCTGGCTTCTGGAGTCCCTGCTCGCTT<br>CAGTGGCAGTGGGTCTGGGACCTCTTACTCTCTCACAATCAGCAGCA<br>TGGAGGCTGAAGATGCTGCCTCTTATTTCTGCCATCAGTGGAGTAGT<br>CACCCGTACACGTTCGGAGGGGGGACCAAGCTGGAAATAAAA |
| 43 | 7E11 VH nucleic acid | CAGGTCAAGCTGCAGGAGTCTGGGGCTGAGCTGGTGAGGCCTGGGTC<br>TTCAGTGAAGCTGTCCTGCAAGGCTTCTGGCTACACCTTCACCAGCT<br>ACTGGATGCATTGGGTGAAGCAGAGGCCTATACAAGGCCTTGAATGG<br>ATTGGTAACATTGACCCTTCTGATAGTGATACTCACTACAATCAAAA<br>GTTCAAGGACAAGGCCACATTGACTGTGGACAACTCCTCCAGCACAG<br>CCTACATGCAGCTCAGCAGCCTGACCTCTGAGGACTCTGCGGTCTAT<br>TACTGTGCAAGCTATGGTAACTACGGGGAGAATGCTATGGACTACTG<br>GGGTCAAGGAACCTCAGTCACCGTCTCCTCA |
| 44 | 7E11 VL nucleic acid | GATATTTTGATGACCCAAACTCCACTCTCCCTGCCTGTCAGTCTTGG<br>AGATCAAGCCTCCATCTCTTGCAGATCTAGTCAGAGCATTGTACATA<br>GTTATGGAAACACCTATTTAGAATGGTACCTGCAGAAACCAGGCCAG<br>TCTCCAAAACTCCTGATCTACAAAGTTTCCAACCGATTTTCTGGGGT<br>CCCAGACAGGTTCAGTGGCAGTGGATCAGGTACAGATTTCACACTCA<br>AGATCAGCAGAGTGGAGGCTGAGGATCTGGGAGTTTATTACTGCTTT<br>CAAGGTTCACATGTTCCATTCACGTTCGGCTCGGGGACAAAGTTGGA<br>AATAAAA |
| 45 | SIRPa | EEELQVIQPDKSVLVAAGETATLRCTATSLIPVGPIQWFRGAGPGRE<br>LIYNQKEGHFPRVTTVSDLTKRNNMDFSIRIGNITPADAGTYYCVKF<br>RKGSPDDVEFKSGAGTELSVRA |
| 46 | KWar VH | EVQLVQSGAEVKKPGATVKISCKVSGFNIKDYYIHWVQQAPGKGLEW<br>IGRIDPEDGETKYAPKFQDRATITADTSTDTAYMELSSLRSEDTAVY<br>YCARWGAYWGQGTLVTVSS |
| 47 | KWar VL | QIVLTQSPPTLSLSPGERVTLTCSASSSVSSSYLYWYQQKPGQAPKL<br>WIYSTSNLASGVPARFSGSGSGTSYTLTISSLQPEDFAVYFCHQWSS<br>YPRTFGAGTKLEIK |
| 48 | SIRPa V1 | EEELQVIQPDKSVLVAAGETATLRCTATSLIPVGPIQWFRGAGPGRE<br>LIYNQKEGHFPRVTTVSDLTKRNNMDFSIRIGNITPADAGTYYCVKF<br>RKGSPDDVEFKSGAGTELSVRA |
| 49 | SIRPa V2 | EEELQVIQPDKSVSVAAGESAILHCTVTSLIPVGPIQWFRGAGPARE<br>LIYNQKEGHFPRVTTVSESTKRENMDFSISISNITPADAGTYYCVKF<br>RKGSPDTEFKSGAGTELSVRA |

The invention claimed is:

1. An isolated humanized anti-SIRPα antibody of comprising a heavy chain comprising a variable heavy ($V_H$) chain sequence comprising three heavy chain CDR sequences, CDR-H1, CDR-H2, and CDR-H3, and a light chain comprising a variable light ($V_L$) chain sequence comprising three light chain CDR sequences, CDR-L1, CDR-L2, and CDR-L3, wherein:
CDR-H1 comprises the sequence set forth in SEQ ID NO:1; CDR-H2 comprises the sequence set forth in SEQ ID NO:2; CDR-H3 comprises the sequence set forth in SEQ ID NO:3; CDR-L1 comprises the sequence set forth in SEQ ID NO:4; CDR-L2 comprises the sequence set forth in SEQ ID NO:5; and CDR-L3 comprises the sequence set forth in SEQ ID NO:6.

2. The isolated antibody of claim 1, wherein:
the $V_H$ chain sequence comprises the $V_H$ sequence set forth in SEQ ID NO:7 and the $V_L$ chain sequence comprises the $V_L$ sequence set forth in SEQ ID NO:8.

3. The isolated antibody of claim 2, wherein:
the heavy chain comprises the heavy chain sequence set forth in SEQ ID NO:17 and the light chain comprises the light chain sequence set forth in SEQ ID NO:18.

4. The isolated antibody of claim 1, wherein the antibody comprises a human Fc region with reduced Fc-dependent function(s).

5. The isolated antibody of claim 4, wherein the human Fc region is IgG1 or IgG4.

6. The isolated antibody of claim 4, wherein the human Fc region with reduced Fc-dependent function(s) comprises at least one modification that reduces binding to a human Fc receptor.

7. The isolated antibody of claim 6, wherein the human Fc region is IgG1 and the Fc region modification comprises a modification at EU index position asparagine 297.

8. The isolated antibody of claim 7, wherein the human IgG1 Fc region modification comprises an N297A amino acid substitution, numbering according to EU index.

9. The isolated antibody of claim 1, wherein the antibody:
a. competes for binding to human SIRPα with a 1H9 antibody;
b. does not compete for binding to human SIRPα with KWar antibody;
c. partially competes for binding to human SIRPα with KWar antibody;
d. inhibits binding of human CD47 to human SIRPα;
e. inhibits binding of human SP-A to human SIRPα;
f. inhibits binding of human SP-D to human SIRPα;
g. binds to rhesus monkey SIRPα;
h. binds to cynomolgus SIRPα;
i. increases phagocytosis relative to control;
j. binds each of human SIRPα alleles V1 and V2;
k. binds each of human SIRPα alleles V1, V2, and V1/V5;
l. binds human SIRPα allele V1;
m. binds human SIRPα allele V2; or
n. is capable of any combination of (a)-(m).

10. The isolated antibody of claim 1, wherein the antibody is pan-specific for human SIRPa isotypes.

11. The isolated antibody of claim 1, wherein the antibody binds greater than one antigen or greater than one epitope on a single antigen.

12. The isolated antibody of claim 1, wherein the $V_H$ chain sequence consists of the $V_H$ sequence set forth in SEQ ID NO:7 and the $V_L$ chain sequence consists of the $V_L$ sequence set forth in SEQ ID NO:8.

13. The isolated antibody of claim 2, wherein the heavy chain consists of the sequence set forth in of SEQ ID NO:17 and the light chain consists of the sequence set forth in SEQ ID NO:18.

14. The isolated antibody of claim 1, wherein the $V_H$ sequence comprises the sequence set forth in SEQ ID NO:7 and the $V_L$ sequence comprises the sequence set forth in SEQ ID NO:8; and wherein the antibody comprises a human Fc region with reduced Fc-dependent function(s).

15. The isolated antibody of claim 1, wherein the $V_H$ chain sequence comprises the $V_H$ sequence set forth in SEQ ID NO:7 and the $V_L$ chain sequence comprises the $V_L$ sequence set forth in SEQ ID NO:8; and wherein the antibody comprises a human IgG1 Fc region with a modification at EU index position asparagine 297.

16. The isolated antibody of claim 1, wherein the $V_H$ chain sequence comprises the $V_H$ sequence set forth in SEQ ID NO:7 and the $V_L$ chain sequence comprises the $V_L$ sequence set forth in SEQ ID NO:8; and wherein the antibody comprises a human IgG1 Fc region with an N297A amino acid substitution, numbering according to EU index.

17. The isolated antibody of claim 2, wherein the heavy chain comprises the sequence set forth in of SEQ ID NO:17 and the light chain comprises the sequence set forth in SEQ ID NO:18; and wherein the antibody comprises a human Fc region with reduced Fc-dependent function(s).

18. The isolated antibody of claim 2, wherein the heavy chain comprises the sequence set forth in of SEQ ID NO:17 and the light chain comprises the sequence set forth in SEQ ID NO:18; and wherein the antibody comprises a human IgG1 Fc region with a modification at EU index position asparagine 297.

19. The isolated antibody of claim 2, wherein the heavy chain comprises the sequence set forth in of SEQ ID NO:17 and the light chain comprises the sequence set forth in SEQ ID NO:18; and wherein the antibody comprises a human IgG1 Fc region with an N297A amino acid substitution, numbering according to EU index.

20. A pharmaceutical composition comprising the antibody of claim 2 and a pharmaceutically acceptable excipient.

21. A pharmaceutical composition comprising the antibody of claim 3 and a pharmaceutically acceptable excipient.

22. A pharmaceutical composition comprising the antibody of claim 12 and a pharmaceutically acceptable excipient.

23. A pharmaceutical composition comprising the antibody of claim 15 and a pharmaceutically acceptable excipient.

24. An isolated polynucleotide or set of polynucleotides encoding the isolated antibody of claim 1, a $V_H$ thereof, a $V_L$ thereof, a light chain thereof, a heavy chain thereof, or an antigen-binding portion thereof.

25. A vector or set of vectors comprising the polynucleotide or set of polynucleotides of claim 24.

26. An isolated host cell comprising the polynucleotide or set of polynucleotides of claim 24.

27. A method of producing an antibody comprising expressing the antibody with the host cell of claim 26 and isolating the expressed antibody.

28. A pharmaceutical composition comprising the antibody of claim 1 and a pharmaceutically acceptable excipient.

29. A method of treating a CD47 positive disease or condition in a subject in need thereof, comprising administering to the subject an effective amount of the antibody of claim 1.

30. The method of claim 29, wherein the disease or condition is a cancer, and the cancer is selected from a solid tumor and a hematological tumor.

31. A method of increasing phagocytosis mediated by CD47 expression in a subject in need thereof, comprising administering to the subject an effective amount of the antibody of claim 1.

32. A method of modulating an immune response mediated by CD47 expression in a subject in need thereof, comprising administering to the subject an effective amount of the antibody of claim 1.

33. The method of claim 32, further comprising administering one or more additional therapeutic agents to the subject.

* * * * *

SEQUENCE LISTING

<160> NUMBER OF SEQ ID NOS: 58

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Tyr Trp Ile Thr
1               5

<210> SEQ ID NO 2
<211> LENGTH: 17
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 2

Asp Ile Tyr Pro Gly Ser Gly Ser Thr Asn His Ile Glu Lys Phe Lys
1               5                   10                  15

Ser

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Tyr Gly Ser Ser Tyr Gly Tyr Phe Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Ser Glu Asn Ile Tyr Ser Tyr Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Ala Lys Thr Leu Ala Glu
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln His Gln Tyr Gly Pro Pro Phe Thr
1               5

<210> SEQ ID NO 7
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Val Gln Ser Gly Ala Glu Val Lys Lys Pro Gly Ala
1               5                   10                  15
```

-continued

```
Ser Val Lys Val Ser Cys Lys Ala Ser Gly Tyr Thr Phe Thr Ser Tyr
            20                  25                  30

Trp Ile Thr Trp Val Lys Gln Ala Pro Gly Gln Gly Leu Glu Trp Ile
        35                  40                  45

Gly Asp Ile Tyr Pro Gly Ser Gly Ser Thr Asn His Ile Glu Lys Phe
    50                  55                  60

Lys Ser Lys Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Thr Gly Tyr Gly Ser Ser Tyr Gly Tyr Phe Asp Tyr Trp Gly Gln
            100                 105                 110

Gly Thr Leu Val Thr Val Ser Ser
        115                 120

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Ile
        35                  40                  45

Tyr Thr Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Gln Tyr Gly Pro Pro Phe
                85                  90                  95

Thr Phe Gly Gln Gly Thr Lys Leu Glu Ile Lys
            100                 105

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Tyr Trp Met His
1               5

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10
```

```
Asn Ile Asp Pro Ser Asp Ser Asp Thr His Tyr Asn Gln Lys Phe Lys
1               5                   10                  15

Asp
```

```
<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Tyr Ser Lys Tyr Tyr Ala Met Asp Tyr
1               5                   10
```

```
<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Ser Ser Gln Ser Ile Val His Ser Tyr Gly Asn Thr Tyr Leu Glu
1               5                   10                  15
```

```
<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Val Ser Asn Arg Phe Ser
1               5
```

```
<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Phe Gln Gly Ser His Val Pro Tyr Thr
1               5
```

```
<210> SEQ ID NO 15
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
```

```
                35                  40                  45
Gly Asn Ile Asp Pro Ser Asp Ser Asp Thr His Tyr Asn Gln Lys Phe
        50                  55                  60
Lys Asp Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Gly Tyr Ser Lys Tyr Tyr Ala Met Asp Tyr Trp Gly Gln Gly
            100                 105                 110
Thr Leu Val Thr Val Ser Ser
            115

<210> SEQ ID NO 16
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Val Met Thr Gln Thr Pro Leu Ser Leu Ser Val Thr Pro Gly
1               5                   10                  15
Gln Pro Ala Ser Ile Ser Cys Arg Ser Ser Gln Ser Ile Val His Ser
            20                  25                  30
Tyr Gly Asn Thr Tyr Leu Glu Trp Tyr Leu Gln Lys Pro Gly Gln Ser
        35                  40                  45
Pro Gln Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Phe Gln Gly
                85                  90                  95
Ser His Val Pro Tyr Thr Phe Gly Gln Gly Thr Lys Leu Glu Ile Lys
            100                 105                 110

<210> SEQ ID NO 17
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Trp Ile Thr Trp Val Lys Gln Ala Pro Gly Gln Gly Leu Glu Trp Ile
        35                  40                  45
Gly Asp Ile Tyr Pro Gly Ser Gly Ser Thr Asn His Ile Glu Lys Phe
    50                  55                  60
Lys Ser Lys Ala Thr Leu Thr Val Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Thr Gly Tyr Gly Ser Ser Tyr Gly Tyr Phe Asp Tyr Trp Gly Gln
```

```
            100                 105                 110
Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Ala Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 18
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ile Gln Met Thr Gln Ser Pro Ser Ser Leu Ser Ala Ser Val Gly
```

```
                1               5                   10                  15
            Asp Arg Val Thr Ile Thr Cys Arg Ala Ser Glu Asn Ile Tyr Ser Tyr
                            20                  25                  30

Leu Ala Trp Tyr Gln Gln Lys Pro Gly Lys Ala Pro Lys Leu Leu Ile
                            35                  40                  45

Tyr Thr Ala Lys Thr Leu Ala Glu Gly Val Pro Ser Arg Phe Ser Gly
                            50                  55                  60

Ser Gly Ser Gly Thr Asp Phe Thr Leu Thr Ile Ser Ser Leu Gln Pro
            65                  70                  75                  80

Glu Asp Phe Ala Thr Tyr Tyr Cys Gln His Gln Tyr Gly Pro Pro Phe
                            85                  90                  95

Thr Phe Gly Gln Gly Thr Lys Leu Glu Ile Lys Arg Thr Val Ala Ala
                            100                 105                 110

Pro Ser Val Phe Ile Phe Pro Pro Ser Asp Glu Gln Leu Lys Ser Gly
                            115                 120                 125

Thr Ala Ser Val Val Cys Leu Leu Asn Asn Phe Tyr Pro Arg Glu Ala
                            130                 135                 140

Lys Val Gln Trp Lys Val Asp Asn Ala Leu Gln Ser Gly Asn Ser Gln
            145                 150                 155                 160

Glu Ser Val Thr Glu Gln Asp Ser Lys Asp Ser Thr Tyr Ser Leu Ser
                            165                 170                 175

Ser Thr Leu Thr Leu Ser Lys Ala Asp Tyr Glu Lys His Lys Val Tyr
                            180                 185                 190

Ala Cys Glu Val Thr His Gln Gly Leu Ser Ser Pro Val Thr Lys Ser
                            195                 200                 205

Phe Asn Arg Gly Glu Cys
                            210

<210> SEQ ID NO 19
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Val Gln Ser Gly Ala Glu Val Lys Lys Pro Gly Ala
            1               5                   10                  15

Ser Val Lys Val Ser Cys Lys Ala Ser Gly Tyr Thr Phe Thr Ser Tyr
                            20                  25                  30

Trp Met His Trp Val Arg Gln Ala Pro Gly Gln Gly Leu Glu Trp Met
                            35                  40                  45

Gly Asn Ile Asp Pro Ser Asp Ser Asp Thr His Tyr Asn Gln Lys Phe
            50                  55                  60

Lys Asp Arg Val Thr Met Thr Arg Asp Thr Ser Thr Ser Thr Val Tyr
            65                  70                  75                  80

Met Glu Leu Ser Ser Leu Arg Ser Glu Asp Thr Ala Val Tyr Tyr Cys
                            85                  90                  95

Ala Arg Gly Tyr Ser Lys Tyr Tyr Ala Met Asp Tyr Trp Gly Gln Gly
                            100                 105                 110

Thr Leu Val Thr Val Ser Ser Ala Ser Thr Lys Gly Pro Ser Val Phe
                            115                 120                 125

Pro Leu Ala Pro Ser Ser Lys Ser Thr Ser Gly Gly Thr Ala Ala Leu
            130                 135                 140
```

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Ala Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 20
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Ile Val His Ser
            20                  25                  30

Tyr Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

-continued

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asp Tyr Tyr Ile His
1               5

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ile Asp Pro Glu Asp Gly Glu Thr Lys Tyr Ala Pro Lys Phe Gln
1               5                   10                  15

Gly

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Gly Phe Ala Tyr
1               5

<210> SEQ ID NO 24
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 24

Ala Ser Ser Ser Val Ser Ser Ser Tyr Leu Tyr
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Thr Ser Asn Leu Ala Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

His Gln Trp Ser Ser His Pro Tyr Thr
1               5

<210> SEQ ID NO 27
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Ile His Trp Val Lys Gln Arg Thr Glu Gln Gly Leu Glu Trp Ile
        35                  40                  45

Gly Arg Ile Asp Pro Glu Asp Gly Glu Thr Lys Tyr Ala Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Asn Ser Leu Thr Ser Glu Asp Thr Ala Val Tyr Ser Cys
                85                  90                  95

Ala Lys Gly Gly Phe Ala Tyr Trp Gly Gln Gly Thr Leu Val Thr Val
            100                 105                 110

Ser Ala

<210> SEQ ID NO 28
<211> LENGTH: 108
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 28

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Val Ser Ser Ser
            20                  25                  30

Tyr Leu Tyr Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Ser Ser His Pro
                85                  90                  95

Tyr Thr Phe Gly Gly Gly Thr Lys Leu Glu Ile Lys
            100                 105

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Tyr Trp Met His
1               5

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asn Ile Asp Pro Ser Asp Ser Asp Thr His Tyr Asn Gln Lys Phe Lys
1               5                   10                  15

Asp

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Tyr Gly Asn Tyr Gly Glu Asn Ala Met Asp Tyr
1               5                   10

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Ser Ser Gln Ser Ile Val His Ser Tyr Gly Asn Thr Tyr Leu Glu
1               5                   10                  15

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Lys Val Ser Asn Arg Phe Ser
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Phe Gln Gly Ser His Val Pro Phe Thr
1               5

<210> SEQ ID NO 35
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Lys Leu Gln Glu Ser Gly Ala Glu Leu Val Arg Pro Gly Ser
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Ile Gln Gly Leu Glu Trp Ile
            35                  40                  45

Gly Asn Ile Asp Pro Ser Asp Ser Asp Thr His Tyr Asn Gln Lys Phe
        50                  55                  60

Lys Asp Lys Ala Thr Leu Thr Val Asp Asn Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ser Tyr Gly Asn Tyr Gly Glu Asn Ala Met Asp Tyr Trp Gly Gln
            100                 105                 110

Gly Thr Ser Val Thr Val Ser Ser
        115                 120

<210> SEQ ID NO 36
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Leu Met Thr Gln Thr Pro Leu Ser Leu Pro Val Ser Leu Gly

```
              1               5                  10                 15
Asp Gln Ala Ser Ile Ser Cys Arg Ser Ser Gln Ser Ile Val His Ser
             20                  25                 30

Tyr Gly Asn Thr Tyr Leu Glu Trp Tyr Leu Gln Lys Pro Gly Gln Ser
         35                  40                 45

Pro Lys Leu Leu Ile Tyr Lys Val Ser Asn Arg Phe Ser Gly Val Pro
 50                  55                 60

Asp Arg Phe Ser Gly Ser Gly Ser Gly Thr Asp Phe Thr Leu Lys Ile
 65                  70                 75                 80

Ser Arg Val Glu Ala Glu Asp Leu Gly Val Tyr Tyr Cys Phe Gln Gly
                 85                  90                 95

Ser His Val Pro Phe Thr Phe Gly Ser Gly Thr Lys Leu Glu Ile Lys
                100                 105                110
```

<210> SEQ ID NO 37
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
caggttcagt tggttcagtc tggcgccgaa gtgaagaaac ctggcgcctc tgtgaaggtg     60
tcctgcaagg cttccggcta cacctttacc agctactgga tcacctgggt caagcaggct    120
cctggacagg gactcgagtg gatcggcgat atctatcctg ctccggctc accaaccac      180
atcgagaagt tcaagtccaa ggctaccctg accgtggaca cctccatctc caccgcctac    240
atggaactgt cccggctgag atctgacgac accgccgtgt actattgcgc taccggctac    300
ggctcctcct acggctactt tgattattgg ggccagggca cctggtcac cgtgtcctct    360
gcttctacca agggacccag cgtgttccct ctggctcctt ccagcaagtc tacctctggc    420
ggaacagctg ctctgggctg cctggtcaag gactactttc ctgagcctgt gaccgtgtct    480
tggaactctg gcgctctgac atctggcgtg cacacattcc ctgctgtgct gcagtcctcc    540
ggcctgtact ctctgtcctc tgtcgtgacc gtgccttcca gctctctggg aacccagacc    600
tacatctgca atgtgaacca caagccttcc aacaccaagg tggacaagaa ggtggaaccc    660
aagtcctgcg acaagaccca cacctgtcct ccatgtcctg ctccagaact gctcggcgga    720
ccttccgtgt ttctgttccc tccaaagcct aaggacaccc tgatgatctc tcggacccct    780
gaagtgacct gcgtggtggt ggatgtgtct cacgaggacc cagaagtgaa gttcaattgg    840
tacgtggacg gcgtggaagt gcacaacgcc aagaccaagc ctagagagga acagtacgcc    900
tccacctaca gtggtgtc cgtgctgaca gtgctgcacc aggattggct gaacggcaaa    960
gagtacaagt gcaaggtgtc caacaaggcc ctgcctgctc tatcgaaaa gaccatctcc   1020
aaggccaagg gccagcctag ggaacccag gtttacaccc tgccacctag ccgggaagag   1080
atgaccaaga accaggtgtc cctgacctgc ctcgtgaagg gcttctaccc ttccgatatc   1140
gctgtggaat gggagagcaa cggccagcct gagaacaact acaagacaac ccctcctgtg   1200
ctggactccg acggctcatt cttttctgtac tccaagctga ctgtggacaa gtccagatgg   1260
cagcagggca acgtgttctc ctgcagcgtg atgcacgagg ccctgcacaa tcactacaca   1320
cagaagtctc tgtctctgag ccccggc                                      1347
```

<210> SEQ ID NO 38

<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 38

```
gacatccaga tgacccagtc tccatcctct ctgtccgcct ctgtgggcga cagagtgacc    60
atcacctgtc gggcctccga aacatctac tcctacctgg cctggtatca gcagaagcct   120
ggcaaggctc ccaagctgct gatctacacc gctaagacac tggccgaggg cgtgccctct   180
agattttctg gctctggaag cggcaccgac tttacccctga caatctccag cctgcagcct   240
gaggacttcg ccacctacta ctgccagcac cagtacggcc ctccattcac ctttggccag   300
ggcaccaagc tggaaatcaa gcggacagtg gccgctcctt ccgtgttcat cttcccacct   360
tccgacgagc agctgaagtc tggcacagcc tctgtcgtgt gcctgctgaa caacttctac   420
cctcgggaag ccaaggtgca gtggaaggtg gacaatgccc tgcagtccgg caactcccaa   480
gagtctgtga ccgagcagga ctccaaggac agcacctaca gcctgtcctc cacactgacc   540
ctgtccaagg ccgactacga aagcacaag gtgtacgcct gcgaagtgac ccatcagggc   600
ctgtctagcc ctgtgaccaa gtctttcaac cggggcgagt gc                      642
```

<210> SEQ ID NO 39
<211> LENGTH: 1344
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 39

```
caggttcagt tggttcagtc tggcgccgaa gtgaagaaac ctggcgcctc tgtgaaggtg    60
tcctgcaagg cttccggcta caccttttacc agctactgga tgcactgggt ccgacaggct   120
ccaggacaag gcttggagtg gatgggcaac atcgacccct ctgacagcga caccactcac   180
aaccagaaat tcaaggaccg cgtgaccatg accagagaca cctccaccag caccgtgtac   240
atggaactgt ccagcctgag atccgaggac accgccgtgt actactgtgc cagaggctac   300
tccaagtact acgccatgga ctactgggc cagggcacac tggttaccgt gtcctctgct   360
tccaccaagg gaccctctgt gttccctctg ctccttcca gcaagtctac ctctggcgga   420
acagctgctc tgggctgcct ggtcaaggac tactttcctg agcctgtgac cgtgtcttgg   480
aactctggcg ctctgacatc tggcgtgcac acattccctg ctgtgctgca gtcctccggc   540
ctgtactctc tgtcctctgt cgtgaccgtg ccttccagct ctctgggaac ccagacctac   600
atctgcaatg tgaaccacaa gccttccaac accaaggtgg acaagaaggt ggaacccaag   660
tcctgcgaca gacccacac ctgtcctcca tgtcctgctc cagaactgct cggcggacct   720
tccgtgtttc tgttccctcc aaagcctaag gacaccctga tgatctctcg gacccctgaa   780
gtgacctgcg tggtggtgga tgtgtcccac gaagatccag aagtgaagtt caattggtac   840
gtggacggcg tggaagtgca caacgccaag accaagccta gagaggaaca gtacgcctcc   900
acctacagag tggtgtccgt gctgacagtg ctgcaccagg attggctgaa cggcaaagag   960
tacaagtgca aggtgtccaa caaggccctg cctgctccta tcgaaaagac catctccaag  1020
gccaagggcc agcctaggga accccaggtt tacaccctgc ctccaagccg ggaagagatg  1080
accaagaacc aggtgtccct gacctgcctc gtgaagggct tctaccctc cgatatcgcc  1140
```

```
gtggaatggg agagcaatgg ccagccagag aacaactaca agacaaccc tcctgtgctg      1200 gactccgacg gctcattctt tctgtactcc aagctgaccg tggacaagtc cagatggcag      1260
cagggcaacg tgttctcctg cagcgtgatg cacgaggccc tgcacaatca ctatacccag      1320
aagtccctgt ctctgtcccc tggc                                             1344

<210> SEQ ID NO 40
<211> LENGTH: 657
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
gacatcgtga tgacccagac acctctgagc ctgagcgtga cacctggaca gcctgcctcc       60
atctcctgca gatcctctca gtccatcgtg cactcctacg gcaacaccta cctggaatgg      120
tatctgcaga agcccggcca gtctcctcag ctgctgatct acaaggtgtc caaccggttc      180
tctggcgtgc ccgacagatt ttccggctct ggctctggca ccgacttcac cctgaagatc      240
tccagagtgg aagccgagga cgtgggcgtg tactactgct ccaaggctc tcacgtgccc      300 tacacctttg gccagggcac caagctggaa atcaagcgga cagtggccgc tccttccgtg      360
ttcatcttcc accttccga cgagcagctg aagtccggca gcttctgt cgtgtgcctg      420 ctgaacaact ctaccctcg ggaagccaag gtgcagtgga aggtggacaa tgccctgcag      480
tccggcaact cccaagagtc tgtgaccgag caggactcca aggacagcac ctacagcctg      540
tccagcacac tgaccctgtc caaggccgac tacgagaagc acaaggtgta cgcctgcgaa      600
gtgacccatc agggcctgtc tagccctgtg accaagtctt tcaaccgggg cgagtgc       657

<210> SEQ ID NO 41
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
gaggttcagc tgcagcagtc tggggcagag cttgtgaagc caggggcctc agtcaagttg       60
tcctgcacag cttctggctt caacattaaa gactactata tacactgggt gaagcagagg      120
actgaacagg gcctggagtg gattggaagg attgatcctg aggatggtga aactaaatat      180
gccccgaaat tccagggcaa ggccactata acagcagaca catcctccaa cacagcctac      240
ctgcagctca acagcctgac atctgaggac actgccgtct attcctgtgc taagggggg       300 tttgcttact ggggccaagg gactctggtc actgtctctg ca                          342

<210> SEQ ID NO 42
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
caaattgttc tcacccagtc tccagcaatc atgtctgcat ctcctgggga gaaggtcacc       60
ttgacctgca gtgccagttc aagtgtaagt tccagctact tgtactggta ccagcagaag      120
```

```
ccaggatcct cccccaaact ctggatttat agcacatcca acctggcttc tggagtccct    180
gctcgcttca gtggcagtgg gtctgggacc tcttactctc tcacaatcag cagcatggag    240
gctgaagatg ctgcctctta tttctgccat cagtggagta gtcacccgta cacgttcgga    300 gggggggacca agctggaaat aaaa                                          324
```

<210> SEQ ID NO 43
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

```
caggtcaagc tgcaggagtc tggggctgag ctggtgaggc ctgggtcttc agtgaagctg     60
tcctgcaagg cttctggcta caccttcacc agctactgga tgcattgggt gaagcagagg    120
cctatacaag gccttgaatg gattggtaac attgacccct tctgatagtga tactcactac    180 aatcaaaagt tcaaggacaa ggccacattg actgtggaca actcctccag cacagcctac    240
atgcagctca gcagcctgac ctctgaggac tctgcggtct attactgtgc aagctatggt    300
aactacgggg agaatgctat ggactactgg ggtcaaggaa cctcagtcac cgtctcctca    360
```

<210> SEQ ID NO 44
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44

```
gatattttga tgacccaaac tccactctcc ctgcctgtca gtcttggaga tcaagcctcc     60
atctcttgca gatctagtca gagcattgta catagttatg gaaacaccta tttagaatgg    120
tacctgcaga aaccaggcca gtctccaaaa ctcctgatct acaaagtttc caaccgattt    180
tctggggtcc cagacaggtt cagtggcagt ggatcaggta cagatttcac actcaagatc    240
agcagagtgg aggctgagga tctgggagtt tattactgct ttcaaggttc acatgttcca    300
ttcacgttcg gctcggggac aaagttggaa ataaaa                              336
```

<210> SEQ ID NO 45
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
```

```
                65                  70                  75                  80
Ile Thr Pro Ala Asp Ala Gly Thr Tyr Tyr Cys Val Lys Phe Arg Lys
                    85                  90                  95

Gly Ser Pro Asp Asp Val Glu Phe Lys Ser Gly Ala Gly Thr Glu Leu
                100                 105                 110

Ser Val Arg Ala
        115

<210> SEQ ID NO 46
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Tyr
                20                  25                  30

Tyr Ile His Trp Val Gln Ala Pro Gly Lys Gly Leu Glu Trp Ile
            35                  40                  45

Gly Arg Ile Asp Pro Glu Asp Gly Thr Lys Tyr Ala Pro Lys Phe
    50                  55                  60

Gln Asp Arg Ala Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Ala Tyr Trp Gly Gln Gly Thr Leu Val Thr Val Ser
                100                 105                 110

Ser

<210> SEQ ID NO 47
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Ile Val Leu Thr Gln Ser Pro Pro Thr Leu Ser Leu Ser Pro Gly
1               5                   10                  15

Glu Arg Val Thr Leu Thr Cys Ser Ala Ser Ser Ser Val Ser Ser Ser
                20                  25                  30

Tyr Leu Tyr Trp Tyr Gln Gln Lys Pro Gly Gln Ala Pro Lys Leu Trp
            35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Thr Leu Thr Ile Ser Ser Leu Gln
65                  70                  75                  80

Pro Glu Asp Phe Ala Val Tyr Phe Cys His Gln Trp Ser Ser Tyr Pro
                85                  90                  95

Arg Thr Phe Gly Ala Gly Thr Lys Leu Glu Ile Lys
                100                 105

<210> SEQ ID NO 48
```

-continued

```
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala
        115

<210> SEQ ID NO 49
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala
        115

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments
```

```
<400> SEQUENCE: 50

Gly Gly Gly Gly Ser
1               5

<210> SEQ ID NO 51
<211> LENGTH: 4
<212> TYPE: PRT
<213> ORGANISM: Homo sapiens

<400> SEQUENCE: 51

Glu Leu Leu Gly
1

<210> SEQ ID NO 52
<211> LENGTH: 4
<212> TYPE: PRT
<213> ORGANISM: Homo sapiens

<400> SEQUENCE: 52

Glu Phe Leu Gly
1

<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tagaatacag gctcatgttg caggt                                          25

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gccttcagca aatagcatga cgt                                            23

<210> SEQ ID NO 55
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Val Gln Leu Gln Gln Pro Gly Ala Glu Arg Val Lys Pro Gly Ala
1               5                   10                  15

Ser Val Lys Met Ser Cys Lys Ala Ser Gly Tyr Thr Phe Thr Ser Tyr
            20                  25                  30

Trp Ile Thr Trp Val Lys Gln Arg Pro Gly Gln Gly Leu Glu Trp Ile
        35                  40                  45

Gly Asp Ile Tyr Pro Gly Ser Gly Ser Thr Asn His Ile Glu Lys Phe
    50                  55                  60

Lys Ser Lys Ala Thr Leu Thr Val Asp Thr Ser Ser Asn Thr Ala Tyr
65                  70                  75                  80
```

Met Gln Leu Ser Arg Leu Thr Ser Glu Asp Ser Ala Val Tyr Tyr Cys
                85                  90                  95

Ala Thr Gly Tyr Gly Ser Ser Tyr Gly Tyr Phe Asp Tyr Trp Gly Gln
            100                 105                 110

Gly Thr Thr Leu Thr Val Ser Ser
        115                 120

<210> SEQ ID NO 56
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Thr Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Asn Tyr Tyr Cys Gln His Gln Tyr Gly Pro Pro Phe
                85                  90                  95

Thr Phe Gly Ser Gly Thr Arg Leu Val Ile Lys
            100                 105

<210> SEQ ID NO 57
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Ile Gln Gly Leu Glu Trp Ile
        35                  40                  45

Gly Asn Ile Asp Pro Ser Asp Ser Asp Thr His Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Tyr Ser Lys Tyr Tyr Ala Met Asp Tyr Trp Gly Gln Gly
            100                 105                 110

Thr Ser Val Thr Val Ser Ser
        115

<210> SEQ ID NO 58

```
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Val Leu Met Thr Gln Thr Pro Leu Ser Leu Ser Val Ser Leu Gly
1               5                   10                  15

Asp Gln Ala Ser Ile Ser Cys Arg Ser Ser Gln Ser Ile Val His Ser
            20                  25                  30

Tyr Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110
```